(12) United States Patent
Stults et al.

(10) Patent No.: US 7,906,758 B2
(45) Date of Patent: Mar. 15, 2011

(54) SYSTEMS AND METHOD FOR DISCOVERY AND ANALYSIS OF MARKERS

(75) Inventors: John T. Stults, Redwood City, CA (US);
Alfred Greenquist, San Jose, CA (US);
Alexander Sassi, Berkeley, CA (US)

(73) Assignee: Vern Norviel, San Jose, CA (US)

( * ) Notice: Subject to any disclaimer, the term of this patent is extended or adjusted under 35 U.S.C. 154(b) by 301 days.

(21) Appl. No.: 12/172,988

(22) Filed: Jul. 14, 2008

(65) Prior Publication Data
US 2009/0057550 A1 Mar. 5, 2009

Related U.S. Application Data

(63) Continuation of application No. 11/178,262, filed on Jul. 8, 2005, now Pat. No. 7,425,700, and a continuation-in-part of application No. 10/760,100, filed on Jan. 16, 2004, now abandoned, which is a continuation-in-part of application No. 10/645,863, filed on Aug. 20, 2003, now abandoned.

(60) Provisional application No. 60/473,272, filed on May 22, 2003.

(51) Int. Cl.
*B01D 59/44* (2006.01)
(52) U.S. Cl. ............. 250/282; 250/281; 250/288; 435/6; 435/7.1; 435/7.23; 436/52; 436/63; 436/64; 514/13; 514/14; 702/19; 702/22; 706/16; 706/48
(58) Field of Classification Search .................. 250/281, 250/282, 288; 435/6, 7.1, 7.23; 436/52, 436/63, 64; 514/13, 14; 702/19, 22; 706/16, 706/48
See application file for complete search history.

(56) References Cited

U.S. PATENT DOCUMENTS
4,443,319 A 4/1984 Chait et al.
(Continued)

FOREIGN PATENT DOCUMENTS
EP 0881494 A1 12/1998
(Continued)

OTHER PUBLICATIONS

Adam, Bao-Ling, et al., "Serum protein fingerprinting coupled with a pattern-matching algorithm distinguishes prostate cancer from benign prostate hyperplasia and healthy men". Cancer Research, (2002) 62:3609-3614.

(Continued)

*Primary Examiner* — David A Vanore
(74) *Attorney, Agent, or Firm* — Wilson Sonsini Goodrich & Rosati

(57) ABSTRACT

The present invention relates to a charged particle beam apparatus which employs a scanning electron microscope for sample inspection and defect review. The present invent provides solution of improving imaging resolution by utilizing a field emission cathode tip with a large tip radius, applying a large accelerating voltage across ground potential between the cathode and anode, positioning the beam limit aperture before condenser lens, utilizing condenser lens excitation current to optimize image resolution, applying a high tube bias to shorten electron travel time, adopting and modifying SORIL objective lens to ameliorate aberration at large field of view and under electric drifting and reduce the urgency of water cooling objective lens while operating material analysis. The present invent provides solution of improving throughput by utilizing fast scanning ability of SORIL and providing a large voltage difference between sample and detectors.

20 Claims, 21 Drawing Sheets

AN INTEGRATED SYSTEM FOR COMPLEX MIXTURE ANALYSIS

U.S. PATENT DOCUMENTS

| | | | |
|---|---|---|---|
| 4,483,885 A | 11/1984 | Chait et al. |
| 4,977,320 A | 12/1990 | Chowdhury et al. |
| 5,045,694 A | 9/1991 | Beavis et al. |
| 5,227,471 A | 7/1993 | Wright, Jr. |
| 5,245,186 A | 9/1993 | Chait et al. |
| 5,296,114 A | 3/1994 | Manz |
| 5,314,996 A | 5/1994 | Wright, Jr. |
| 5,358,618 A | 10/1994 | Ewing et al. |
| 5,393,975 A | 2/1995 | Hail et al. |
| 5,545,304 A | 8/1996 | Smith et al. |
| 5,599,432 A | 2/1997 | Manz et al. |
| 5,624,539 A | 4/1997 | Ewing et al. |
| 5,639,656 A | 6/1997 | Wright, Jr. |
| 5,652,427 A | 7/1997 | Whitehouse et al. |
| 5,788,166 A | 8/1998 | Valaskovic et al. |
| 5,833,861 A | 11/1998 | Afeyan et al. |
| 5,856,671 A | 1/1999 | Henion et al. |
| 5,872,010 A | 2/1999 | Karger et al. |
| 5,917,184 A | 6/1999 | Carson et al. |
| 5,952,653 A | 9/1999 | Covey et al. |
| 5,958,202 A | 9/1999 | Regnier et al. |
| 5,993,633 A | 11/1999 | Smith et al. |
| 6,017,693 A | 1/2000 | Yates, III et al. |
| 6,033,546 A | 3/2000 | Ramsey |
| 6,068,749 A | 5/2000 | Karger et al. |
| 6,086,243 A | 7/2000 | Paul et al. |
| 6,091,502 A | 7/2000 | Weigl et al. |
| 6,107,628 A | 8/2000 | Smith et al. |
| 6,139,734 A | 10/2000 | Settlage et al. |
| 6,157,921 A | 12/2000 | Barnhill |
| 6,159,739 A | 12/2000 | Weigl et al. |
| 6,175,112 B1 | 1/2001 | Karger et al. |
| 6,187,190 B1 | 2/2001 | Smith et al. |
| 6,207,370 B1 | 3/2001 | Little et al. |
| 6,207,954 B1 | 3/2001 | Andrien, Jr. |
| 6,225,047 B1 | 5/2001 | Hutchens et al. |
| 6,231,737 B1 | 5/2001 | Ramsey et al. |
| 6,240,790 B1 | 6/2001 | Swedberg et al. |
| 6,277,641 B1 | 8/2001 | Yager et al. |
| 6,280,589 B1 | 8/2001 | Manz et al. |
| 6,284,113 B1 | 9/2001 | Bjornson et al. |
| 6,284,115 B1 | 9/2001 | Apffel |
| 6,306,087 B1 | 10/2001 | Barnhill et al. |
| 6,309,816 B1 | 10/2001 | Zhang et al. |
| 6,318,970 B1 | 11/2001 | Backhouse |
| 6,322,682 B1 | 11/2001 | Arvidsson et al. |
| 6,329,209 B1 | 12/2001 | Wagner et al. |
| 6,342,142 B1 | 1/2002 | Ramsey |
| 6,358,692 B1 | 3/2002 | Jindal et al. |
| 6,363,383 B1 | 3/2002 | Kindo et al. |
| 6,368,562 B1 | 4/2002 | Yao |
| 6,375,817 B1 | 4/2002 | Taylor et al. |
| 6,379,971 B1 | 4/2002 | Schneider et al. |
| 6,427,141 B1 | 7/2002 | Barnhill |
| 6,558,955 B1 | 5/2003 | Kristal et al. |
| 6,593,298 B2 | 7/2003 | Jackowski et al. |
| 6,599,877 B2 | 7/2003 | Jackowski et al. |
| 6,602,855 B2 | 8/2003 | Jackowski et al. |
| 6,617,308 B2 | 9/2003 | Jackowski et al. |
| 6,620,786 B2 | 9/2003 | Jackowski et al. |
| 6,620,787 B2 | 9/2003 | Jackowski et al. |
| 6,627,606 B2 | 9/2003 | Jackowski et al. |
| 6,627,607 B2 | 9/2003 | Jackowski et al. |
| 6,627,608 B2 | 9/2003 | Jackowski et al. |
| 6,658,395 B1 | 12/2003 | Barnhill |
| 6,675,104 B2 | 1/2004 | Paulse et al. |
| 6,677,303 B2 | 1/2004 | Jackowski et al. |
| 6,703,366 B2 | 3/2004 | Jackowski et al. |
| 6,714,925 B1 | 3/2004 | Barnhill et al. |
| 6,756,476 B2 | 6/2004 | Jackowski et al. |
| 6,863,790 B1 | 3/2005 | Moini et al. |
| 7,007,710 B2 * | 3/2006 | Heller et al. ............ 137/15.01 |
| 7,105,812 B2 * | 9/2006 | Zhao et al. .................. 250/288 |
| 7,425,700 B2 * | 9/2008 | Stults et al. ................. 250/288 |
| 7,460,960 B2 * | 12/2008 | Lee et al. ..................... 702/27 |
| 2001/0014461 A1 | 8/2001 | Hutchens et al. |
| 2001/0041357 A1 | 11/2001 | Fouillet et al. |
| 2002/0036140 A1 | 3/2002 | Manz et al. |
| 2002/0039747 A1 | 4/2002 | Lubman et al. |
| 2002/0041827 A1 | 4/2002 | Yager et al. |
| 2002/0048777 A1 | 4/2002 | Ali et al. |
| 2002/0054289 A1 | 5/2002 | Thibault et al. |
| 2002/0095260 A1 | 7/2002 | Huyn |
| 2002/0119490 A1 | 8/2002 | Aebersold et al. |
| 2002/0127237 A1 | 9/2002 | Salceda et al. |
| 2002/0138208 A1 | 9/2002 | Paulse et al. |
| 2002/0142481 A1 | 10/2002 | Andersson et al. |
| 2002/0177140 A1 | 11/2002 | Salceda et al. |
| 2002/0193950 A1 | 12/2002 | Gavin et al. |
| 2003/0004402 A1 | 1/2003 | Hitt et al. |
| 2003/0013120 A1 | 1/2003 | Patz, Jr. et al. |
| 2003/0032043 A1 | 2/2003 | Pohl et al. |
| 2003/0039983 A1 | 2/2003 | Sun et al. |
| 2003/0064377 A1 | 4/2003 | Sun et al. |
| 2003/0077611 A1 | 4/2003 | Slepnev |
| 2003/0078739 A1 | 4/2003 | Norton et al. |
| 2003/0089605 A1 | 5/2003 | Timperman |
| 2003/0111596 A1 | 6/2003 | Becker et al. |
| 2003/0129760 A1 | 7/2003 | Aguilera et al. |
| 2003/0132114 A1 | 7/2003 | Mischak et al. |
| 2003/0134304 A1 * | 7/2003 | van der Greef et al. ......... 435/6 |
| 2003/0148295 A1 | 8/2003 | Wan et al. |
| 2003/0148922 A1 | 8/2003 | Knapp et al. |
| 2003/0153007 A1 | 8/2003 | Chen et al. |
| 2003/0175707 A1 | 9/2003 | Sun et al. |
| 2003/0194739 A1 | 10/2003 | Ali et al. |
| 2003/0199001 A1 | 10/2003 | Pitt et al. |
| 2003/0224531 A1 | 12/2003 | Brennen et al. |
| 2003/0228639 A1 | 12/2003 | Wright et al. |
| 2004/0005634 A1 | 1/2004 | Patz, Jr. et al. |
| 2004/0018519 A1 * | 1/2004 | Wright , Jr. ....................... 435/6 |
| 2004/0029194 A1 | 2/2004 | Parish et al. |
| 2004/0033591 A1 | 2/2004 | Lubman et al. |
| 2004/0043436 A1 | 3/2004 | Vlahou et al. |
| 2004/0053333 A1 | 3/2004 | Hitt et al. |
| 2004/0075050 A1 | 4/2004 | Rossier et al. |
| 2004/0153249 A1 | 8/2004 | Zhang et al. |
| 2004/0180380 A1 * | 9/2004 | Lee et al. ....................... 435/7.1 |
| 2004/0235052 A1 | 11/2004 | Heller et al. |
| 2004/0236603 A1 | 11/2004 | Heller et al. |
| 2005/0059013 A1 | 3/2005 | Chan et al. |
| 2005/0072915 A1 | 4/2005 | Stults et al. |
| 2005/0244973 A1 | 11/2005 | Andel, III et al. |
| 2006/0027744 A1 | 2/2006 | Stults et al. |
| 2006/0186048 A1 | 8/2006 | Tan |
| 2007/0009970 A1 | 1/2007 | Heller et al. |

FOREIGN PATENT DOCUMENTS

| | | |
|---|---|---|
| EP | 1512970 A1 | 3/2005 |
| WO | WO 95/25281 A1 | 9/1995 |
| WO | WO 00/23111 A1 | 4/2000 |
| WO | WO 00/63683 A1 | 10/2000 |
| WO | WO 00/65472 A1 | 11/2000 |
| WO | WO 01/25791 A2 | 4/2001 |
| WO | WO 01/36977 A2 | 5/2001 |
| WO | WO 01/57263 A1 | 8/2001 |
| WO | WO 01/57518 A2 | 8/2001 |
| WO | WO 01/71360 A2 | 9/2001 |
| WO | WO 02/04957 A2 | 1/2002 |
| WO | WO 02/06829 A2 | 1/2002 |
| WO | WO 02/08760 A1 | 1/2002 |
| WO | WO 02/27329 A2 | 4/2002 |
| WO | WO 02/46448 A2 | 6/2002 |
| WO | WO 02/007703 A2 | 12/2002 |
| WO | WO 03/014302 A2 | 2/2003 |
| WO | WO 03/031031 A1 | 4/2003 |
| WO | WO 03/038055 A2 | 5/2003 |
| WO | WO 03/042774 A2 | 5/2003 |
| WO | WO 03/057014 A2 | 7/2003 |
| WO | WO 03/058198 A2 | 7/2003 |
| WO | WO 03/072710 A2 | 9/2003 |
| WO | WO 03/083442 A2 | 10/2003 |
| WO | WO 03/086445 A1 | 10/2003 |
| WO | WO 03/089937 A2 | 10/2003 |
| WO | WO 03/091695 A2 | 11/2003 |
| WO | WO 03/097799 A2 | 11/2003 |
| WO | WO 2004/012588 A2 | 2/2004 |

| | | | |
|---|---|---|---|
| WO | WO 2004/013609 A2 | 2/2004 |
| WO | WO 2004/030511 A2 | 4/2004 |
| WO | WO 2004/055519 A2 | 7/2004 |
| WO | WO 2004/061407 A2 | 7/2004 |
| WO | WO 2004/061410 A2 | 7/2004 |
| WO | WO 2004/068130 A2 | 8/2004 |
| WO | WO 2004/102190 A1 | 11/2004 |
| WO | WO 2005/011474 A2 | 2/2005 |
| WO | WO 2005/020125 A2 | 3/2005 |
| WO | WO 2005/024409 A1 | 3/2005 |

OTHER PUBLICATIONS

Adkins, Joshua N., et al., "Toward a human blood serum proteome: analysis by multidimensional separation coupled with mass spectrometry". The American Society for Biochemistry and Molecular Biology, Inc., MCP Paper (Nov. 15, 2002).

Anderson, Leigh, et al., "A comparison of selected mRNA and protein abundances in human liver". Electrophoresis (1997), 18:533-537.

Anderson, N. Leigh, et al., "The Human Plasma Proteome". Molecular & Cellular Proteomics (2002), 1:845-867.

Auriola, Seppo et al., "Enhancement of sample loadings for the analysis of oligosaccharides isolated from Pseudomonas aeruginosa using transient isotachophoresis—electrospray—mass spectrometry". Electrophoresis (1998), 19:2665-2676.

Banez, Lionel L., et al., "Diagnostic potential of serum proteomic patterns in prostate cancer". The Journal of Urology (2003) 170:442-446.

Bertero, M., "Linear inverse and ill-posed problems". In Advances in Electronics and Electronic Physics. Academic Press (1989), NY.

Billingsley, Janice, "Research offers hope in fight against ovarian cancer". Health & Science (Feb. 8, 2002) 3 pages.

Cao, Ping et al., "Analysis of peptides, proteins, protein digests, and whole human blood by capillary electrophoresis/electrospray ionization-mass spectrometry using an in-capillary electrode sheathless interface". J Am Soc Mass Spectrometry (1998), 9:1081-1088.

Cazares, L. H., et al., "Normal, benign, preneoplastic, and malignant prostate cells have distinct protein expression profiles resolved by surface enhanced laser desorption/ionization mass spectrometey". Clinical Cancer Research (Aug. 2002) 8:2541-2552.

CBS News, "Setback for a silent killer". CBS News.com (Apr. 2, 2002), 2 pages.

Chambers, et al., "Proteomics: A New Approach to the Study of Disease". Journal of Pathology 2000; 192:280-288.

Chen , S.S., et al., "Atomic decomposition by basis pursuit". SIAM Journal on Scientific Computing, (1988), 20(1):33-61.

Covey, Thomas R., et al., "Structural characterization of protein tryptic peptides liquid via chromatography/mass spectrometry and collision-induced dissociation of their doubly charged molecular ions". Anal. Chem. (1991), 63:1193-1200.

Crisp—Computer retrieval of information on scientific projects [abstract], <<http://commons.clt.n1h.gov/crisp3/CRISP _LIB.getdoc?textkey=6388327&p_grant_num=5R0 1HG002033-03&p_query=&ticket=. . . >>. Downloaded May 9, 2002, 2 pages.

Diamandis, Eleftherios P., "Point proteomic patterns in biological fluids: do they represent the future of cancer diagnostics?". Clinical Chemistry (2003) 49(8)1272-1278.

Donoho, D. L., "Nonlinear solution of linear inverse problems by wavelet-vaguelette decomposition". App. and Comp. Harmonic Analysis, (1995), 2:101-126.

Donoho, D. L., "Unconditional bases are optimal bases for data compression and for statistical estimation". Applied and Computational Harmonic Analysis, (1993), 1(1):100-115.

Donoho, D. L., et al. "Adapting to unknown smoothness via wavelet shrinkage". Journal of the American Statistical Association, (1995), 90(432):1200-1224.

Editorial, "Proteomic diagnostics tested". Nature (Jun. 3, 2004), 429(3)487.

Etzioni, Ruth, et al., "Combining biomarkers to detect disease with application to prostate cancer". Biostatistics (2003), 4(4)523-538.

Etzioni, Ruth, et al., "The case for early detection". Nature Reviews/Cancer (Apr. 2003), 3:1-10.

Figeys, Daniel et al., "High sensitivity analysis of proteins and peptides by capillary electrophoresis-tandem mass spectrometry: recent developments in technology and applications". Electrophoresis, (1998), 19:885-892.

Fung, Eric T., et al., "Classification of cancer types by measuring variants of host response proteins using SELDI serum assays," Int. J. Cancer (2005) 115:783-789.

Fung, et al. ProteinChip(R) clinical proteomics: Computational challenges and solutions. Biotechniques. 2002; 32(3): S34-S41.

Geracimos, A., "Outwitting Ovarian Cancer". Correlogic Systems, Inc., Press Release dated Apr. 16, 2002, 4 pages.

Geromanos, S., et al., "Injection adaptable Fine Ionization Source ('JaFIS') for Continuous Flow Nano-electrospray". Rapid Commun. Mass Spectrom (1998) 12:551-556.

Guo, Xu et al., "Analysis of metallonthioneins by means of capillary electrophoresis coupled to electrospray mass spectrometry with sheathless interfacing" Rapid Commun. Mass Spectrom. (1999), 13:500-507.

Guyon, I, et al., "An introduction to variable and feature selection". JMLR, (2003), 1:1-48.

Gygi, Steven P., "Correlation between protein and mRNA abundance in yeast". Molecular and Cellular Biology (Mar. 1999) 1720-1730.

Haran, Christine, "The promise of proteins—Do these tricky molecules hold the answers to cancer?". (Oct. 2002) 43-47.

Harrison, Harold H., et al., "Multiple serum protein abnormalities in carbohydrate-deficient glycoprotein syndrome: pathognomomic finding of two-dimensional electrophoresis?". Clinical Chemistry (1992), 38:1390-1392.

Hayes, Roger N., et al., "Collision-induced dissociation". Methods in Enzymology (1990), 193:237-263.

Henry, Celia, "Diagnosing ovarian cancer—Proteomics shows promise of early detection of deadly disease". Science (Feb. 18, 2003); 13.

Hilario, Melanie, et al., "Machine learning approaches to lung cancer prediction from mass spectra". Protoemics (2003) 3:1716-1719.

Hollon, Tom "Software Zeroes in on ovarian cancer". The Scientist (Apr. 15, 2002) 16(8):16.

Johannes, Laura, "Tiny protein may lead to better screen test for prostate cancer". Dow Jones (Nov. 4, 2003), 1-2.

Kaiser, Thorsten et al., "Capillary electrophoresis coupled to mass spectrometry to establish polypeptide patterns in dialysis fluids". Journal of Chromatography A (2003) 1013:157-171.

Kaiser, Thorsten et al., "Capillary electrophoresis coupled to mass spectrometer for automated and robust polypeptide determination in body fluids for clinical use". Electrophoresis (2004), 25:2044-2055.

Kajita, Yoshihiro, et al., "Clinical Study on Increased Serum Thyroxine-Binding Globulin in Cancerous State," Endocrinol. Japon (1981) 28 (6): 785-791.

Kalifa, Jerome, et al., "Minimax deconvolution in mirror wavelet bases". IEEE Trans. on Image Processing (1999), 1-30.

Kalifa, Jerome, et al., "Thresholding estimators for linear inverse problems and deconvolution". Annals of Statistics (2003), 1:58-109.

Koo, Edward D., et al., "Amyloid diseases: Abnormal protein aggregation in neurodegeneration," Proc. Natl. Acad. Sci. (Aug. 1990) vol. 96: 9989-9990.

Kundin, W.D., et al., "Cancer Serum Index: A useful Nonspecific Test as a Parameter in Multimodality Screening and Assessment of Patients With Cancer of the Prostate," The Prostate (1981) 2:207-217.

Lehrer, S., et al., "Putative protein markers in the sera of men with prostatic neoplasms". BJU International (2003) 92:223-225.

Levine, Peter, "Correlogic's ovarian cancer test nears market introduction". Diagnostic Testing and Technology Report (Jul. 2003) 1:5-7.

LI, et al. Proteomics and Bioinformatics approaches for identification of serum biomakers to detect breast cancer. Clinical Chemistry. 2002; 48(8): 1296-1304.

Li, Jinong et al., "Detection of prostate cancer using serum proteomics pattern in a histologically confirmed population". The Journal of Urology (May 2004), 171:1782-1787.

Liotta, Lance, A., et al., "Written in blood". Nature (Oct. 30, 2003), 425:905.

Markey, Mia K., et al. "Decision tree classification of proteins identified by mass spectrometry of blood serum samples from people with and without lung cancer" Proteomics (2003) 3:1678-1679.

Marshall, John, et al., "Processing of serum proteins underlies the mass spectral fingerprinting of myocardial infraction". Journal of Proteome Research (Jan. 20, 2003) 12 pages.

Mian, Shahid, et al., "A prototype methodology combining surface-enhanced laser desorption/ionization protein chip technology and artificial neural network algorithms to predict the chemoresponsiveness of breast cancer cell lines exposed to Paclitaxel and Doxorubicin under in vitro conditions". Proteomics (2003) 3:1725-1737.

Miller, Jeremy C., et al., "Antibody microarray profiling of human prostate cancer sera: Antibody screening and identification of potential biomarkers". Proteomics (2003) 3:56-63.

Mobley, J.A., et al., "Monitoring the Serological Proteome: The Latest Modality in Prostate Cancer Detection," The Journal of Urology (Jul. 2004) vol. 172: 331-337.

Neuhoff, et al. Mass spectrometry for the detection of differentially espressed proteins: a comparison of surface-enhanced laser desorption/ionization and capillay electrophoresis/mass spectrometry. Rapid Commun. Mass Spectrom. 2004; 18(2): 149-156.

Neusub, Christian et al., "A robust approach for the analysis of peptides in the low femtomole range by capillary electrophoresis-tandem mass spectrometry". Electrophoresis (2002), 23:3149-3159.

Neville, Padraic, et al., "Generalizable mass spectrometry mining used to identify disease state biomarkers from blood serum". Proteomics (2003) 3:1710-1715.

Ornstein, David K., et al., "Serum Proteomic Profiling Can Discriminate Prostate Cancer From Benign Prostates in Men With Total Prostate Specific Antigen Levels Between 2.5 and 15.0 NG/ML," The Journal of Urology (Oct. 2004) vol. 172: 1302-1305.

Paroni, Rita et al., "Creatinine determination in serum by capillary electrophoresis". Electrophoresis (2004), 25:463-468.

Petricoin III, E. F., et al., "Serum proteomic patterns for detection of prostate cancer". JNCI (2002), 94(20):1576-1578.

Petricoin III, E. F., et al., "Use of proteomic patterns in serum to identify ovarian cancer". The Lancet (2002), 359:572-577.

Purohit, Parul V., et al., "Discriminant models for high-throughput proteomics mass spectrometer data". Proteomics (2003) 3:1699-1703.

Qu, Yinsheng, et al., "Boosted decision tree analysis of surface-enhanced laser desorption/ionization mass spectral serum profiles discriminates prostate cancer from noncancer patients". Clinical Chemistry (2002), 48(10):1835-1843.

Reddy, et al. Seldi proteinchip(R) array technology: protein-based predictive medicine and drug discovery applications. Journal of Biomedicine & Biotechnology. 2003; 2003 (4): 237-241.

Reixach, Natalia, et al., "Tissue damage in the amyloidoses: Transthyretin monomers and nonnative oligomers are the major cytotoxic species in tissue culture," PNAS (Mar. 2, 2004) vol. 101 No. 9: 2817-2822.

Robey, Edwin L., et al., "Cancer Serum Index and Prostatic Acid Phosphatase for Detection of Progressive Prostatic Cancer," The Journal of Urology (Oct. 1985) vol. 134: 787-790.

Rohde, E. et al., "Comparison of protein mixtures in aqueous humor by membrane preconcentration—capillary electrophoresis—mass spectrometry". Electrophoresis (1998), 19:2361-2370.

Rostenberg, Israel, et al., "Gc Globulin and Prealbumin Serum Levels in Patients With Cancer and Benign Inflammatory Diseases and in Asymptomatic Smokers," Journal of the National Cancer Institute (Feb. 1997) vol. 62 No. 2:299-300.

Rubin, Rita, "Blood test may spot ovarian cancer earlier" Health & Science (Feb. 8, 2002) 2 pages.

Sassi, Alexander P., et al., "An automated,sheathless capillary electrophoresis-mass spectrometry platform for discovery of biomarkers in human serum". Electrophoresis (2005), 26:pages unknown.

Schultz, Gary A. et al., "Development of a proteome marker model for ovarian cancer using direct analysis of diluted serum by automated nanoelectrospray TOFMS" ASMS (2003) 2 pages.

Schweigert, Florian J., et al., "Transthyretin, a Biomarker for Nutritional Status and Ovarian Cancer," Cancer Research (Feb. 1, 2005) 65 (3):1114.

Service, R.F., "Recruiting genes, proteins for a revolution in diagnostics". Science (Apr. 11, 2003), 300:236-239.

Silva, Chris, "Small company, big partners—Bethesda-based Correlogic Systems enlists allies in quest to bring its concern detection test to market" Washington Business Journal (Aug. 30-Sep. 5, 2002) 2 pages.

Somorjai, R. L., et al., "Class prediction and discovery using gene microarray and proteomics mass spectroscopy data: cruses, caveats, cautions". Bioinfomatrics (2003) 19(12):1484-1491.

Sorace, James M., et al., "A data review and re-assessment of ovarian cancer serum proteomic profiling". BMC Bioinformatics (2003) 4(24):1-13.

Sorlie, Therese, et al., "Gene expression patterns of breast carcinomas distinguish tumor subclasses with clinical implications". PNAS (Sep. 11, 2001), 98(19)10869-10874.

Strand, O. N., "Theory and methods related to the singular function expansion and landweber's iteration for integral equations of the first kind". SIAM J. Num. Anal. (1973), 798-825.

Strittmatter, E. F., et al., "High mass measurement accuracy determination for proteomics using multivariate regression fitting: application to electrospray ionization time-of-flight mass spectrometry". Anal. Chem. (2003), 75(3):460-468.

Stroink, Thom et al., "On-line coupling of size exclusion and capillary zone electrophoresis via a reversed-phase C18 trapping col. for the analysis of structurally related enkephalines in cerebrospinal fluid". Electrophoresis (2003), 24:897-903.

Svedberg, Malin, et al., "Sheathless electrospray from polymer microchips". Anal. Chem. (2003) 75:3934-3940.

Tatay, Jacob W., "Multiple approaches to data-mining of proteomic data based on statistical and pattern classification methods". Proteomics (2003) 3:1704-1709.

Thompson, Ian M., et al., "Prevalence of Prostate Cancer among Men with a Prostate-Specific Antigen Level * 4.0 ng per Milliliter," The New England Journal of Medicine (May 27, 2004) vol. 350 No. 22: 2239-2246.

Tibshirani, Robert, "Regression shrinkage and selection via the lasso". J. Royal Statist. Soc. (1996), 58:267-288.

Tihonov, A. N., "Solution of incorrectly formulated problems and the regularization method". Soviet Math. Doklady (1963), 4:1035-1038.

Tirumalai, Radhakrishna S., et al., "Characterization of the low molecular weight human serum proteome". Molecular & Cellular Proteomics 2.10 (Aug. 13, 2003), 1096-1103.

Touchette, Nancy, "Diagnosing Ovarian Cancer by Proteomics". Genome News Network (2003), 2 pages.

Van 'T Veer, Laura, et al., "Gene expression profiling predicts clinical outcome of breast cancer". Nature (Jan. 2002) 415:530-536.

Vejda, Susanne, et al., "Plasma from Cancer Patients Featuring a Characteristic Protein Composition Mediates Protection against Apoptosis," Molecular & Cellular Proteomics (2002):387-393.

Vestal, M., et al., "Resolution and mass accuracy in matrix-assisted laser desorption ionization-time-of-flight". J. Am. Soc. Mass Spectrom (1998), 9:892-911.

Villanueva, Josep et al., "Serum peptide profiling by magnetic particle-assisted, automated sample processing and MALDI-TOF mass spectrometry". Anal. Chem. (Mar. 15, 2004), 76(6):1560-1570.

Vlahou, Antonia, et al., "Development of a novel proteomic approach for the detection of transitional cell carcinoma of the bladder in urine". American Journal of Pathology (Apr. 2001), 158(4):1491-1502.

Vohradsky, J., "Adaptive classification of two-dimensional gel electrophoretic spot patterns by neural networks and cluster analysis". Electrophoresis (1997), 18:2749-2754.

Wang, Michael Z., et al., "Analysis of human serum proteins by liquid phase isoelectric focusing and matrix-assisted laser desorption/ionization-mass spectrometry". Proteomics (2003), 3:1661-1666.

Ward, A. Milford, et al., "Acute Phase Reactant proteins in Prostatic Cancer," British Journal of Urology (1977), 49: 411-418.

Wehofsky, M., et al. "Isotopic deconvolution of matrix-assisted laser desorption/ionization mass spectra for substance class specific analysis of complex samples". Eur. J. Mass Spectrom (2001), 7:39-46.

Wehofsky, M., et al., "Automated deconvolution and deisotoping of electrospray mass spectra". J. Mass Spectrom. (2002), 37(2):223-229.

Williams, Jon D., et al., "Using accurate mass electrospray ionization-time-of-flight mass spectrometry with in-source collision-induced dissociation to sequence peptide mixtures". Journal of Chromatography A (2003) 1020:11-26.

Wittke, Stefan et al., "Determination of peptides and proteins in human urine with capillary electrophoresis-mass spectrometry, a suitable tool for the establishment of new diagnostic markers". Journal of Chromatography A (2003), 1013:173-181.

Wright, G.L. et al., "Proteinchip surface enhanced laser desorption/ionization (SELDI) mass spectrometry: a novel protein biochip technology for detection of prostate cancer biomarkers in complex protein mixtures". Prostate Cancer and Prostatic Diseases (1999) 2:264-276.

Wu, Baolin, et al., "Comparison of statistical methods for classification of ovarian cancer using mass spectrometry data". Bioinfonnatics (2003) 19(13):1636-1643.

Wu, Shiaw-Lin, et al., "Targeted proteomics of low-level proteins in human plasma by LC/MSn: Using human growth hormone as a model system". Journal of Proteome Research (2002) 1:459-465.

Yanagisawa, Kiyoshi, et al., "Proteomic patterns of tumour subsets in non-small-cell lung cancer". The Lancet (Aug. 9, 2003), 362:433-439.

Yasui, Yataka, et al., "A data-analytic strategy for protein biomarker discovery: profiling of high-dimensional proteomic data for cancer detection". Biostatistics (2003) 4(3):449-463.

Zhang, Zhen, et al., "Three Biomarkers Identified from Serum Proteomic Analysis for the Detection of Early Stage Ovarian Cancer," Cancer Research (Aug. 15, 2004) 64:5882-5890.

Zhu, Hongtu, et al. "Tree-based disease classification using protein data". Proteomics (2003) 3:1673-1677.

Zhu, Wei, et al. "Detection of cancer-specific markers amid massive mass spectral data". PNAS (Dec. 9, 2003) 100(25):14666-14761.

* cited by examiner

AN INTEGRATED SYSTEM FOR COMPLEX MIXTURE ANALYSIS

(a)

(b)

SYSTEMS AND METHOD FOR DISCOVERY AND ANALYSIS OF MARKERS

CROSS REFERENCE TO RELATED APPLICATIONS

This application is a Continuation of U.S. application Ser. No. 11/178,262, filed Jul. 8, 2005, now U.S. Pat. No. 7,425,700 which is a Continuation in Part of U.S. patent application Ser. No. 10/760,100, filed Jan. 16, 2004 now abandoned, which is a Continuation in Part of U.S. application Ser. No. 10/645,863, filed Aug. 20, 2003, now abandoned which claims priority to U.S. Provisional Application No. 60/473,272, filed May 22, 2003, each of which is incorporated herein by reference for all purposes. This application is also related to U.S. application Ser. No. 11/178,245, entitled "BIOLOGICAL PATTERNS FOR DIAGNOSIS AND TREATMENT OF CANCER", filed Jul. 8, 2005, which is incorporated herein by reference for all purposes.

BACKGROUND OF THE INVENTION

The present inventions provide a business system and method for pharmaceutical, diagnostic, and biological research as well as applications of such research. Additionally, the present inventions provide a system for creation of assays such as assays based on the use of mass spectrometry.

A common aspect of all life on earth is the use of polypeptides as functional building blocks and the encryption of the instructions for the building blocks in the blueprint of nucleic acids (DNA, RNA). What distinguishes between living entities lies in the instructions encoded in the nucleic acids of the genome and the way the genome manifests itself in response to the environment as proteins. The complement of proteins, protein fragments, and peptides present at any specific moment in time defines who and what we are at that moment, as well as our state of health or disease.

One of the greatest challenges facing biomedical research and medicine is the limited ability to distinguish between specific biological states or conditions that affect an organism. This is reflected in the limited ability to detect the earliest stages of disease, anticipate the path any apparent disease may or will take in one patient versus another, predict the likelihood of response for any individual to a particular treatment, and preempt the possible adverse affects of treatments on a particular individual.

New technologies and strategies are needed to inform medical care and improve the repertoire of medical tools, as well as methods or business methods to utilize such technologies and strategies.

BRIEF SUMMARY OF THE INVENTION

According to one aspect, the present invention relates to systems comprising: a mass spectrometer; and a microfluidic device adapted for sample separation, wherein said microfluidic device has a electrospray ionization interface to said mass spectrometer. In some embodiments, the system above has a microfluidic device that is disposable and/or is composed of a polymeric material. In some embodiments, the system above has a microfluidic device adapted to reduce the amount of one or more abundant proteins from a sample or to remove sample components that are greater than 50 kD. Removal of abundant protein(s) or of components greater than 50 kD can be carried out using various devices, such as 96 well plates.

In any of the embodiments herein, a sample can be a fluid sample or non-fluid sample. Fluid samples include, but are not limited to serum, plasma, whole blood, nipple aspirate, ductal lavage, vaginal fluid, nasal fluid, ear fluid, gastric fluid, pancreatic fluid, trabecular fluid, lung lavage, urine, cerebrospinal fluid, saliva, sweat, pericrevicular fluid, semen, prostatic fluid, and tears.

In any of the embodiments herein, the detection device can be a mass spectrometer, more preferably a time-of-flight (TOF) mass spectrometer, or more preferably an orthogonal acceleration, time-of-flight (OA-TOF) mass spectrometer (MS).

In any of the embodiments herein, the separation is performed by electrophoresis, more preferably, capillary electrophoresis, or more preferably zone capillary electrophoresis.

According to one aspect, the present invention relates to a method for screening an organism for a biological state or condition of interest comprising the steps of: obtaining a sample from the patient; providing a system comprising: a mass spectrometer and a microfluidic device adapted for sample separation, wherein the microfluidic device has a electrospray ionization interface to the mass spectrometer; and determining if the sample from the patient includes a marker for the biological state or condition of interest.

In any of the embodiments herein an organism and/or a patient is preferably a human; the sample is a body fluid; the sample herein is preferably a blood, serum or plasma sample; and the biological state or condition of interest is selected from the group consisting of: cancer, cardiovascular disease, inflammatory disease, infectious disease, autoimmune disease, neurological disease, and pregnancy related disorders.

A marker identified or used by the methods and systems herein can be a polypeptide, nucleic acid, lipid, small molecule, or any other composition or compound. In some embodiments, a marker is a polypeptide or a small molecule.

According to one aspect, the present invention relates to business methods.

In one embodiment, the business methods herein comprise: identifying one or more markers using a system comprising: a mass spectrometer and a microfluidic device adapted for sample separation, wherein the microfluidic device has an electrospray ionization interface to the mass spectrometer (more preferably electrospray ionization); and commercializing the one or more markers identified in the above step in a diagnostic product. The biomarkers identified are preferably polypeptides or small molecules. Such polypeptides can be previously known or unknown. The diagnostic product herein can include one or more antibodies that specifically binds to the marker (e.g., polypeptide).

In one embodiment, the business methods herein comprise: identifying one or more markers using a system comprising: a mass spectrometer and a microfluidic device adapted for sample separation, wherein the microfluidic device has an electrospray ionization interface to the mass spectrometer; and providing a diagnostic service to determine if an organism has or does not have a biological state or condition of interest. A diagnostic service herein may be provided by a CLIA approved laboratory that is licensed under the business or the business itself. The diagnostic services herein can be provided directly to a health care provider, a health care insurer, or a patient. Thus the business methods herein can make revenue from selling e.g., diagnostic services or diagnostic products.

According to one embodiment of the invention, a business method is provided that includes the steps of collecting more than 10 case samples representing a clinical phenotypic state and more than 10 control samples representing patients without said clinical phenotypic state; using a mass spectrometry platform system to identify patterns of polypeptides in said case samples and in said control samples without regard to the specific identity of at least some of said proteins; identifying representative patterns of the phenotypic state; and marketing diagnostic products using said representative patterns. Such patterns contain preferably more than 15 polypeptides that are represented on output of said mass spectrometer, but the identity of at least some of said more than 15 polypeptides is not known.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Figure 1:
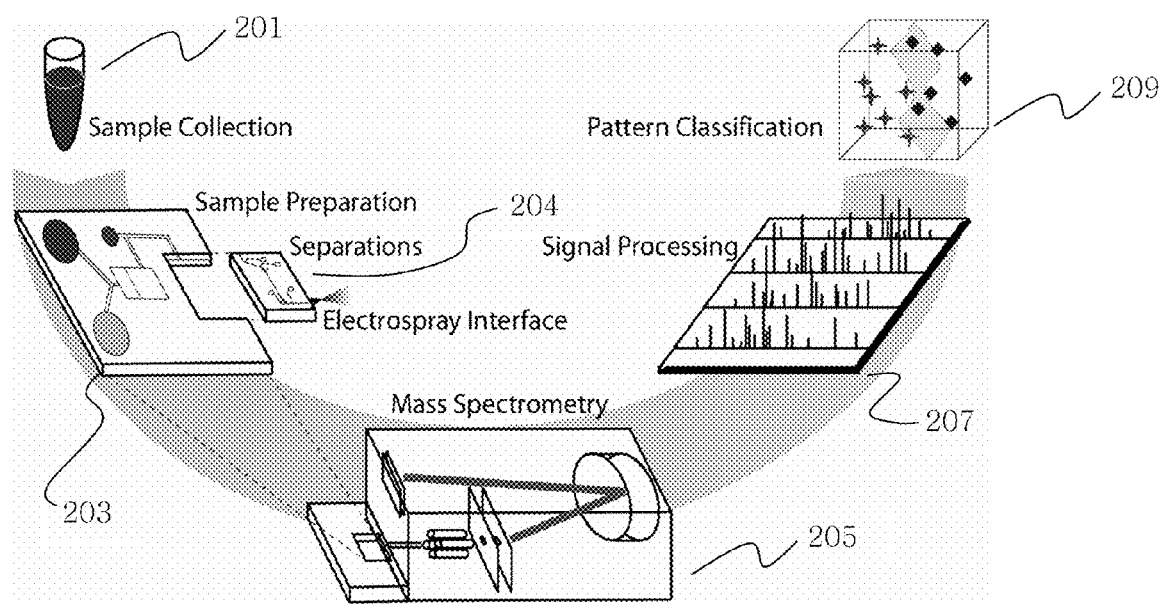
FIG. 1 a diagram illustrating preferred aspects of the inventions and systems used herein.

The term "organism" as used herein refers to any living being comprised of a least one cell. An organism can be as simple as a one cell organism or as complex as a mammal. An organism of the present invention is preferably a mammal. Such mammal can be, for example, a human or an animal such as a primate (e.g., a monkey, chimpanzee, etc.), a domesticated animal (e.g., a dog, cat, horse, etc.), farm animal (e.g., goat, sheep, pig, cattle, etc.), or laboratory animal (e.g., mouse, rat, etc.). Preferably, an organism is a human.

The term "polypeptide," "peptide," "oligopeptide," or "protein" as used herein refers to any composition that includes two or more amino acids joined together by a peptide bond. It may be appreciated that polypeptides can contain amino acids other than the 20 amino acids commonly referred to as the 20 naturally occurring amino acids. Also, polypeptides can include one or more amino acids, including the terminal amino acids, which are modified by any means known in the art (whether naturally or non-naturally). Examples of polypeptide modifications include e.g., by glycosylation, or other post-translational modification. Modifications which may be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Overview

The business methods herein utilize and apply a system that is able to differentiate biological states with reliability, reproducibility, and sensitivity. Additionally, the systems herein can be used to differentiate biological states or conditions with reliability, reproducibility, and sensitivity. The system and methods herein involve the process of obtaining sample from organism(s); preparing the sample(s)—e.g., preferably by denaturing sample component(s); separating components of the sample e.g., using capillary electrophoresis, such that various components travel at various speeds; inputting the samples into a detection device—e.g., a mass spectrometer; and analyzing mass spectra patterns to detect markers that are associated with a particular biological state.

The preparation and separation steps herein can be accomplished using any means known in the art. In some embodiments, either or both the preparation and separation steps occur on a microfluidic device. Such device is preferably disposable. When the methods herein involve the use of a mass spectrometer, a microfluidic device of the invention preferably provides a tip adapted for electrospraying the sample into the mass spectrometer. In some embodiments, the tip is adapted for sheath spraying. In some embodiments, the tip is adapted for non-sheath spraying. In any of the embodiments herein the mass spectrometer may include a disposable inlet capillary.

In one embodiment, the system relies on an integrated, reproducible, sample preparation, separation and electrospray ionization system in a microfluidic format, with high sensitivity mass spectrometry and informatics. These systems can serve as the foundation for the discovery of patterns of markers, including polypeptides, that reflect and differentiate biological states or conditions specific for various states of health, disease, etc.

The present invention relates to systems and methods (including business methods) for identifying unique patterns that can be used for diagnosing a biological state or a condition in an organism, identifying markers based on the patterns, preparing diagnostics based on such markers, and commercializing/marketing diagnostics and services utilizing such diagnostics.

Markers of the present invention may be, for example, any composition and/or molecule or a complex of compositions and/or molecules that is associated with a biological state of an organism (e.g., a condition such as a disease or a non-disease state). A marker can be, for example, a small molecule, a polypeptide, a nucleic acid, such as DNA and RNA, a lipid, such as a phospholipid or a micelle, a cellular component such as a mitochondrion or chloroplast, etc. Markers contemplated by the present invention can be previously known or unknown. For example, in some embodiments, the methods herein may identify novel polypeptides that can be used as markers for a biological state of interest or condition of interest, while in other embodiments, known polypeptides are identified as markers for a biological state of interest or condition.

The systems and methods herein can rely on a microfluidic device, a detection device (e.g., a mass spectrometer), and an informatics tool to provide an integrated, reliable, reproducible, and sensitive analysis of a complex sample mixture. It shall be understood that various aspects of the invention described herein can be applied individually, collectively, or in different combinations with each other.

In some embodiments, the systems and methods herein are used to differentiate biological states or conditions with reliability, reproducibility, and sensitivity. In one embodiment, the system relies on an integrated, reproducible, sample preparation, separation and electrospray ionization system in a microfluidic format, with high sensitivity mass spectrometry and informatics. This system serves as the foundation for the discovery of patterns of markers, such as polypeptides, small molecules, or other biological markers that reflect and differentiate biological states or conditions specific for various states of health and disease. For purposes herein, polypeptides include, e.g., proteins, peptides, and/or protein fragments.

These patterns of markers (e.g., polypeptides) reflect and differentiate biological states or conditions and can be utilized in clinically useful formats and in research contexts. Clinical applications include detection of disease; distinguishing disease states to inform prognosis, selection of therapy, and the prediction of therapeutic response; disease staging; identification of disease processes; prediction of efficacy; prediction of adverse response; monitoring of therapy associated efficacy and toxicity; and detection of recurrence.

Figure 19:
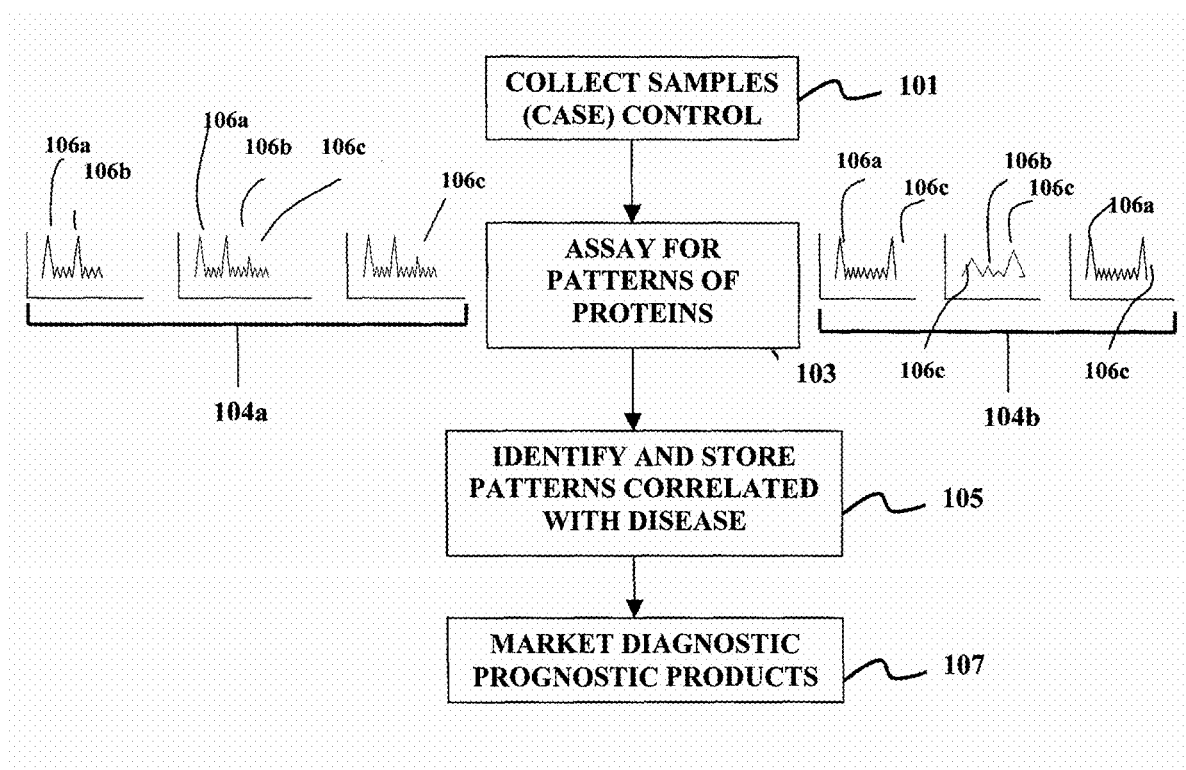
FIG. 19 is an overall flowchart illustrating the operation of one embodiment of the business method.

The system used herein may be utilized in both the applications of studying protein patterns that distinguish case and control samples, and/or in using patterns to diagnose individuals. FIG. 19 illustrates the overall process of the business methods disclosed herein. At step 101 the involved business (alone or with collaborators) collects a representative sample set of case samples and control samples. Case samples are those wherein a patient exhibits a particular biological state or condition, such as, for example, a disease state or other phenotype state. For example, the case samples may be those where a patient exhibits a response to a drug. Conversely, the control samples are collected from patients that do not exhibit the phenotype under study, such as those that do not have the disease or response to a drug.

Preferably more than 10 case and 10 control samples are collected for use or for identifying marker or protein signals of interest. Preferably more than 20 case and 20 control samples, preferably more than 50 case and 50 control samples, preferably more than 100 case and 100 control samples, and most preferably more than 500 case and 500 control samples are collected.

At step 103, the case and control samples are assayed to identify patterns of markers that are present in the case and control samples. In preferred embodiments the markers are polypeptides such as proteins, although they may also include small molecules, nucleic acids, polysaccharides, metabolites, lipids, or the like. Preferably, the patterns are obtained without advance selection or screening of the particular polypeptides involved. In some embodiments, the patterns are obtained without identification of some or all of the markers that are shown in the pattern. Three conceptual patterns are illustrated for cases at 104a and controls at 104b. As shown, the patterns are greatly simplified from those that will be actually observed.

Preferably the assay identifies the presence of more than 100 polypeptides, preferably more than 200 polypeptides, more preferably more than 500 polypeptides, more preferably more than 1000 polypeptides, and more preferably more than 2000 polypeptides. While the identity of some of the polypeptides will be known from prior studies, it is not necessary to specifically identify all of the polypeptides indicated by the assay. Instead, the business takes advantage of the presence of (or absence of) a pattern of many polypeptides repeatedly found to be in the cases in a pattern distinct from the controls. In various embodiments a number of polypeptides are represented in the pattern, but the identity of some of these polypeptides is not known. For example, more than 15 polypeptides can be represented, more than 30 polypeptides can be represented, more than 50 polypeptides can be represented, more than 100 polypeptides can be represented, and more than 1000 polypeptides can be represented The case and control samples are assayed to identify patterns of markers that are present in the case and control samples. In preferred embodiments the markers are polypeptides such as proteins, although they may also include small molecules, nucleic acids, polysaccharides, metabolites, lipids, or the like. Preferably, the patterns are obtained without advance selection or screening of the particular polypeptides involved. In some embodiments, the patterns are obtained without identification of some or all of the markers that are shown in the pattern. Preferably, more than 50%, 55%, 60%, 65%, 70%, 75%, 80%, 85%, 90%, 95%, or 99% markers in a sample are known.

In some embodiments, an assay identifies the presence of more than 100 markers, preferably more than 200, 300, or 400 markers, more preferably more than 500, 600, 700, 800, or 900 markers, more preferably more than 1000, 1100, 1200, 1300, 1400, 1500, 1600, 1700, 1800, 1900 markers, and more preferably more than 2000 markers. Preferably, the assay identified the presence of more than 100 polypeptides, preferably more than 200 polypeptides, more preferably more than 500 polypeptides, more preferably more than 1000 polypeptides, and more preferably more than 2000 polypeptides. While the identity of some of the markers or polypeptides is known from prior studies, it is not used to identify specifically all of the markers or polypeptides indicated by the assay. The presence of (or absence of) a pattern of many markers or polypeptides repeatedly found to be in the cases in a pattern distinct from the controls can be used in the study of phenotypes and/or diagnostics. In various embodiments, a number of markers or polypeptides are represented in the pattern, but the identity of some of these markers or polypeptides is not known. In some embodiments, more than 15 markers can be represented, more than 30 markers can be represented, more than 50 markers can be represented, more than 100 markers can be represented, and more than 1000 markers can be represented. In some embodiments, more than 15 polypeptides can be represented, more than 30 polypeptides can be represented, more than 50 polypeptides can be represented, more than 100 polypeptides can be represented, and more than 1000 polypeptides can be represented.

In any of the embodiments herein, at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000, 1100, 1200, 1300, 1400, 1500 1600, 1700, 1800, 1900, or 2000 markers (e.g., polypeptides) are used to distinguish case individuals from control individuals.

In preferred embodiments, the business relies on a mass spectrometry system to perform the assays. Preferably such systems and methods allow for the capture and measure of many or all of the instances of a marker or polypeptide in a sample that is introduced in the mass spectrometer for analysis. Using such systems it is preferable that one can observe those markers or polypeptides with high information-content but that are only present at low concentrations, such as those "leaked" from diseased tissue. Other high information-content markers or polypeptides may be those that are related to the disease, for instance, those that are generated in the tumor-host environment.

In some embodiments, an early assay, or discovery experiment, such as the first assay, is followed by a later assay. The early assay is normally used in initial identification of markers or polypeptides that identify or separate cases from controls. The later assay is adjusted according to parameters that can focus diagnostics or evaluation of regions of interest, such as regions of high differentiation or variability, i.e. those regions or markers where there are significant differences between case samples and control samples. The parameters can be determined by, for example, an early assay which may identify the regions of interest, which may be on one technology platform, and a later assay on the same or a different platform.

At step 105, bioinformatics system are utilized to identify the differences in patterns, or the polypeptide patterns, in the case and control samples. Such techniques may be proceeded by various data cleanup steps. Patterns can be composed of the relative representation of numerous markers (e.g., polypeptides, other biological entities, small molecules, etc.), the collective profile of which is more important than the presence or absence of any specific entities. By identifying patterns in blood or other patient samples, the methods herein do not only provide the window to the presence of disease and other pathology in some embodiments, but also to the body's ongoing response to the disease or pathologic condition in other embodiments. In a high throughput mode (pipelined system operation), data from a first sample are evaluated in a bio-informatics system at the same time another sample is being processed in a detection device using, for example, a mass spectrometry system.

As shown in the three simplified patterns for "cases" 104*a*, peaks 106*a* and 106*b* tend to be observed in three "case" samples at higher levels. Conversely, less or no signal is observed at peak 106*c* in the three case samples. By contrast, in the control samples 104*b*, peaks 106*a* and 106*c* tend to be observed while peak 106*b* tends to be at low levels. Of course, the patterns shown in FIG. 1 are greatly simplified, and there will be much more complex patterns in actual practice, such as tens, hundreds, or thousands of such peaks. In the particular example illustrated in FIG. 1, peak 106*a* is not informative, while peak 106*b* tends to occur in cases, and peak 106*c* tends to occur in controls. Automated systems will generally be applied in the identification of the patterns that distinguish cases and controls. The measurement of patterns of multiple signals will enable the identification of subtle differences in biological state and make the identification of that state more robust and less subject to biological noise.

At step 107 the business uses the patterns of markers (e.g., polypeptides) present in the sample may be used to identify the disease state of a patient sample in, for example, a diagnostic setting. Samples used in both the steps 101 and 107 can, in preferred embodiments, be serum samples, although tissue or bodily fluid samples from a variety of sources can be used in alternative embodiments. Preferably, though not necessarily, the system used in the diagnostic application is based upon the same technology platform as the platform used to identify the patterns in the first instance. For example, if the platform used to identify the patterns in the first instance is a time of flight (TOF) mass spectrometer, it is preferred that the diagnostic applications of the patterns are run on a time of flight mass spectrometer.

The marketing of the products can take a number of forms. For example, it may be that the developer actually markets the instruments and assays into the diagnostic research market. In alternative embodiments, the developer of the patterns will partner with, for example, a large diagnostic company that will market those products made by the developer, alone or in combination with their own products. In alternative embodiments, the developer of the patterns licenses the intellectual property in the patterns to a third party and derives revenue from licensing income arising from the pattern information.

The business method herein can obtain revenue by various means, which may vary over time. Such sources may include direct sale revenue of products, upfront license fees, research payment fees, milestone payments (such as upon achievement of sales goals or regulatory filings), database subscription fees, and downstream royalties and from various sources including government agencies, academic institution and universities, biotechnology and pharmaceutical companies, insurance companies, and health care providers.

Often, diagnostic services hereunder will be offered by clinical reference laboratories or by way of the sale of diagnostic kits. Clinical reference laboratories generally process large number of patient samples on behalf of a number of care givers and/or pharmaceutical companies. Such reference laboratories in the United States are normally qualified under CLIA and/or CAP regulations. Of course, other methods may also be used for marketing and sales such as direct sales of kits such as FDA or equivalent approved products. In some cases the developer of the pattern content will license the intellectual property and/or sell kits and/or reagents to a reference laboratory that will combine them with other reagents and/or instruments in providing a service.

In the short term, the business methods disclosed generate revenue by, for example, providing application specific research or diagnostic services to third parties to discover and/or market the patterns. Examples of third-parties include customers who purchase diagnostic or research products (or services for discovery of patterns), licensees who license rights to pattern recognition databases, and partners who provide samples in exchange for downstream royalty rights and/or up front payments from pattern recognition. Depending on the fee, diagnostic services may be provided on an exclusive or non-exclusive basis.

Revenue can also be generated by entering into exclusive and/or non-exclusive contracts to provide polypeptide profiling of patients and populations. For example, a company entering clinical trials may wish to stratify a patient population according to, for example, drug regimen, effective dosage, or otherwise. Stratifying a patient population may increase the efficacy of clinical trial (by removing, for example, non responders), thus allowing the company to enter into the market sooner or allow a drug to be marketed with a diagnostic test that identifies patients that may have an adverse response or be non-responsive. In addition, insurance companies may wish to obtain a polypeptide profile of a potential insured and/or to determine if, for example a drug or treatment will be effective for a patient.

In the long term, revenue may be generated by alternative methods. For example, revenue can be generated by entering into exclusive and/or non-exclusive drug discovery contracts with drug companies (e.g., biotechnology companies and pharmaceutical companies). Such contracts can provide for downstream royalties on a drug based on the identification or verification of drug targets (e.g., a particular protein or set of polypeptides associated with a phenotypic state of interest), or on the identification of a subpopulation in which such drug should be utilized. Alternatively, revenue may come from a licensee fee on a diagnostic itself. The diagnostic services, patterns, and tools herein can further be provided to a pharmaceutical company in exchange for milestone payments or downstream royalties. Revenue may also be generated from the sale of disposable fluidics devices, disposable microfluidics devices, or other assay reagents or devices in for example the research market, diagnostic market, or in clinical reference laboratories. Revenue may also be generated from licensing of applications-specific software or databases. Revenue may, still further, be generated based on royalties from technology platform providers who may license some or all of the proprietary technology. For example, a mass-spectrometer platform provider may license the right to further distribute software and computer tools and/or polypeptide patterns.

In preferred embodiments, the mass spectrometer or TOF device utilized herein is coupled to a microfluidic device, such as a separations device. The sample preparation techniques used preferably concentrate the markers (e.g., polypeptides or small molecules) the mass spectrometer is best able to detect and/or are which are most informative, and deplete the ones that are more difficult to detect and/or are less informative (because, for example, they appear in both case and control samples). Prepared samples may then be placed on a microfluidic device, separated and electrosprayed into a mass spectrometer.

In most preferred embodiments the microfluidic separations device is a disposable device that is readily attached to and removed from the mass spectrometer, and sold as a disposable, thereby providing a recurring revenue stream to the involved business and a reliable product to the consumer. Preferably, a mass spectrometer is utilized that accepts a continuous sample stream for analysis and provide high sensitivity throughout the detection process.

Any of the methods and systems herein can be automated to require no manual intervention for at least 1, 2, 3, 4, 5, 6, 7, 8, 9, or more preferably at least 10 hours.

Sample preparation, in some embodiments, includes the removal of high abundance markers or polypeptides, denaturation, removal of markers or polypeptides expected to be in abundance in all samples, addition of preservatives and calibrants, and desalting. These steps allow sensitive measurement of concentrations of information-rich markers, or more preferably information-rich polypeptides, such as those that have leaked from tissue, as compared to markers or polypeptides that would carry little information, such as those highly abundant and native to serum. Prepared samples can then be separated using fast molecular separations methods with high peak capacities. An electrospray-ionization (ESI) interface may be integrated on the microfluidic device (chip), which ionizes and sprays the prepared and separated sample directly into a mass spectrometer and is preferably sold as part of a disposable component to assure that there is no carry-over between samples, and to assure high reliability of the system.

In another embodiment, the system's reproducibility and resolution allows for the differentiation of different levels of markers between case and control samples, even for high abundance components that are not removed by the sample preparation steps. The system resolution allows for the differentiation of modified forms of the components, e.g. modified polypeptides, in which the modification or the level of the modified molecule is the marker.

The microfluidic-based separations preferably provide the marker mixtures and polypeptide mixtures at flow rates and at complexity levels that are matched to the mass spectrometer's optimal performance regions. The mass spectrometer's sensitivity is preferably optimized to detect the species most likely to differentiate between biological states or conditions. Preferably, the reagents used for performing these steps are provided in or along with the microfluidic device, thereby allowing for additional recurring revenue to the involved business and higher performance for the user.

The sample preparation system provides for different operations depending upon the detection device to be utilized. The sample preparation system preferably provides for protein denaturation prior to processing on the mass spectrometer. Analytes of interest herein may be in some cases a protein in a bound form. Preferably the system provides for denaturation of proteins preferably prior to the removal of high abundance materials (such as albumin or other proteins from serum or plasma samples). By denaturing such proteins prior to their removal, bound analytes of interest can be released such that they can be meaningful in later analysis. Denaturation may utilize any of several techniques including the use of heat, high salt concentrations, the use of acids, base, chaotropic agents, organic solvents, detergents and/or reducing agents. Liotta, Lance, A., et al., "Written in Blood," *Nature* (Oct. 30, 2003), Volume 425, page 905. Tirumalai, Radhakrishna S., et al. "Characterization of the Low Molecular Weight Human Serum Proteome," *Molecular & Cellular Proteomics* 2.10 (Aug. 13, 2003), pages 1096-1103.

The system used for removal of high abundance markers (e.g., polypeptides) may be based on, for example, the use of high affinity reagents for removal of the markers (e.g., polypeptides), the use of high molecular weight filters, ultracentrifugation, precipitation, and/or electrodialysis. Polypeptides that are often be removed include, for example, those involved in normal metabolism, and a wide variety of other indications not of relevance to a particular assay. Such markers or proteins may be removed through, for example, a solid phase extraction resin or using a device that removes such proteins with antibodies (e.g., Agilent's High-Capacity Multiple Affinity Removal System). Additionally, the system may include a reversed phase chromatography device, for example, for separation or fractionation of small molecules and/or to trap, desalt, and separate or fractionate a marker or protein mixture.

FIG. 1 illustrates additional aspects of an exemplary system platform used herein. The invention involves an integrated system to a) discover; and b) assay patterns of markers including polypeptides that reflect and differentiate biological and clinical states of organisms, including patients, in biological materials including but not limited to body fluids.

Biological and clinical states include but are not limited to phenotypic states; conditions affecting an organism; states of development; age; health; pathology, disease detection, process, or staging; infection; toxicity; or response to chemical, environmental, or drug factors (such as drug response phenotyping, drug toxicity phenotyping, or drug effectiveness phenotyping).

Biological fluids 201 include but are not limited to serum, plasma, whole blood, nipple aspirate, ductal lavage, vaginal fluid, nasal fluid, ear fluid, gastric fluid, pancreatic fluid, trabecular fluid, lung lavage, urine, cerebrospinal fluid, saliva, sweat, pericrevicular fluid, semen, prostatic fluid, and tears.

The system provides for the integration of fast molecular separations and electrospray ionization system 204 on a microfluidic platform 203. The system provides processed samples to a high sensitivity time of flight mass spectrometer 205. Signal processing system and pattern extraction and recognition tools 207 incorporate domain knowledge to extract information from polypeptide patterns and classify the patterns to provide a classification 209. The signal processing system may include or be coupled to other software elements as well. For example, the signal processing system may provide for an easy to use user interface on the associated computer system and/or a patient database for integration of results into an institution's laboratory or patient information database system.

The microfluidic device(s) 203 and 204 may be formed in plastic by means of etching, machining, cutting, molding, casting or embossing. The microfluidic device(s) may be made from glass or silicon by means of etching, machining, or cutting. The device may be formed by polymerization on a form or other mold. The device may be made from a polymer by machining, cutting, molding, casting, or embossing. The molecular separations unit or the integrated fast molecular separations/electrospray ionization unit may provide additional sample preparation steps, including sample loading, sample concentration, removal of salts and other compounds that may interfere with electrospray ionization, removal of highly abundant species, selective capture of specific molecules, with affinity reagents concentration of the sample to a smaller volume, proteolytic or chemical cleavage of components within the biological material, enzymatic digestion, and/or aliquoting in to storage containers. The particular operations performed by the device depend upon the detection technology that is utilized.

The device(s) for separations and electrospray may be either single use for a single sample, multi-use for a single sample at a time with serial loading, single use with parallel multiple sample processing, multi-use with parallel multiple sample processing or a combination. Separations processes may include isoelectric focusing, electrophoresis, chromatography, or electrochromatography. The separations device may include collection areas or entities for some or all of the purified or partially purified fractions.

It is to be understood that the inventions herein are illustrated primarily with regard to mass spectrometry as a detection device, but other devices may be used alone or with the mass spectrometer. For example, detection devices may include electrochemical, spectroscopic, or luminescent detectors, and may be integral with the microfluidics device.

Mass spectrometers that may be used include quadrupole, ion trap, magnetic sector, orbitrap Fourier transform ion cyclotron resonance instruments, or an orthogonal multiplex time-of-flight mass spectrometer which includes an analyzer that receives an ion beam from an electrospray ionization (ESI) source.

Figure 20:
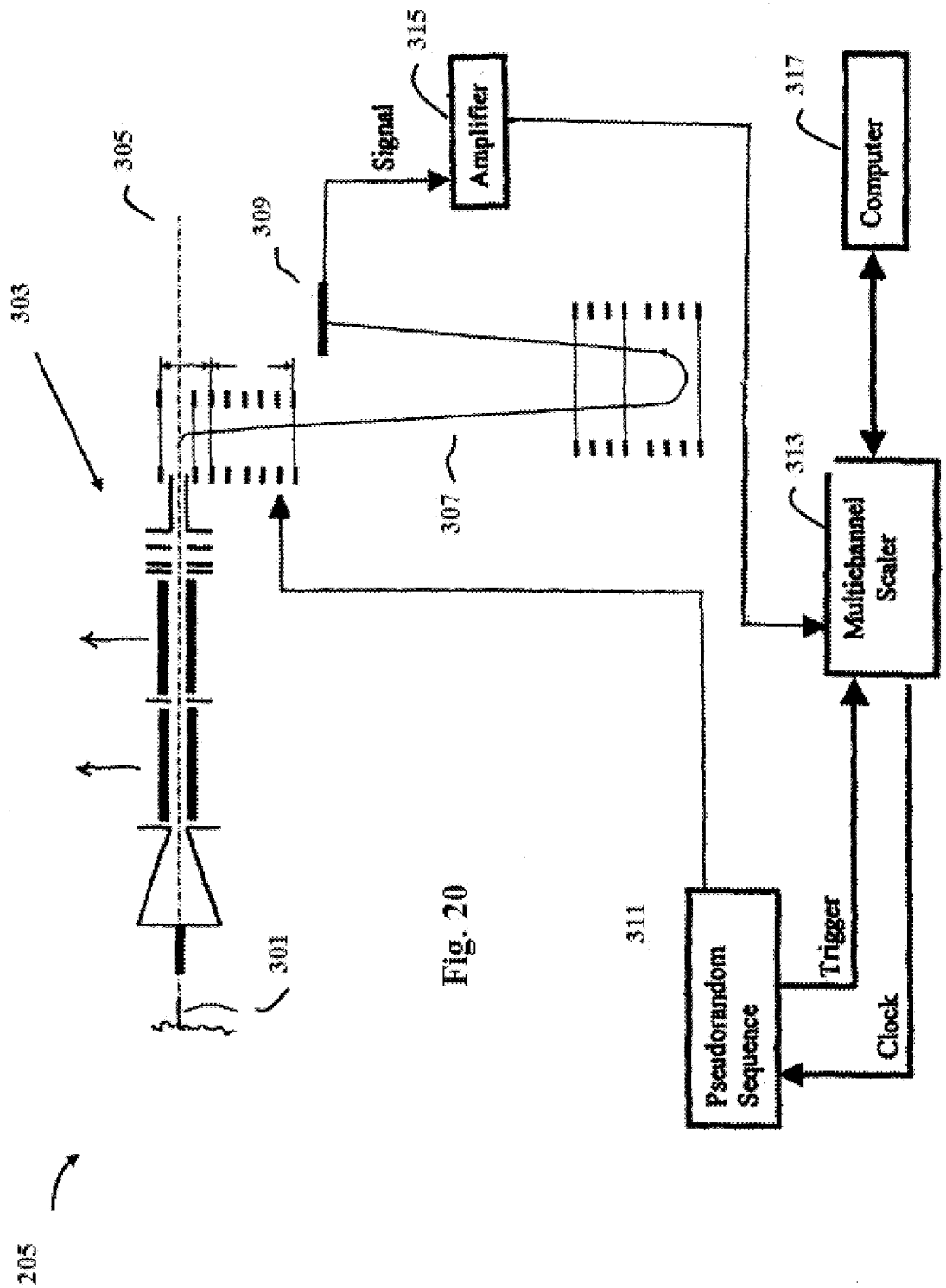
FIG. 20 illustrates one mass spectrometer that may be used herein.

FIG. 20 illustrates a mass spectrometer system 205 in greater detail in one specific embodiment of the invention. In FIG. 20, an orthogonal multiplex time-of-flight mass spectrometer which includes an analyzer that receives an ion beam from an electrospray ionization (ESI) source 301 such as disclosed in U.S. Ser. No. 10/395,023. By "multiplex" in this context it is intended to mean a system that processes multiple ion packets at the same time. The ion beam is initially introduced into analyzer 303 along an axis 305, and the analyzer generally accumulates differing size packets of ions of the beam and accelerates the packets of ions laterally along a flight path 307. The pulses or packets of ions are spaced in time and along the flight path by different accumulation periods, and the speed of travel of the ions along flight path 307 varies with a mass-to-charge ratio (m/z) such that the ions of sequential pulses, and often the ions of three or more pulses, will arrive intermingled at one time at a detector 309.

In addition to analyzer 303, the system includes a driver 311 to intermittently energize lateral acceleration electrodes of analyzer 303. Driver 311 modulates or encodes the beam with the pseudorandom sequence by reference to a clock signal supplied from a multichannel scaler 313. Driver 311 also supplies a trigger signal to the multichannel scaler 313 to signal the start of a sequence. An output signal from detector 309 is amplified by an amplifier 315 and is counted by multichannel scaler 313.

The pseudorandom sequence applied by driver 311 will typically provide for time periods which may each be defined as integer multiples of a unit accumulation time. To facilitate reconstruction of a spectrum from the signal generated by detector 309, multichannel scaler 313 may count the amplified signal from amplifier 315 into time bins which represent integral fractions of this unit time. These counts can then be sent to a computer 317 for reconstruction of a particular spectra and characterization of the sample material introduced into the system via ESI source 301.

Computer 317 may also control a variety of additional components of system 205, with a wide variety of alternative data processing being possible. The structure and use of driver 311, multichannel scaler 313, amplifier 315 and computer 317 may in some embodiments be those such as shown in U.S. Pat. No. 6,300,626 issued to Brock et al. and entitled "Time-of-Flight Mass Spectrometer and Ion Analysis" on Oct. 9, 2001, which is fully incorporated by reference along with all other references cited in this application.

In preferred embodiments the system also adapts the speed of the system in response to the detection of known markers that are likely to be present in all samples, and which are readily detectable. Since separations may often vary in retention or migration time, by detecting molecules that are known, likely to be in all samples, and easily detectable, and then comparing the speed at which they have passed through the system in comparison to a standard from other experiments, it becomes possible to speed the system up by speeding the separations in response to the detection of slower than expected migration time, or slowing the system down in response to faster than expected migration times. The speed may be adjusted through, for example, adjustments in system pressure, voltage, current flow, or temperature. Preferably, the system is operated faster or slower by changing the voltage. Thus the speed of the system can be fine tuned to detect specific markers.

Representative markers (e.g., peptides and proteins) that could be spiked into samples for quality control include neurotensin, lysozyme, aprotinin, insulin b-chain, and renin substrate. In addition, the speed of operation of the device may be slowed to provide greater accuracy in the detection of molecules of particular interest in a spectrum. Conversely, the system may be operated more quickly during the times when components of low interest would be expected to be detected.

In some embodiments pressure is added to move the components through the electrophoretic device, especially to migrate components to the end of an electrophoretic separation capillary (in conjunction with the use of the electro osmotic flow). The pressure produces buffer flow that is used to maintain a stable electrospray.

Ions formed by electrospray ionization may be singly or multiply charge ions of molecules, with charge coming from protons or alkali metal bound to the molecules. Ion excitation may be produced by collision of ions with background gas or an introduced collision gas. Alternatively, excitation may be from collision with other ions, a surface, interaction with photons, heat, electrons, or alpha particles. Through excitation of the sample in an electrospray the information content of the process should be altered and/or enhanced. Such excitation may, for example, desolvate ions, dissociate noncovalently bound molecules from analyte ions, break up solvent clusters, fragment background ions to change their mass to charge ratio and move them to a ratio that may interfere less with the analysis, strip protons and other charge carriers such that multiply charged ions move to different regions of the spectrum, and fragment analyte ions to produce additional, more specific or sequence-related information.

In preferred embodiments the excitation system may be turned on and off to obtain a set of spectra in both states. The information content of the two spectra is, in most cases, far greater than the information content of either single spectra. In such embodiments the system includes a switching device for activating and de-activating the excitation/ionization system. Analysis software is configured in this case to analyze the sample separately both in the "on" state of the excitation system and in the "off" state of the excitation system. Different markers may be detected more efficiently in one or the other of these two states.

Figure 2:
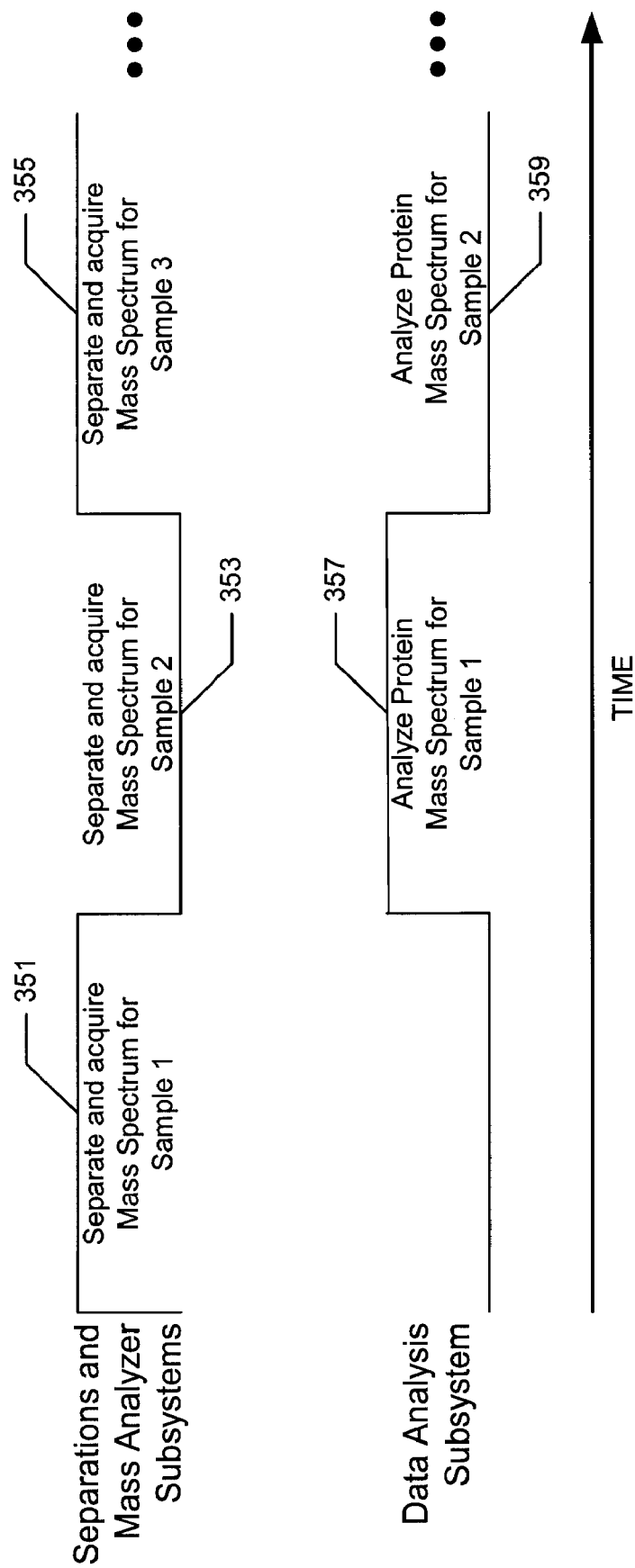
FIG. 2 illustrates a timing diagram showing operation of a parallel system.

FIG. 2 illustrates the pipelined systems operations in greater detail. As shown at step 351, a first sample is acquired during this time frame and separated in the microfluidics device, and then processed in the mass spectrometer. At step 353 a second sample is processed in the microfluidics device and processed in the mass spectrometer. During at least some of the time when second sample is being processed at step 353, the data from the mass spectrum for the first sample are processed in the data analysis system at step 357. Similarly, at step 355 a third sample is processed in the microfluidics device and the mass spectrometer, while the data from sample 2 are being analyzed in the data analysis system at step 359.

Sample Collection

In some embodiments, the system and methods (including business methods) herein involve obtaining sample(s) from organism(s) as is illustrated in FIG. 1, element 201. Preferably the organism is a human. Such samples can be in liquid or non-liquid form.

Examples of liquid samples that can be obtained from an organism, such as a patient, include, but are not limited to, serum, plasma, whole blood, nipple aspirate, ductal lavage, vaginal fluid, nasal fluid, ear fluid, gastric fluid, pancreatic fluid, trabecular fluid, lung lavage, urine, cerebrospinal fluid, saliva, sweat, pericrevicular fluid, semen, prostatic fluid, and tears.

Examples of non-liquid samples include samples from tissue, bone, hair, cartilage, tumor cells, etc. Non-liquid samples may be dissolved in a liquid medium, containing, e.g., detergent, chaotrope, denaturant, acid, base, protease or reducing agent prior to further analysis.

In preferred embodiments, samples collected are in liquid form. Preferably, samples collected are serum or plasma.

Case samples are obtained from individuals with a particular phenotypic state of interest. Examples of phenotypic states include, phenotypes resulting from an altered environment, drug treatment, genetic manipulations or mutations, injury, change in diet, aging, or any other characteristic(s) of a single organism or a class or subclass of organisms. In a preferred embodiment, a phenotypic state of interest is a clinically diagnosed disease state. Such disease states include, for example, cancer, cardiovascular disease, inflammatory disease, autoimmune disease, neurological disease, infectious disease and pregnancy related disorders. Control samples are obtained from individuals who do not exhibit the phenotypic state of interest or disease state (e.g., an individual who is not affected by a disease or who does not experience negative side effects in response to a given drug). Alternatively, states of health can be analyzed.

Cancer phenotypes are studied in some aspects of the invention or business method. Examples of cancer include, but are not limited to: breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non-small cell lung carcinoma gallstones, islet cell tumor, primary brain tumor, acute and chronic lymphocytic and granulocytic tumors, hairy-cell tumor, adenoma, hyperplasia, medullary carcinoma, pheochromocytoma, mucosal neurons, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Cardiovascular disease may be studied in other applications of the invention. Examples of cardiovascular disease include, but are not limited to, congestive heart failure, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic night ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol embolism, Wallenberg syndrome, Hippel-Lindau disease, and telangiectasis.

Inflammatory disease and autoimmune disease may be studied in other applications of the system or business method. Examples of inflammatory disease and autoimmune disease include, but are not limited to, rheumatoid arthritis, non-specific arthritis, inflammatory disease of the larynx, inflammatory bowel disorder, psoriasis, hypothyroidism (e.g., Hashimoto thyroidism), colitis, Type 1 diabetes, pelvic inflammatory disease, inflammatory disease of the central nervous system, temporal arteritis, polymyalgia rheumatica, ankylosing spondylitis, polyarteritis nodosa, Reiter's syndrome, scleroderma, systemis lupus and erythematosus.

Infectious disease may be studied in still further aspects of the system or business method. Examples of infectious disease include, but are not limited to, AIDS, hepatitis C, SARS, tuberculosis, sexually transmitted diseases, leprasy, lyme disease, malaria, measles, meningitis, mononucleosis, whooping cough, yellow fever, tetanus, arboviral encephalitis, and other bacterial, viral, fungal or helminthic diseases.

Neurological diseases include dementia, Alzheimer disease, Parkinsons disease, ALS, MS.

Pregnancy related disorders include pre-eclampsia, eclampsia pre-term birth, growth restriction in utero, rhesus incompartability, retained placenta, septicemia, separation of the placenta, ectopic pregnancy, hypermosis gravidarum, placenta previa, erythroblastosis fetalis, pruritic urticarial papula and plaques.

Samples may be collected from a variety of sources in a given patient depending on the application of the business. In some embodiments samples are collected on the account of the company itself while in other examples they are collected in collaboration with an academic collaborator or pharmaceutical collaborator that, for example, is collecting samples in a clinical trial. Samples collected are preferably bodily fluids such as blood, serum, sputum, including, saliva, plasma, nipple aspirants, synovial fluids, cerebrospinal fluids, sweat, urine, fecal matter, pancreatic fluid, trabecular fluid, cerebrospinal fluid, tears, bronchial lavage, swabbings, bronchial aspirants, semen, precervicular fluid, vaginal fluids, pre-ejaculate, etc. In a preferred embodiment, a sample collected is approximately 1 to 5 ml of blood.

In some instances, samples may be collected from individuals over a longitudinal period of time (e.g., once a day, once a week, once a month, biannually or annually). The longitudinal period may, for example, also be before, during, and after a stress test or a drug treatment. Obtaining numerous samples from an individual over a period of time can be used to verify results from earlier detections and/or to identify an alteration in polypeptide pattern as a result of, for example, aging, drug treatment, pathology, etc. Samples can be obtained from humans or non-humans. In a preferred embodiment, samples are obtained from humans.

When obtaining a blood, serum, or plasma sample, a coagulation cascade may activate proteases that can induce clotting and cleave proteins in the sample. Preferably, such processes can be prevented or their effect reduced. Thus for serum samples, separating clots from the serum as soon as the clotting process is completed, then freezing the serum as quickly as possible but no longer than within 24 hrs, 12 hrs, 6 hrs, 3 hrs or 1 hr. Similarly for plasma samples, the present invention contemplates removing cells quickly from the blood sample (e.g., in less than 24 hrs, 12 hrs, 6 hrs, 3 hrs, or 1 hr) and the plasma is frozen as soon as possible. Preferred protocols for sample collection and storage are given in Table 1 below.

TABLE 1

Recommended protocols for blood collection and storage.

| Process Step | Serum | Plasma |
| --- | --- | --- |
| Tube type | Plastic serum separator tube (Plus SST) | $K_2$EDTA |
| Clotting time and temp | 30-45 min at room temperature | N/A |
| Centrifuge | 10 min at 1100-1300 g at room temperature | Within 30 min of venipuncture centrifuge for 15 min at 2500 g at room temperature |
| Aliquot and Freezing | 0.5 mL aliquots to cryovials, and refrigerated until frozen at −80° C., within 2 hours of venipuncture. | 0.5 mL aliquots to cryovials, and refrigerated until frozen at −80° C., within 2 hours of venipuncture. |

Sample Preparation

After samples are collected, they are optionally prepared and/or separated before they are analyzed. Sample preparation and separation can involve any of the following procedures, depending on the type of sample collected and/or types of marker or protein searched: removal of high abundance markers or polypeptides (e.g., albumin, and transferring; addition of preservatives and calibrants, denaturation, desalting of samples; concentration of sample markers and/or polypeptides; selective capture of specific molecules with affinity reagents; protein digestions; and fraction collection. Further disruption of proteolytic processes by adding protease inhibitors to blood collection tubes or tubes used to store or prepare the blood is also used in some embodiments.

Examples of protease inhibitors that may be added to a blood, plasma or serum sample include but are not limited to acid protease inhibitors, serine protease inhibitors, threonine protease inhibitors, cysteine protease inhibitors, aspartic acid protease inhibitors, metallo protease inhibitors, and glutamic acid protease inhibitors. Examples of common serine protease inhibitors include alpha 1-antitrypsin, complement 1-inhibitor, antithrombin, alpha 1-antichymotrypsin, plasminogen activator inhibitor 1 (coagulation, fibrinolysis) and neuroserpin. In preferred embodiments, a protease inhibitor is an acid protease inhibitor, or more preferably, Pepstatin A. Other examples of acid protease inhibitors include Ahpatinins, In some embodiment, sample preparation may involve denaturation or the addition of an added solution to the sample.

Exemplary steps for sample preparation are given in Table 2 below:

TABLE 2

Sample preparation procedure.

| | |
|---|---|
| (i) | Dilute 50 µL serum to 500 µL in 1% formic acid, 1 µM pepstatin, 300 nM angiotensin III, 1 µM aprotinin |
| (ii) | Centrifuge through 50 kDa ultrafiltration membranes (30 min., 14,000 × g) |
| (iii) | Apply to activated reverse phase resin in 96 well plate (Waters µElute plate) - on a vacuum manifold |
| (iv) | Wash (desalt) and then elute (70% ACN, 0.1% acetic) Dry under N2 stream |
| (v) | Redissolve each well with 5 µL 20% IPA, 0.1% formic acid, 3 µM renin substrate, 3 µM bradykin, using two minute vortexing |
| (vi) | Freeze @ −20° C. until analysis |

Figure 3:
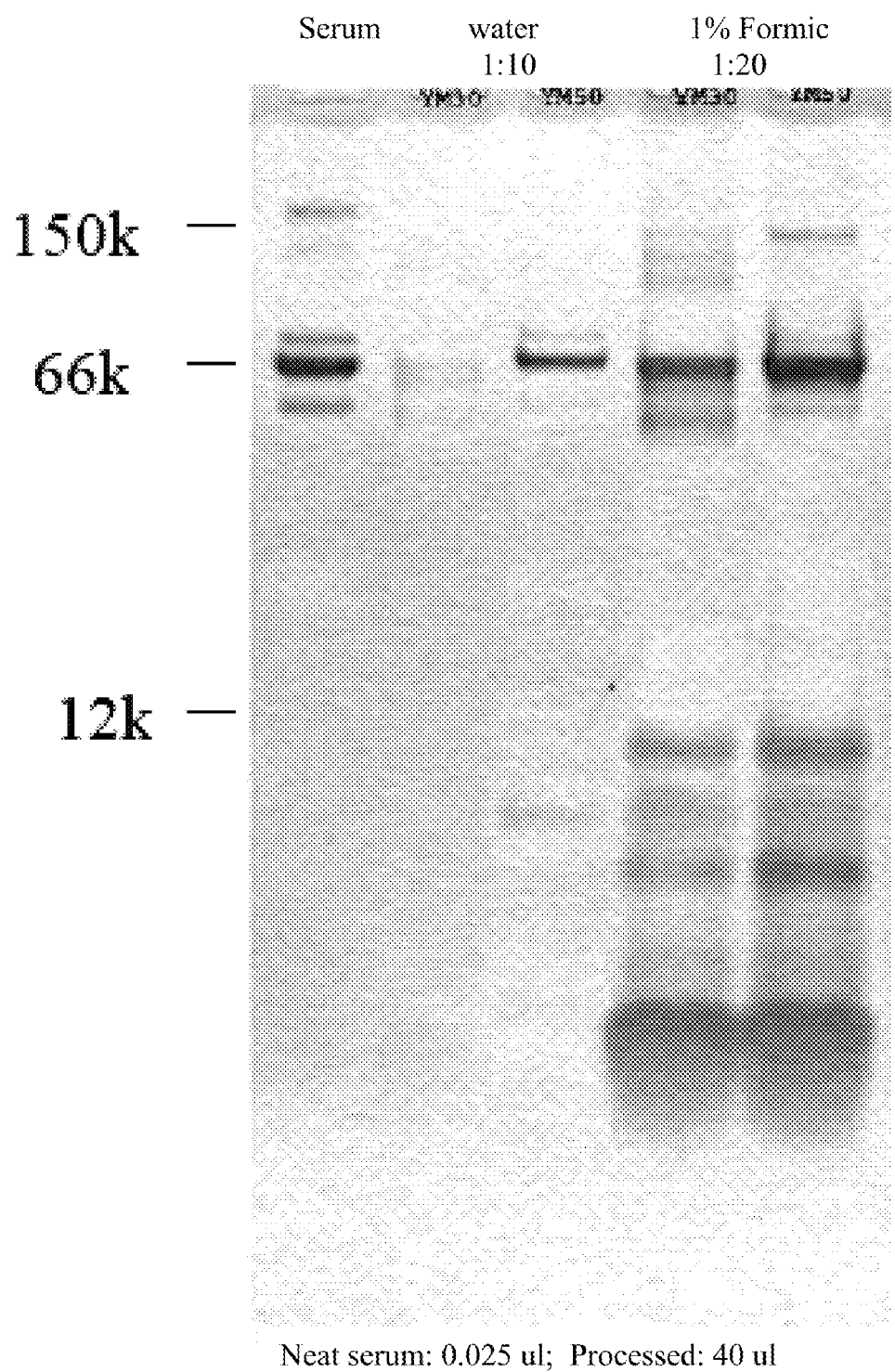
FIG. 3 illustrates an SDS PAGE gel of serum with and without denaturation of serum with acid prior to ultrafiltration. Lane 1 of FIG. 3 is 0.025 µL of unprocessed serum; Lane 2 of FIG. 3 is 40 µL serum diluted 1:10 with water, passed thru 30 kD MWCO membrane; Lane 3 of FIG. 3 is 40 µL serum diluted 1:10 with water, passed through 50 kD MWCO membrane; Lanes 4 of FIG. 3 is 40 µL serum diluted 1:10 with 1% formic acid, passed thru 30 kD MWCO membrane, Lane 5 of FIG. 3 is 40 µL serum diluted 1:10 with 1% formic acid, passed through 50 kD MWCO membrane.

FIG. 3 illustrates the efficiency of the sample preparation method for removal of high MW components and recovery of low MW components. Total protein measurement on serum before preparation by denaturation (70 mg/nL) and after preparation by denaturation using an acid (70 ug/nL) followed by ultrafiltration released a significant amount of lower molecular weight components. In particular, FIG. 3 shows an SDS PAGE gel of serum with and without denaturation of serum with acid prior to ultrafiltration. Lane 1 of FIG. 3 illustrates protein from 0.025 µL of unprocessed serum. Lane 2 of FIG. 3 illustrates protein from 40 µL serum diluted 1:10 with water, passed thru 30 kD MWCO membrane. Lane 3 of FIG. 3 illustrates 40 µL serum diluted 1:10 with water, passed through 50 kD MWCO membrane. Lanes 4 of FIG. 3 illustrates 40 µL serum diluted 1:10 with 1% formic acid, passed thru 30 kD MWCO membrane. Lane 5 of FIG. 3 illustrates 40 µL serum diluted 1:10 with 1% formic acid, passed through 50 kD MWCO membrane.

FIG. 3 demonstrates that about 99% of polypeptides were depleted by denaturation prior to separation by ultrafiltration. Recovery of representative polypeptides averaged 65%, demonstrating the efficiency of low MW peptide recovery.

Additional examples on the use and effects of protease inhibitors on sample analysis are discussed herein.

Figure 9:
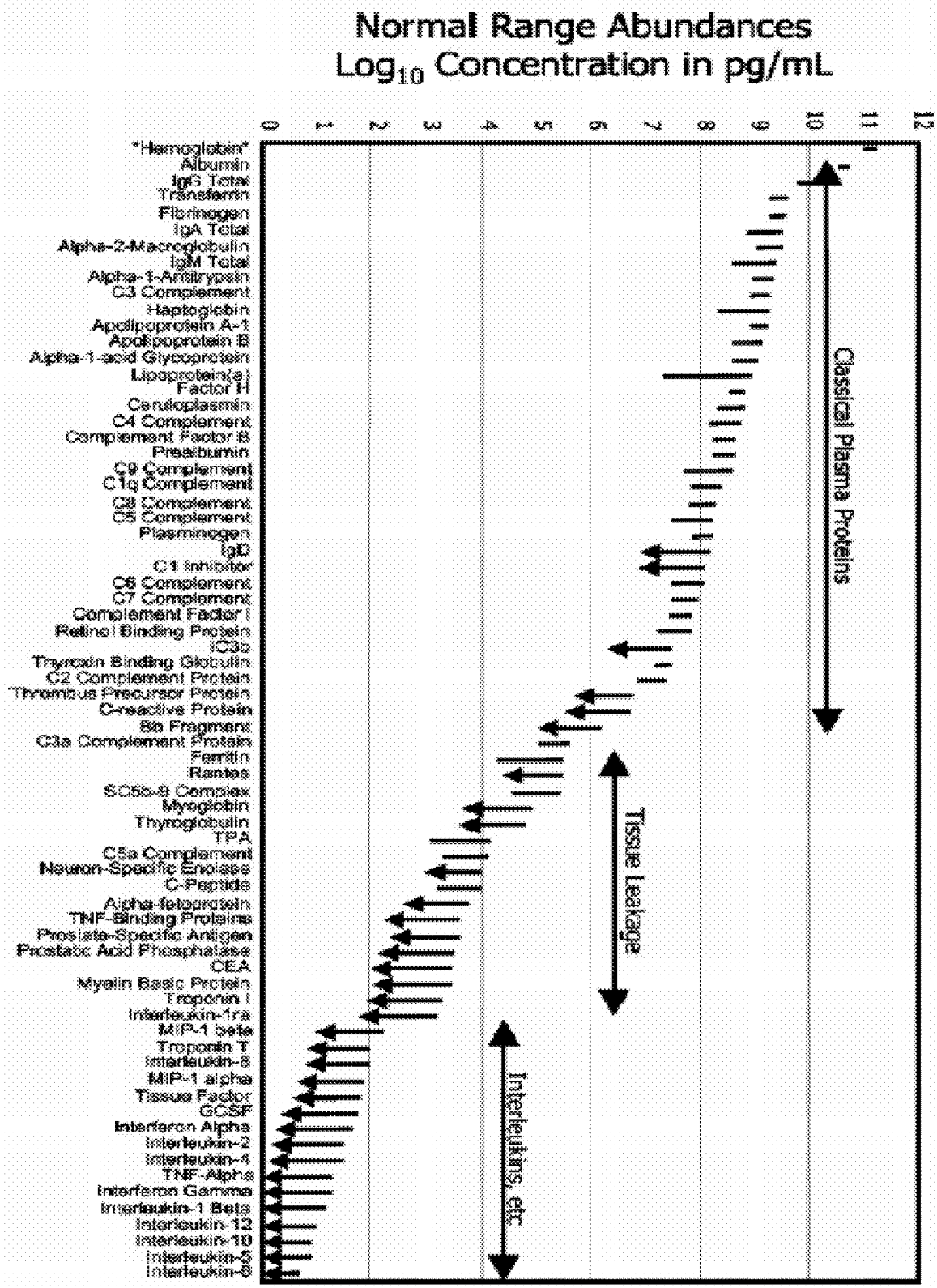
FIG. 9 illustrates various range abundances of various components in serum. Classical plasma proteins are high abundance components that are preferably removed from a sample prior to analysis.

Preferably, sample preparation techniques concentrate information-rich markers or polypeptides (e.g., polypeptides that have "leaked" from diseased cells or are produced by the host response to the tumor) and deplete markers and/or polypeptides that would carry little or no information such as those that are highly abundant or native to serum (e.g., classical plasma proteins such as albumin). FIG. 9 illustrates range abundances of various components/markers in serum. Classical plasma proteins that are highly abundant are preferably removed from a sample prior to analysis.

Sample preparation can take place in a manifold or preparation/separation device. In preferred embodiment, such preparation/separation device is a microfluidic device. Optimally, the preparation/separation device interfaces directly or indirectly with a detection device. In another embodiment, such preparation/separation device is a fluidics device. In yet another embodiment, the preparation device is a 96-well plate and the separation device is a microfluidic device.

In other preferred embodiments, sample preparation uses conventional methods (e.g., pipettes and 96 well plates, while separation takes place on a microfluidic device.

Approximately 100 µL of a sample or less is analyzed per assay in some particular embodiments of the invention. Removal of undesired markers or polypeptides (e.g., high abundance, uninformative, or undetectable polypeptides) can be achieved using, e.g., high affinity reagents, high molecular weight filters, size exclusion, untracentrifugation and/or electrodialysis.

High Affinity Reagents

High affinity reagents include antibodies or aptamers that selectively bind to high abundance polypeptides or reagents that have a specific pH, ionic value, or detergent strength. Examples of high affinity reagents that can be used to remove high abundant, or informatics depleted components from a sample include antibodies and aptamers that selectively bind to such components (e.g., polypeptide, reagents, etc.). For example, albumin may be removed by specific antibodies (Pieper, R., et al. (2003) Proteomics 3, 422-32), dyes (e.g. Cibachron Blue), synthetic peptides, and aptamers. Immunoglobulins (e.g., IgG) can readily bind Protein A and Protein G. Other antibody reagents are also available for removal of abundant proteins (e.g., Agilent's High-Capacity Multiple Affinity Removal System). In preferred embodiments, a device that removes the highest abundance proteins, such as Agilent's device, is utilized to remove a high abundant protein.

High Molecular Weight Filters

High molecular weight filters include membranes that separate molecules on the basis of size and molecular weight. Such filters may further employ reverse osmosis, dialysis, nanofiltration, ultrafiltration and microfiltration.

Examples of high molecular weight filters that can be used to remove undesired components from a sample include membranes that separate molecules on the basis of size and molecular weight. Such membranes may further employ reverse osmosis, dialysis, nanofiltration, ultrafiltration and microfiltration. In some embodiments high molecular weight filters separate out all components that have molecular weight greater than 1,000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, 1 kD.

Ultracentrifugation

Ultracentrifugation is another method for removing undesired components of a sample. Ultracentrifugation can involve centrifugation of a sample at least about 10,000 rpm, 20,000 rpm, 30,000 rpm, 40,000 rpm, 50,000 rpm, 60,000 rpm, 70,000 rpm, 80,000 rpm, 90,000 rpm, or 100,000 rpm while monitoring with an optical system the sedimentation (or lack thereof) of particles.

Electrodialysis

Another method for removing undesired components is via electrodialysis. Electrodialysis is an electromembrane process in which ions are transported through ion permeable membranes from one solution to another under the influence of a potential gradient. Since the membranes used in electrodialysis have the ability to selectively transportions having positive or negative charge and reject ions of the opposite charge, electrodialysis is useful for concentration, removal, or separation of electrolytes.

In a preferred embodiment, the manifold or microfluidic device performs electrodialysis to remove high molecular weight markers and polypeptides or undesired markers and polypeptides. Electrodialysis is first used to allow only molecules under approximately 30 kD (not a sharp cutoff) to pass through into a second chamber. A second membrane with a very small molecular weight (roughly 500 D) allows smaller molecules such as salts to egress the second chamber.

In some embodiments, electrodialysis is used to allow only molecules under approximately 10 kDa, 20 kDa, 30 kDa, 40 kDa, 50 kDa, 60 kDa, 70 kDa, 80 kDa, 90 kDa, 100 kDa to pass through from a first chamber into a second chamber. A second membrane with a very small molecular weight, e.g., less than 900 Da, 800 Da, 700 Da, 600 Da, 500 Da, 400 Da, 300 Da, 200 Da, or 100 Da, allows smaller molecules such as salts to egress the second chamber.

Size Exclusion

Another method for separating molecules by molecular weight is size exclusion chromatography also called gel-permeation chromatography (GPC). Size exclusion chromatography uses porous particles to separate molecules of different sizes. In size exclusion chromatography, molecules can flow past a porous resin or be entrapped or entrained in a porous resin. Thus, molecules that are smaller than the pore size can enter the particles and therefore have a longer path and longer transit time than larger molecules that cannot enter the particles. The low molecular weight molecules are collected by passing additional solution over the resin of particles.

In some of the embodiments herein, depletion of high abundance markers such as proteins occurs based on size. For example, in one embodiments polypeptides>1,000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, 1 kD) are removed. More preferably polypeptides>50 kD, 49 kD, 48 kD, 47 kD, 46 kD, 45 kD, 44 kD, 43 kD, 42 kD, 41 kD, 40 kD, 39 kD, 38 kD, 37 kD, 36 kD, 35 kD, 34 kD, 33 kD, 32 kD, 31 kD, 30 kD, 29 kD, 28 kD, 27 kD, 26 kD, 25 kD, 24 kD, 23 kD, 22 kD, 20 kD, 19 kD, 18 kD, 17 kD, 16 kD, 15 kD, 14 kD, 13 kD, 12 kD, 11 kD, 10 kD, 9 kD, 8 kD, 7 kD, 6 kD, 5 kD, 4 kD, 3 kD, 2 kD, or 1 kD are removed. Preferably greater than 10%, 20%, 30%, 40%, 50%, 60%, 70%, 80%, 90%, 95%, 99% of such proteins with the above molecular weight are removed. In other embodiments, depletion of high abundance markers occurs based on binding specificity (e.g., using antibodies).

In one example, sample preparation including denaturation of components (e.g., polypeptides) occurs prior to detection of the sample by a detection device. More preferably, denaturation of markers occurs prior to removal of one or more high abundance materials. By denaturing such markers prior to their removal, bound analytes of interest are released such that they can be meaningful in later analysis. Denaturation may involve any technique known in the art including, for example, the use of heat, high salt concentrations, the use of acids, base, chaotropic agents, organic solvents, detergents and/or reducing agents. Liotta, Lance, A., et al., *Nature* (Oct. 30, 2003), Volume 425, page 905; Tirumalai, Radhakrishna S., et al. "Characterization of the Low Molecular Weight Human Serum Proteome," *Molecular & Cellular Proteomics* 2.10 (Aug. 13, 2003), pages 1096-1103.

In one embodiment, denaturation occurs prior to filtration with a high-molecular weight filter. This allows for the disassociation of low molecular weight components from large protein complexes. Following size separation, the filtrate (low MW composition) may be concentrated and desalted with a reverse phase resin in a solid phase extraction (SPE) format.

Sample Separation

After samples are prepared, markers including polypeptides of interest may be separated or fractionated. Separation or fractionation can take place in the same location (manifold or microfluidic device) as the preparation or in another location. In a preferred embodiment, separation occurs in the same microfluidic device where preparation occurs, but in a different location on the device. Samples can be removed from an initial manifold location to a microfluidic device using various means, including an electric field. In one embodiment, the samples are concentrated during their migration to the microfluidic device using reverse phase beads and an organic solvent elution such as 50% methanol. This elutes the molecules into a channel or a well on a separation device of a microfluidic device. In another embodiment, samples are concentrated by isotachophoresis, in which ions are concentrated at a boundary between a leading and a trailing electrolyte of lower and higher electrophoretic mobilities, respectively. In other embodiments, sample preparation occurs or sample fractionation using conventional methods (e.g., pipettes and 96-well plates) and samples are then transferred to a microfluidic device for separations.

Separation can involve any procedure known in the art, such as capillary electrophoresis (e.g., in capillary or on a chip/microfluidic device), or chromatography (e.g., in capillary, column or on a chip/microfluidic device).

(i) Electrophoresis

Electrophoresis separates ionic molecules such as polypeptides by differential migration patterns through an open capillary or open channel or a gel based on the size and ionic charge of the molecules in an electric field. Electrophoresis can be conducted in a gel, capillary or on a chip. Examples of capillaries used for electrophoresis include capillaries that interface with an electrospray tip.

Capillary Gel Electrophoresis (CGE) separates ionic molecules through a gel. Examples of gels used for electrophoresis include starch, acrylamide, agarose or combinations thereof. In a preferred embodiment, polyacrylamide gels are used. A gel can be modified by its cross-linking, addition of detergents, immobilization of enzymes or antibodies (affinity electrophoresis) or substrates (zymography) and pH gradient. Examples of capillaries used for electrophoresis include capillaries that interface with an electrospray.

Capillary electrophoresis (CE) is preferred for separating complex hydrophilic molecules and highly charged solutes. Advantages of CE include its use of small samples (sizes ranging from 0.001 to 10 μL), fast separation, easily reproducible, and the ability to be coupled to a mass spectrometer. CE technology uses narrow bore fused-silica capillaries to separate a complex array of large and small molecules. High voltages are used to separate molecules based on differences in charge, size and hydrophobicity. Depending on the types of capillary and buffers used, CE can be further segmented into separation techniques such as capillary zone electrophoresis (CZE), capillary isoelectric focusing (CLEF) and capillary electrochromatography (CEC).

Capillary zone electrophoresis (CZE), also known as free-solution CE (FSCE), is the simplest form of CE. The separation mechanism of CZE is based on differences in the size and charge of the analytes. Fundamental to CZE are homogeneity of the buffer solution and constant field strength throughout the length of the capillary. The separation relies principally on the pH-controlled dissociation of acidic groups on the solute or the protonation of basic functions on the solute.

Capillary isoelectric focusing (CIEF) allows amphoteric molecules, such as polypeptides, to be separated by electrophoresis in a pH gradient generated between the cathode and anode. A solute migrates to a point where its net charge is zero. At this isoelectric point (the solute's pI), migration stops and the sample is focused into a tight zone. In CIEF, once a solute has focused at its pt, the zone is mobilized past the detector by either pressure or chemical means.

CEC is a hybrid technique between traditional liquid chromatography (HPLC) and CE. In essence, CE capillaries are packed with HPLC packing and a voltage is applied across the packed capillary, which generates an electro-osmotic flow (EOF). The EOF transports solutes along the capillary towards a detector. Both differential partitioning and electrophoretic migration of the solutes occurs during their transportation towards the detector, which leads to CEC separations. It is therefore possible to obtain unique separation selectivities using CEC compared to both HPLC and CE. The beneficial flow profile of EOF reduces flow related band broadening and separation efficiencies of several hundred thousand plates per meter are often obtained in CEC. CEC also makes it is possible to use small-diameter packings and achieve very high efficiencies.

Alternatively, isotachophoresis (ITP) is a method of concentrating samples by electrophoretic separation using a discontinuous buffer. See Osbourn, D. M., et al., "On-line Preconcentration Methods for Capillary Electrophoresis" *Electrophoresis* 2000, 21, 2768-2779. In ITP, charged molecules are concentrated at a boundary between a leading and a trailing electrolyte of lower and higher electrophoretic mobility, respectively. The technique can be used in conjunction with capillary electrophoresis where a discontinuous electrolyte system is preferably employed at the site of sample injection into the capillary.

Moreover, transient isotachophoresis (tITP) is a variation of this technique commonly used in conjunction with capillary electrophoresis (CE). Foret, F., et al. describes two electrolyte arrangements for performing tITP. Trace Analysis of Proteins by Capillary Zone Electrophoresis with On-Column Transient Isotachophoretic Preconcentration. *Electrophoresis* 1993, 14, 417-428 (1993).

One configuration employs two reservoirs connected by a capillary. The capillary and one reservoir are filled with a leading electrolyte (LE), while the second reservoir is filled with terminating electrolyte (TE). The sample for analysis is first injected into the capillary filled with LE and the injection end of the capillary is inserted into the reservoir containing TE. Voltage is applied and those components of the sample which have mobilities intermediate to those of the LE and TE stack into sharp ITP zones and achieve a steady state concentration. The concentration of such zones is related to the concentration of the LE co-ion but not to the concentration of the TE. Once a steady state is reached, the reservoir containing TE is replaced with an LE containing reservoir. This causes a destacking of the sharp ITP zones, which allows individual species to move in a zone electrophoretic mode.

The other configuration discussed by Foret, F., et al. employs a similar approach but uses a single background electrolyte (BGE) in each reservoir. The mobility of the BGE co-ion is low such that it can serve as the terminating ion. The sample for analysis contains additional co-ions with high electrophoretic mobility such that it can serve as the leading zone during tITP migration. After sample is injected into the capillary and voltage is applied, the leading ions of higher mobility in the sample form an asymmetric leading and sharp rear boundary. Just behind the rear boundary, a conductivity discontinuity forms, which results in a non-uniform electric field, and thus stacking of the sample ions. As migration progresses, the leading zone broadens due to electromigration dispersion and the concentration of higher mobility salt decreases. The result is decreasing differences of the electric field along the migrating zones. At a certain concentration of the leading zone, the sample bands destack and move with independent velocities in a zone electrophoretic mode.

In preferred embodiments, the samples are separated on using CE, more preferably CEC with sol-gels, or more preferably CZE. This separates the molecules based on their electrophoretic mobility at a given pH (or hydrophobicity in the case of CEC).

A separation channel in a separation microfluidic device of the present invention is preferably coated with a positive coating that reduces molecular interactions at the low pH used in the system, and produces an electro-osmotic flow of at least 10 nL/min, 20 nL/min, 30 nL/min, 40 nL/min, 50 nL/min, 60 nL/min, 70 nL/min, 80 nL/min, 90 nL/min, 100 nL/min, 110 nL/min, 120 nL/min, 130 nL/min, 140 nL/min, or 150 nL/min to feed the electrospray process. Preferably, the electro-osmotic flow is of at least 100 nL/min. The microfluidic devices can separate all serum components in under 12 minutes, with a separation efficiency of 100,000 theoretical plates.

(ii) Chromatography

Chromatography is another method for separating a subset of polypeptides. Chromatography is based on the differential absorption and elution of certain polypeptides. Liquid chromatography (LC), for example, involves the use of fluid carrier over a stationary phase. Conventional LC columns have an in inner diameter of roughly 4.6 mm and a flow rate of roughly 1 ml/min. Micro-LC has an inner diameter of roughly 1.0 mm and a flow rate of roughly 40 µL/min. Capillary LC utilizes a capillary with an inner diameter of roughly 300 um and a flow rate of approximately 5 µL/min. Nano-LC is available with an inner diameter of 10-300 µm or 50 um-1 mm and flow rates of 10-200 nl/min. Nano-LC can vary in length (e.g., 5, 15, or 25 cm) and have typical packing of C18, 5 um particle size. Nano-LC stationary phase may also be a monolithic material, such as a polymeric monolith or a sol-gel monolith. In a preferred embodiment, nano-LC is used. Nano-LC provides increased sensitivity due to lower dilution of chromatographic sample. The sensitivity of nano-LC as compared to HPLC can be as much as 3700 fold.

Ionization

Once prepared and separated, the markers (e.g., polypeptides or small molecules) are automatically delivered to a detection device, which detects the markers (e.g., polypeptides or small molecules) in a sample. In a preferred embodiment, markers (e.g., polypeptides or small molecules) in solution are delivered to a detection device by electrospray ionization (ESI). ESI operates by infusing a liquid containing the sample of interest through a channel or needle, which is kept at a potential (typically 3.5 kV). The voltage on the needle causes the spray to be charged as it is nebulized. The resultant droplets evaporate at atmospheric pressure or in a region maintained at a vacuum as low as several torr, until the solvent is essentially completely stripped off, leaving a charged ion. The charged ions are then detected by a detection device such as a mass spectrometer.

In a more preferred embodiment, nanoelectrospray ionization is used. Nanospray ionization is a miniaturized version of ESI and provides low detection limits using extremely limited volumes of sample fluid.

Ions formed by electrospray ionization normally are singly or multiply charge ions of molecules, with charge coming from protons or alkali metal bound to the molecules. Ion excitation may be produced by collision of ions with background gas or an introduced collision gas, e.g., collision induced dissociation (CID). Alternatively, excitation may be from collision with other ions, a surface, interaction with photons, heat, electrons, or alpha particles. Through excitation of the sample in an electrospray, the information content of the process should be altered and/or enhanced. Such excitation may, for example, desolvate ions, dissociate non-covalently bound molecules from analyte ions, break up solvent clusters, fragment background ions to change their mass to charge ratio and move them to a ratio that may interfere less with the analysis, strip protons and other charge carriers such that multiply charged ions move to different regions of the spectrum, and fragment analyte ions to produce additional, more specific or sequence-related information.

In preferred embodiments of the invention, the selected excitation system may be turned "on" and "off" to obtain a set of spectra in both states. The information content of the two spectra is, in most cases, far greater than the information content of either single spectrum. In such embodiments, the system includes a switching device for activating and de-activating the excitation/ionization system. Analysis software which is part of the informatics tools herein may be configured to analyze the sample separately both in the "on" state of the excitation system and in the "off" state of the excitation system. Different markers may be detected more efficiently in one or the other of these two states.

In preferred embodiments, separated markers, including optionally polypeptides, are directed down a channel that leads to an electrospray ionization emitter, which is built into a microfluidic device (an integrated ESI microfluidic device). Preferably, such integrated ESI microfluidic device provides the detection device with samples at flow rates and complexity levels that are optimal for detection. Such flow rates are, preferably, approximately 1-1000 nL/min, 10-800 nL/min, 20-600 nL/min, 30-400 nL/min, 40-300 nL/min, or more preferably approximately 50-200 nL/min.

Furthermore, a microfluidic device is preferably aligned with a detection device for optimal sample capture. For example, using dynamic feedback circuitry, a microfluidic device may allow for control positioning of an electrospray voltage and for the entire spray to be captured by the detection device orifice. The microfluidic device can be sold separately or in combination with other reagents, software tools and/or devices.

In any of the embodiments herein, pressure may be added to move a sample through a separation device and maintain a stable flow into the detection device. Such pressure may be applied after at least partial preparation of the sample or complete preparation of the sample. Such pressure can be added using a buffered solution which increases/maintains the flow rate of the liquid-containing sample. Such buffer can form a "sheath" around the sample and help sample components migrate to the end of an electrophoretic separation capillary and into the detection device. Such sheath may also dilute the sample being detected.

In some embodiments, the invention contemplates methods for sheathless ionization. In one embodiment, a sheathless ionization element provides voltage from a second channel to produce enough energy to generate the electrospray. In another embodiment, an electrical contact at the spray tip provides the voltage to generate the electrospray.

Figure 11:
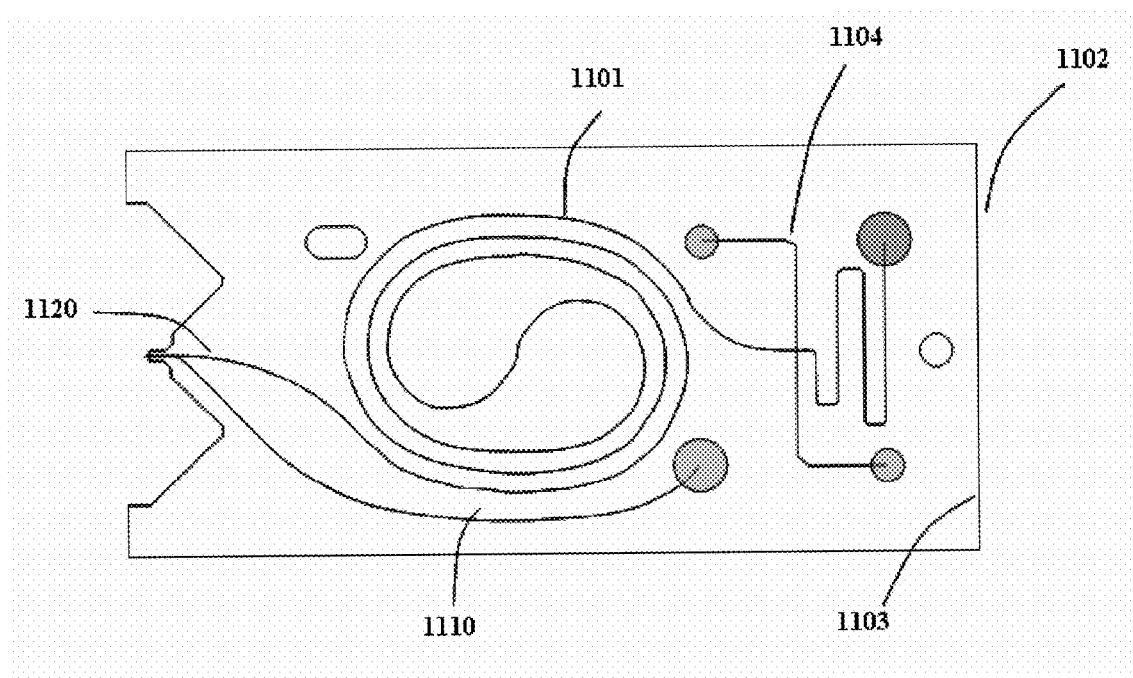
FIG. 11 illustrates an exemplary microfluidic device. The microfluidic device has a curved separation channel, a second channel for application of the electrospray/electrophoresis voltage, and the electrospray emitter tip. The tip is protected from mechanical damage by plastic extensions on either side.
Figure 12:
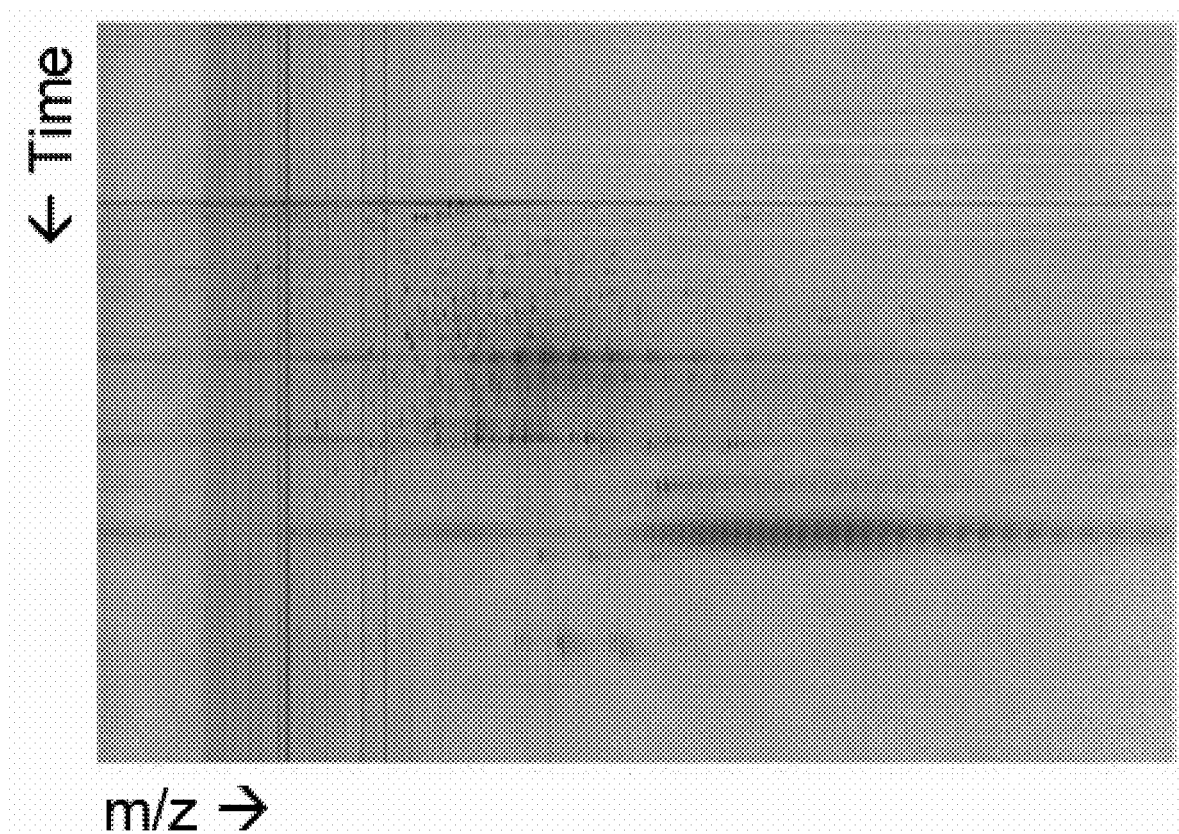
FIG. 12 illustrates a two dimensional plot of a serum separation from the microfluidic device-electrophoresis-electrospray ionization mass spectrometry system.

FIG. 11 is an exemplary embodiment of a microfluidic device having a sheathless ionization element. The microfluidic device in FIG. 11 has a curved separation channel 1101, a second channel 1110 for application of the electrospray/electrophoresis voltage, and the electrospray emitter tip 1120. Sample is inputted in the well at sample input location 1103 and exits in the well at sample output location 1104, while separation buffer is inputted in the well at location 1102. The emitter tip 1120 is protected from mechanical damage by plastic extensions on either side. The microfluidic device is preferably made of a polymeric material, such as plastic, and is disposable. Thus it is contemplated by the present invention that an electrospray emitter is integrated with the preparation/separation microfluidic device which is also polymeric and disposable.

In preferred embodiments, the samples are separated on using capillary electrophoresis separation, more preferably CEC with sol-gels, or more preferably CZE. This will separate the molecules based on their electrophoretic mobility at a given pH (or hydrophobicity in the case of CEC).

Figure 13:
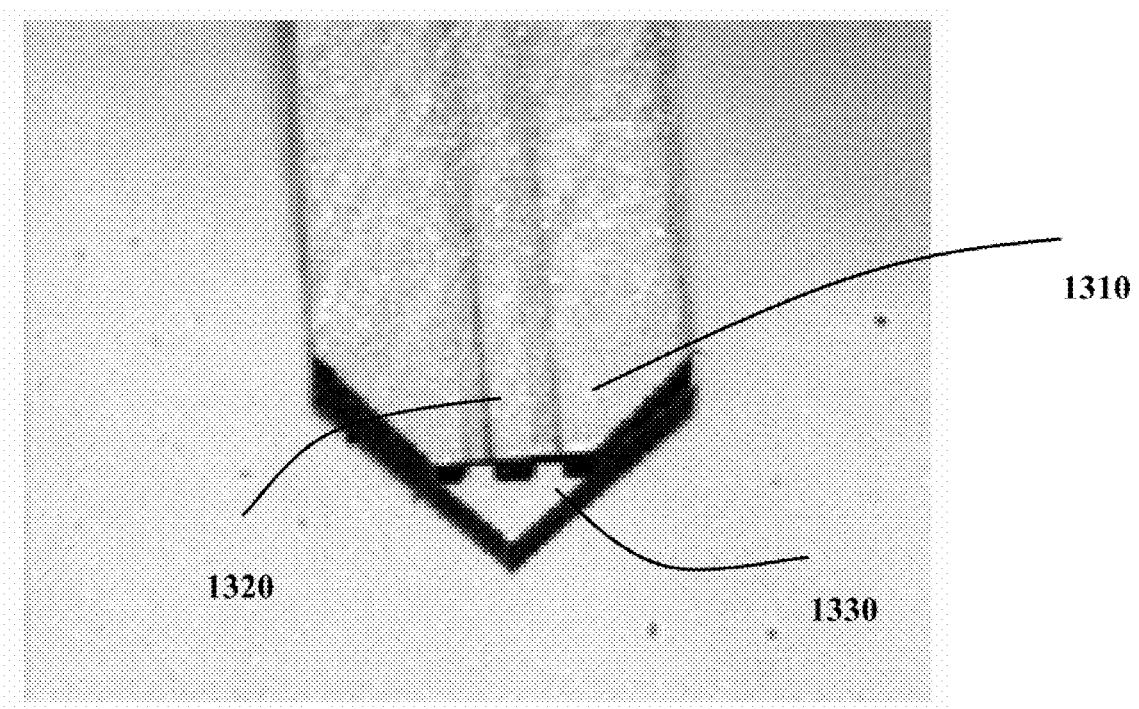
FIG. 13 illustrates an expanded view of the electrospray tip.

FIG. 13 shows the microfluidic device in an expanded view of the electrospray emitter tip. The side channel 1310 is uncoated so no electro-osmotic flow is generated. Positive analyte ions from the separation channel 1320 do not move into the side channel because their electrophoretic mobility is in the opposite direction. Thus, all of the analyte ions are sprayed from the tip 1330 without the dilution effect that is common to similar interfaces that use a sheath. Voltages for the separation and electrospray are provided either to liquids in wells or electrodes in the microfluidic device, which prevents bubble formation in the channels or at the tip due to hydrolysis. The electrospray voltage at the tip is determined by the ratio of the electrical conductivities of the separation and side channels. The voltage provided by side channel 1310 may be, for example, less than 10V, 5V, 1V, 0.5V, 0.1V, 0.05V, 0.01V, or between 0.0001-10 V, between 0.001-1V, or between 0.01 and 0.1V. No additional electrode or tip electrical coating, as found on other integrated electrospray tips for sheathless electrospray interfacing, is used. A voltage controller has been designed to provide the high voltages to each well on the chip, and to change them in proper sequence for sample loading, injection, and separation. Importantly, the voltages are floated with respect to a common, permitting the electrospray voltage to be changed without altering the potential differences between electrodes that drive the separation.

In either sheath or sheathless system, buffers may be used to improve signal intensity and/or carry the voltage charge. Examples of buffers that can be used in a sheath or sheathless system include, but are not limited to, 10-50% methanol 10-50% ethanol, 10-50% n-propanol, 10-50% isopropanol, each including 10-100 nM acetic acid or formic acid.

The selected buffer system can be fully volatile, and moreover, in-line transient isotachophoresis can be employed to further improve signal intensity.

In one embodiment, the present invention relates to a sheathless-ESI interface that couples a capillary electrophoresis (CE) microfluidics device to a time-of-flight (TOF) mass spectrometer for the automated separation and detection of intact polypeptides in human serum. The sheathless interface provided in this embodiment of the invention is often preferred for its relatively improved inherent sensitivity. To further increase sensitivity, it may be preferable under particular conditions to employ transient isotachophoresis (tITP) to concentrate a sample on-line.

In some embodiments, pressure is added using a combination of sheath and sheathless processes.

Calibrants can also be sprayed into detection device. Calibrants are used to set instrument parameters and for signal processing calibration purposes. Calibrants are preferably utilized before a real sample is assessed or at the same time a real sample is assessed. Calibrants can interface with a detection device using the same or a separate interface as the samples. In a preferred embodiment, calibrants are sprayed into a detection device using a second interface (e.g., second spray tip).

Microfluidic Devices

In some of the embodiments herein, sample preparation and/or separation occur on a micro fluidic device. In other preferred embodiments, the steps of sample preparation and separation are combined using microfluidics technology. A microfluidic device is a device that can transport liquids including various reagents such as analytes and elutions between different locations using microchannel structures. Microfluidic devices provide advantageous miniaturization, automation and integration of a large number of different types of analytical operations. For example, continuous flow microfluidic devices have been developed that perform serial assays on extremely large numbers of different chemical compounds. Microfluidic devices may also provide the feature of disposability, to prevent sample carry-over. By microfluidic device it is intended to mean herein devices with channels smaller than 1000 µm, preferably less than 500 µm, and more preferably less than 100 µm. Preferably such devices use sample volumes of less than 1000 µl, preferably less than 500 µl, and most preferably less than 100 µl.

Preferably, both sample preparation and separation occur on microfluidic device(s). More preferably, both sample preparation and sample separation occur on the same microfluidic device. Optimally, any of the above, or more preferably a single preparation/separation microfluidic device interfaces directly or indirectly with a detection device. Preferably, the microfluidic devices are disposable, meaning that they are marketed for one or a few uses followed by disposal and replacement. Preferably, sample preparation occurs using conventional methods, while separation occurs on a microfluidic device.

The microfluidic devices herein are preferably polymeric and/or disposable. A microfluidic devices (or chip) may be formed in any material known in the art. In some embodiments, a microfluidic device herein is formed from a polymer such as plastic by means of, for example, etching, machining, cutting, molding, casting or embossing. In some embodiments, the microfluidic devices can be made from glass or silicon by means of, for example, etching, machining, embossing, or cutting. In some embodiments, the microfluidic devices may be formed by polymerization on a form or other mold. Preferably, the microfluidic devices may be fabricated by hot embossing of PMMA and the channels are sealed by lamination with a 75 um PMMA film.

A positively-charged coating can then be applied to the separation channel after lamination. A microfluidic device can provide multiple integrated operations as well as fast separations, efficient electrospray ionization, high throughput, zero carry-over between samples, and reliable, reproducible, connection-free fluid junctions. The particular operations performed by the microfluidic devices herein depend, in part, upon the detection technology that is utilized.

A mass spectrometer of the present invention, preferably contains a disposable inlet capillary(ies) for receiving spray from a microfluidic device. Inlet capillaries can be made with high precision, and mating of hardware to the mass spectrometer can be performed by a person of ordinary skill in the art. A capillary within a mass spectrometer herein is preferably designed to include a faceplate to avoid the need to clean the outside face of the MS inlet. Furthermore, the inlet capillary could be connected directly or indirectly to the electrospray emitter. Preferably, the orientation and/or proximity of the emitter tip to the inlet capillary is pre-determined and does not need to be set or adjusted by the user. Some of the benefits of the capillary inlets is that it allows an operator to simply replace the mass spectrometer's inlet capillary assembly as opposed to having to dismantle and clean the entire source of the mass spectrometer.

A microfluidic device can transport liquids including various reagents such as analytes and elutions between different locations using microchannel structures. Microfluidic devices provide advantageous miniaturization, automation and integration of a large number of different types of analytical operations. For example, continuous flow microfluidic devices have been developed that perform serial assays on extremely large numbers of different chemical compounds. Microfluidic devices may also provide the feature of disposability, to prevent sample carry-over.

By microfluidics device it is intended to mean devices with channels having a channel width smaller than 1000 µm, 900 µm, 800 µm, 700 µm, 600 µm, 500 µm, 400 µm, 300 µm, 200 µm, 100 µm, 50 µm or 10 µm and a channel height of the same or similar dimension. In some embodiments, such devices perform functions on a sample having volume less than 1000 nL, 900 nL, 800 nL, 700 nL, 600 nL, 500 nL, 400 nL, 300 nL, 200 nL, 100 nL, 50 nL, 10 nL, 5.0 nL, 1.0 nL, 0.5 nL, 0.1 nL or less.

The microfluidic devices may be either single use for a single sample; multi-use for a single sample at a time with serial loading; single use with parallel multiple sample processing; multi-use with parallel multiple sample processing; or a combination. Furthermore, more than one microfluidic device may be integrated into the system and interface with a single detection device. In preferred embodiments, the microfluidic device is a disposable device that is readily connected to and removed from the mass spectrometer, and sold as a disposable, thereby providing a recurring revenue stream to the involved business and a reliable product to the consumer. Preferably, the disposable product is for single use only. In some embodiments, the disposable microfluidic device is for multiple uses. Preferably, a mass spectrometer that accepts a continuous sample stream for analysis and provides high sensitivity throughout the detection process is utilized. Preferably, any reagents used for preparation/separation are provided in or along with the microfluidic device, thereby allowing for additional recurring revenue to the business herein and higher performance for the user. In some of the embodiments herein, the microfluidic device(s) have a sheathless ionization interface.

It is further contemplated that after detection of a marker, the business herein may further develop diagnostic products based on such marker. A diagnostic product for a polypeptide marker can include, for example, an antibody (polyclonal, monoclonal, humanized, or a fragment thereof) or other agent that can detect the presence/absence or level of a marker in a sample.

The business methods herein also contemplate providing diagnostic services to, for example, health care providers, insurers, patients, etc. The business herein can provide diagnostic services by either contracting out with a service lab or setting up a service lab (under Clinical Laboratory Improvement Amendment (CLIA) or other regulatory approval). Such service lab can then carry out the methods disclosed herein to identify if a particular pattern and/or marker is within a sample.

Once prepared and separated, the polypeptides are automatically delivered to a detection device, which detects the polypeptides in a sample. In a preferred embodiment, polypeptides in elutions or solutions are delivered to a detection device by electrospray ionization (ESI). ESI operates by infusing a liquid containing the sample of interest through a channel or needle, which is kept at a potential (typically 3.5 kV). The voltage on the needle causes the spray to be charged as it is nebulized. The resultant droplets evaporate in a region maintained at a vacuum of several torr, until the solvent is essentially completely stripped off, leaving a charged ion. The charged ions are then detected by a detection device such as a mass spectrometer. In a more preferred embodiment, nanospray ionization (NSI) is used. Nanospray ionization is a miniaturized version of ESI and provides low detection limits using extremely limited volumes of sample fluid.

In preferred embodiments, separated polypeptides are directed down a channel that leads to an electrospray ionization emitter, which is built into a microfluidic device (an integrated ESI microfluidic device). Preferably, such integrated ESI microfluidic device provides the detection device with samples at flow rates and complexity levels that are optimal for detection. Such flow rates are, preferably, approximately 50-200 uL/min. Furthermore, a microfluidic device is preferably aligned with a detection device for optimal sample capture. For example, using dynamic feedback circuitry, a microfluidic device may allow for control positioning of an electrospray voltage and for the entire spray to be captured by the detection device orifice. The microfluidic device can be sold separately or in combination with other reagents, software tools and/or devices.

Calibrants can also be sprayed into detection device. Calibrants are used to set instrument parameters and for signal processing calibration purposes. Calibrants are preferably utilized before a real sample is assessed. Calibrants can interface with a detection device using the same or a separate interface as the samples. In a preferred embodiment, calibrants are sprayed into a detection device using a second interface (e.g., second spray tip).

Detection

Detection devices can comprise any device or use any technique that is able to detect the presence and/or level of a composition in a sample. Examples of detection techniques that can be used in a detection device include, but are not limited to, nuclear magnetic resonance (NMR) spectroscopy, 2-D PAGE technology, Western blot technology, immunoanalysis technology, electrochemical detectors, spectroscopic detectors, luminescent detectors, and mass spectrometry.

In a preferred embodiment, the system or business model herein relies on a mass spectrometry to detect biomarkers, such as polypeptides, present in a given sample. There are various forms of mass spectrometers that may be utilized.

In a preferred embodiment, an ESI-MS detection device is utilized. An ESI-MS combines the novelty of ESI with mass spectrometry. Furthermore, an ESI-MS preferably utilizes a time-of-flight (TOF) mass spectrometry system. In TOF-MS, ions are generated by whatever ionization method is being employed and a voltage potential is applied. The potential extracts the ions from their source and accelerates them towards a detector. By measuring the time it takes the ions to travel a fixed distance, the mass of the ions can be calculated. TOF-MS can be set up to have an orthogonal-acceleration (OA). OA-TOF-MS are advantageous and preferred over conventional on-axis TOF because they have better spectral resolution and duty cycle. OA-TOF-MS also has the ability to obtain spectra at a relatively high speed. See Brock et al. Anal. Chem (1998) 70, 3735-41, discuss on-axis TOF known as Hadamard OA-TOF-MS. In addition to the MS systems disclosed above, other forms of ESI-MS include quadrupole mass spectrometry, ion trap mass spectrometry, orbitrap mass spectrometry, and Fourier transform ion cyclotron resonance (FTICR-MS).

Quadrupole mass spectrometry consists of four parallel metal rods arranged in four quadrants (one rod in each quadrant). Two opposite rods have a positive applied potential and the other two rods have a negative potential. The applied voltages affect the trajectory of the ions traveling down the flight path. Only ions of a certain mass-to-charge ratio pass through the quadrupole filter and all other ions are thrown out of their original path. A mass spectrum is obtained by monitoring the ions passing through the quadrupole filter as the voltages on the rods are varied.

Ion trap mass spectrometry uses three electrodes to trap ions in a small volume. The mass analyzer consists of a ring electrode separating two hemispherical electrodes. A mass spectrum is obtained by changing the electrode voltages to eject the ions from the trap. The advantages of the ion-trap mass spectrometer include compact size, and the ability to trap and accumulate ions to increase the signal-to-noise ratio of a measurement Orbitrap mass spectrometry uses spatially defined electrodes with DC fields to trap ions. Ions are constrained by the DC field and undergo harmonic oscillation. The mass is determined based on the axial frequency of the ion in the trap.

FTICR mass spectrometry is a mass spectrometric technique that is based upon an ion's motion in a magnetic field. Once an ion is formed, it eventually finds itself in the cell of the instrument, which is situated in a homogenous region of a large magnet. The ions are constrained in the XY plane by the magnetic field and undergo a circular orbit. The mass of the ion can now be determined based on the cyclotron frequency of the ion in the cell.

In a preferred embodiment, the system or business model herein employs a TOF mass spectrometer, or more preferably, an ESI-TOF-MS, or more preferably an OA-TOF-MS, or more preferably a mass spectrometer having a dual ion funnel and that supports dynamic switching between multiple quadrupoles in series, the second of which can be used to dynamically filter ions by mass in real time. In preferred embodiments, the detection device yields spectra at a rate of more than 0.1, 0.2, 0.3, 0.4, 0.5, 0.6, 0.7, 0.8, 0.9, 1, 2, 3, 4, 5, 6, 7, 8, 9, or 10 seconds per spectra. In preferred embodiments, the detection device yields a spectrum of at least 150, more preferably 200, or more preferably 300 spectrums per second.

The detection device preferably interfaces with a separation/preparation device or microfluidic device, which allows for quick assaying of many of the polypeptides in a sample, or more preferably, most or all of the polypeptides in a sample. Preferably, a mass spectrometer is utilized that accepts a continuous sample stream for analysis and provide high sensitivity throughout the detection process (e.g., an ESI-MS). In another preferred embodiment, a mass spectrometer interfaces with one or more electrosprays, two or more electrosprays, three or more electrosprays or four or more electrosprays. Such electrosprays can originate from a single or multiple microfluidic devices.

In some preferred embodiments, the system herein employs a TOF mass spectrometer, or more preferably, an ESI-TOF-MS, or more preferably an ESI-OA-TOF-MS. In preferred embodiments, a mass spectrometer may have a single or dual ion funnel(s) and that supports dynamic switching between multiple quadruples in series, the second of which can be used to dynamically filter ions by mass in real time. Such MS detection devices are described in more detail in Belov, M. E., et al. (2000) *J Am Soc Mass Spectrom* 11, 19-23 and Belov, M. E., et al. (2000) *Anal Chem* 72, 2271-9.

Figure 14:
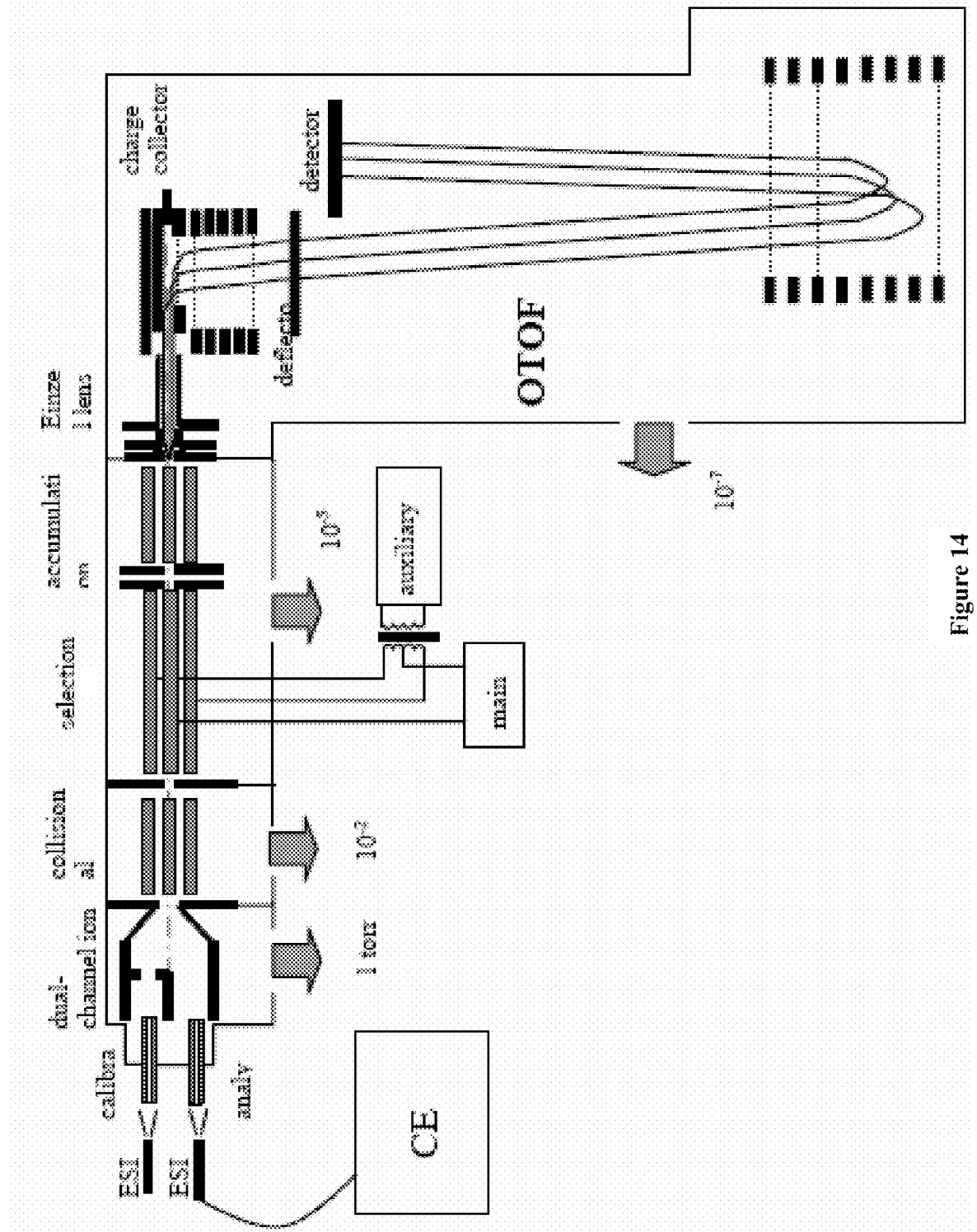
FIG. 14 illustrates a TOF-MS coupled to a separation device.

FIG. 14 illustrates an exemplary embodiment of a detection device of the present invention.

In some embodiment, an injection volume of the microfluidic device is less than 10 nL, 9 nL, 8 nL, 7 nL, 6 nL, 5 nL, 4 nL, 3 nL, 2 nL, 1 nL, 0.9 nL, 0.8 nL, 0.7 nL, 0.6 nL, 0.5 nL, 0.4 nL, 0.3 nL, 0.2 nL, or 0.1 nL. In some embodiments, less than 500 µL, 400 µL, 300 µL, 200 µL, 100 µL, 90 µL, 80 µL, 70 µL, 60 µL, 50 µL, 40 µL, 30 µL, 20 µL, 10 µL, 9 µL, 8 µL, 7 µL, 6 µL, 5 µL, 4 µL, 3 µL, 2 µL, or 1 µL of a sample or less is analyzed per assay.

The instrument has features for ion accumulation, ion selection, and scan overlapping that are being developed to improve sensitivity and capability further, and it can be configured for tandem mass spectrometry.

The detection system utilized preferably allows for the capture and measurement of most or all of the components (e.g., markers and polypeptides) that are introduced into the detection device. It is preferable that one can observe components (e.g., markers and polypeptides) with high information-content that are only present at low concentrations. By contrast, it is preferable to remove those in advance that are, for example, common to all cells, especially those in high abundance.

The detection devices herein can be used singly or in combination with one another.

Informatics

The output from a detection device can then be processed, stored, and further analyzed or assayed using a bio-informatics system. A bio-informatics system can include one or more of the following: a computer; a plurality of computers connected to a network; a signal processing tool(s); a pattern recognition tool(s); and optionally a tool(s) to control flow rate for sample preparation, separation, and detection.

Quality Assurance

Quality assurance methods are used to ensure that devices and/or instrumentations herein function properly and that outliers are discovered before discriminatory patterns are sought. Generally, quality assurance uses metrics including, but not limited to, total intensity of a spectrum, intensity of calibrants, intensity of expected peaks, resolution of calibrants, resolution of expected peaks, mass accuracy of calibrants, mass accuracy of expected peaks, ratios of intensities of peaks or other metrics alone or in combinations to eliminate data that should not be further analyzed due to issues such as, but not limited to, data acquisition problems or sample collection problems.

Signal Processing

Data/signal processing utilizes mathematical foundations. Generally, dynamic programming or non-linear fitting is preferably used to align a separation axis with a standard separation profile. Furthermore, intensities may be normalized, preferably by dividing by the total ion current of a spectrum or by dividing by the intensity of a calibrant, or using quantile normalization methods or by fitting roughly 90% of the intensity values into a standard spectrum. The data sets are then fitted using wavelets or other methods that are specifically designed for separation and mass spectrometer data. Data processing preferably filters out some of the noise and reduces spectrum dimensionality. This allows the system or business to identify the more highly predictive patterns.

Data/signal processing may involve the use of mathematical algorithms. Such signal processing can combine statistical and machine learning approaches to isolate the information-rich data features (e.g. forward and backward selection or ranking by univariate statistics, combined with Support Vector Machines and Kernel Discriminant Analysis), thereby reducing the dimensionality of the data and determining the combinations of these features that are highly predictive of a biological state or condition of interest. Rigorous cross-validation, false discovery rate analysis, and the use of independent validation sets remove issues with overfitting of data and bias in the study and allow finding more highly predictive and robust patterns that are more generalizable (i.e., patterns that are useful for analyzing other samples sets).

In some embodiments, data/signal processing may also involve the calibration of a mass-axis using linear correction determined by the calibrants. Calibration can take place prior to any sample detection; after sample detection; or in recurring intervals, for example.

A signal processing device herein can process data consisting of at least 100, 200, 300, 400, 500, 600, 700, 700, 900, 1000, 5000, or 10,000 spectra, or at least 100, 200, 300, 400, 500, 600, 700, 700, 900, 1000, 5000, or 10,000 spectra/hour.

Thus, in any of the embodiments herein, data/signal processing can involve one or more of the following steps: (i) correcting for any lack of experimental reproducibility, (ii) noise reduction/removal, and (iii) dimensionality reduction.

(i) Correcting for Lack of Experimental Reproducibility

Artifacts can be corrected using intensity normalization, transformation, and separation time alignment. Under this method, the intensity at each point in a spectrum is divided by the Total Ion Current (TIC) or by the intensity of a calibrant or by quantile normalization. This puts intensity on an absolute scale and allows comparisons across spectra. Additionally, each intensity value can be replaced by its square root (or log) to stabilize variances. Dynamic programming or non-linear fitting can be used to correct for any local or global contractions or dilations in the time in which components elute off the separations channel or column. A global alignment across all samples or an alignment to a standard spectrum can also be performed. These approaches increase the precision of data and allow the comparison of spectrum with the correct corresponding spectrum in a different data set, even if the separations in the two experiments were different.

(ii) Noise Reduction/Removal

Standard denoising methods, such as Savitzky-Golay, as well as other methods using wavelet and Fourier transforms can be used to reduce experimental artifacts. Such methods remove high frequency noise in a spectrum without altering the generally lower frequency signal.

(iii) Dimensionality Reduction

Experimental artifacts can be reduced by reduction of dimensionality. Dimensionality reduction is used to reduce the number of dimensions to ~1000s and greatly reduce the risk of classifying based on noise. The reduction in the number of data features gives greater statistical assurance that patterns analyzed are predictive and generalizable. Examples of methods used for dimensionality reduction include, for example, simple models of throwing out data points with high P-values in a univariate statistical test and more complex models that use Support Vector Machines (SVMs) in an iterative manner.

Any of the signal processing tools above may include or be coupled to other software elements as well. For example, the signal processing system may provide for an easy to use user interface on the associated computer system and/or a patient database for integration of results into an institution's laboratory or patient information database system.

Pattern Recognition

Following data processing, pattern recognition tools are utilized to identify differences between biological or phenotypic states or conditions that may affect an organism. Pattern recognition tools are based on a combination of statistical and computer scientific approaches, which provide dimensionality reduction. Such tools are scalable.

Pattern recognition methods take as input the normalized, aligned, de-noised and dimensionally reduced data sets and find patterns that classify the patients into classes (for example, case versus control). The present invention contemplates any pattern recognition method known in the art, but preferably one or more of the following: Support Vector Machines, Discriminant Analysis, k-Nearest Neighbor, and Nearest Shrunken Centroid. Additional pattern recognition algorithms are also contemplated by the methods herein.

Pattern recognition methods can be used to find, for example, sets of data points (e.g., m/z values) that distinguish samples (e.g., cases from controls). Preferably, a three-fold cross validation is used to discover and test patterns found using the above techniques. Three-fold cross validation means that the dataset is divided into thirds, where one third is set aside as a test set and the other two thirds are used as a training set. This is performed three times, using a different third of the data as the test set each time. The training data is used to select features and find patterns that distinguish between the two groups (e.g., breast cancer and healthy). The test set is then used to assess how well the patterns perform on independent and blind data. Such cross validation methodology is very important in supervised learning, since it insures that the predictive power of the pattern is assessed using a test set and thus is not biased. If such methods are not used, it is possible that data may be overfit and patterns discovered may not be generalizable (i.e. not translate to new independent data and new populations). Thus, patterns discovered using the methods herein can be converted into simple decision algorithms in a diagnostic setting.

In some embodiments, pattern recognition methods utilize hierarchical clustering, which is an unsupervised pattern recognition method. This method does not use information on the biological state of interest, but rather tries to organize the data into clusters based only on information found in the data. Such a method is especially useful for identifying sub-groupings within the data. For example, there may be subgroups of breast cancer that are due to known factors (e.g., Her2/neu overexpression) or due to unknown factors that have biological significance and could be the basis for further research. Such classifications may be important for understanding prognosis.

Data are analyzed in several ways. First univariate statistics are used to find single data points that correlate with the presence/absence of a biological or condition of interest. Such methods can be used either with or without prior signal processing. Standard non-parametric methods, such as non-parametric versions of the t-test (Mann-Whitney test) corrected for multiple comparisons by, for example, a Bonferroni correction are used to analyze the data. After ranking by P-value, the data is visualizes data points with low P-values and high group-mean differences are reported.

A suite of advanced signal processing and pattern classification methods may optionally be used to find patterns in the data that are indicative of the presence/absence of a biological state or condition of interest. Data analysis pipelines have been constructed from various methods of both signal processing and pattern recognition. Such pipelines may find relevant signals in complex data as well as very good discriminatory patterns. Sensitivities and specificities—as well as other relevant statistics such as area under the curve (AUC) of the receiver operator characteristic (ROC) curve and positive/negative predictive value—of patterns of data points that can highly discriminate between classes are reported. Examples of signal processing and pattern recognition methods used are described in more detail below.

In the case that a pattern of markers for a biological state of interest (e.g., a condition such as disease) is discovered or known and we want to assay another sample to determine if that patient has the disease, data could be analyzed as follows. After separation time alignment with dynamic programming or non-linear fitting, the intensities of datapoints corresponding to the markers of interest could be normalized by dividing by the total ion current, the intensity of a calibrant, or by quantile normalization. The normalized intensities may then be log or square root transformed, or left as is. The resulting intensities would be combined as instructed in the discovery data analysis to yield a single number that would predict the biological or disease state of the patient. In this case, when assaying additional samples, no feature selection and pattern recognition would be used since the pattern would already be known.

EXAMPLES

The following prophetic example illustrates certain aspects of the invention.

Approximately one to five ml of blood will be collected through venipuncture into special tubes that contain the appropriate calibrants/controls. Following thorough clot formation, serum will be isolated from sample following centrifugation. Serum sample will be aliquoted and frozen at −70 C until analysis. On the order of 100 uL of thawed sample will be placed in a disposable plastic device that fits into a manifold, and hereafter, the entire process would be automated. The device will perform electrodialysis on the sample. Using an electric field and tangential flow, the sample will be passed through a membrane that allows only molecules under approximately 30 kD (not a sharp cutoff) to pass through into a second chamber. Molecules of with the opposite charge or large molecules will not pass. A second membrane with a very low molecular weight cutoff (~500D) will allow small molecules to pass out of the second chamber. Molecules that remain in the second chamber will therefore be in a MW range (500D-30 kD). Most of these molecules will be peptides, protein fragments and small proteins. Salts will have been removed, as will most of the abundant polypeptides, such as albumin. This process should take approximately 60 minutes.

The molecules of interest (i.e. those that remain in the second chamber) will then be moved to another location on the disposable device, again using an electric field, and onto reverse phase beads for sample concentration. Using an organic solvent elution such as 50% methanol, the molecules will be eluted into a channel or well on a second disposable device, this time a microfluidics chip. On this chip, a 1-5 minute capillary electrophoretic separation, CZE or CEC, will be run to separate the molecules on the basis of electrophoretic mobility at the given pH (or hydrophobicity in the case of CEC). Preferred separation peak widths under 1 second will be utilized.

Separated molecules will be directed down a channel that leads to a electrospray ionization emitter that is built onto each chip. Expected flow rates are 50-200 uL/min. Prior to starting the separation, the microfluidics device will be aligned with the mass spectrometer using dynamic feedback circuitry to optimally control positioning stage placement and electrospray voltage to establish a stable spray and, assuming appropriate nl flow rates, allow the entire spray to be captured in the mass spectrometer orifice. Standards/calibrants would also be sprayed into the mass spectrometer using a dedicated second spray tip and used to set instrument parameters and for signal processing calibration purposes before the real samples are run.

An orthogonal multiplexed mass spectrometer captures the spray from the prepared/separated sample (given that it is separated, the molecules will be migrating in small groups) and yield a spectrum at a rate of 200 spectrum/s. The mass spectrometer incorporates a dual ion funnel to support dynamic switching between calibrants and analyte sprays to optimize instrument accuracy. The instrument contains multiple quadrapoles in series, the second of which can, in real time during a data acquisition run, be used to dynamically filter ions by mass, thus allowing increased dynamic range or focus on particular mass ranges of interest. The orthogonal Multiplexed implementation allows multiple ion packets to fly in the flight tube while at the same time decoupling mass accuracy from beam modulation rate, thus supporting high throughput, high sensitivity, and high mass resolution.

A resulting data set from one sample would have on the order of $10^9$ data points. Each data set would take approximately 5 minutes to collect, from start to finish. While a data set is being analyzed, a second sample could be run through the system to increase throughput.

Each data set would have its mass axis calibrated through a linear correction determined by the calibrants run before the sample and by the calibrants run in parallel in the dual ion funnel. Then dynamic programming would be used to align the separations axis (using the TIC) to some standard separations profile. Intensities would then be normalized by fitting the 90% intensity values to a standard spectrum.

These corrected data sets would then be fit using wavelets (or vaguelettes) that are specifically designed for separations/mass spectrometer data. The parameterized information about the spectrum would be soft thresholded and otherwise filtered to both remove noise and reduce dimensionality.

During pattern discovery, a set of approximately 50 case and 50 controls of these filtered parameter sets would be entered into a pattern recognition tool such as a linear support vector machine, but probably multiple learning algorithms will be used on each data set. The space of tunable parameters for the learning machine will be searched, and optimal patterns that distinguish the sample classes will be found, as would be error bounds on that prediction using cross-validation.

During validation or in clinical assay, the filtered parameters from each new data set would be classified into a category by identifying which side of the decision boundary in the multidimensional parameter space that data set lies. Confidence intervals could also be calculated. This prediction and confidence interval would be reported back to the technician running the machine. In some embodiments the information about these clinical samples would be captured and those results and clinical outcomes of those patients in pattern recognition using more samples would be used, yielding better patterns to improve classification.

Eventually, polypeptides/patterns that give rise to the most important data points for prediction could be identified using a tandem mass spectrometry approach. Once a pattern is discovered, separations will be optimized to increase the amount of information about the polypeptides of interest, by slowing down separations during the elution of those polypeptides and speeding it up elsewhere. This would allow for the use of a separate, efficient assay for every diagnostic developed It is to be understood that the above embodiments are illustrative and not restrictive. The scope of the invention should be determined with respect to the scope of the appended claims, along with their full scope of equivalents.

Example 1

Automated separation and detection of intact polypeptides from selected samples was performed using a sheathless CE-ESI-MS system. The selected CE-ESI-MS system was assembled from a combination of commercially available and custom-built instrumentation as follows.

Materials

The system included a Beckman P/ACE MDQ (Beckman Coulter, Fullerton, Calif.) with a cooled sample garage and an EDA cartridge to allow the separations capillary to exit the instrument to the mass spectrometer. The MDQ was grounded to the chassis of the mass spectrometer when CE-MS was performed.

The separations capillary was mated to the electrospray emitter via an ADPT-PRO nanoelectrospray adapter (New Objective, Woburn, Mass.). The adapter was used according to the instructions provided by the manufacturer. Briefly, the ends of the separation capillary and spray emitter are inserted into a modified, plastic, zero-dead-volume union and sealed in place with plastic finger-tight screws and sleeves. Voltage was applied via a metal adapter attached to the screw holding the emitter in place. The interface was mounted on an xyz positioning stage to allow adjustment of the emitter position relative to the inlet of the mass spectrometer. A CCD camera (Model KP-M22AN, Hitachi Kokusai, Japan) was mounted to enable visualization of the spray and the position of the emitter tip. For work with human serum, a plastic enclosure was built to enclose the interface in a chamber at a slight negative pressure.

Fused silica capillaries (360 μm OD, 50 μm ID) were purchased from Polymicro Technologies (Phoenix, Ariz.). The inner surface was cleaned and derivatized with methacryloylaminopropyltrimethylammonium chloride (MAPTAC) according to a variation of the procedure of Kelly, J. F. in *Analytical Chemistry* 1997, 69, 51-60. This produced a hydrophilic, positively-charged coating on the inner surface. Briefly, the capillary is rinsed with sodium hydroxide for 45 minutes, water for 45 minutes, and methanol for 15 minutes to clean the surface. Next, the capillary is silanized by flushing a 0.5% v/v solution of 7-oct-enyltrimethoxysilane in acidified methanol (0.5% v/v acetic acid in methanol) overnight followed by 15-minute rinses of methanol and water. To initiate polymerization, 40 μL of TEMED and 140 μL of 10% w/v freshly prepared APS are added to a freshly prepared solution of 5% MAPTAC. The MAPTAC solution is then pumped through the capillary overnight, followed by a one-hour water rinse. After derivatization with poly-MAPTAC, the capillaries were stored wet at 4° C. until use. Typically, two ~3 m lengths of capillary were prepared at the same time and were referred to as a batch. The electroosmotic flow (EOF) was measured under standardized conditions on a segment from each batch of poly-MAPTAC derivatized capillary and found to vary by less than 5% batch-to-batch.

Fused silica electrospray emitters (TT360-50-5-D-5) were purchased from New Objective (Woburn, Mass.) and derivatized with poly-MAPTAC according to the procedure described above. The emitters used for the pattern recognition experiment were purchased with a conductive coating applied to the distal end. The frontal (tip) end is tapered from the outer diameter of 360 μm to the inner diameter of 50 μm. After derivatization, emitters were stored submersed in water until use. Before use, emitters were rinsed with acetone and cut carefully to 3 cm. The cleaned and cut emitters were inspected under a microscope for the integrity of the polyimide and conductive coatings at the cut end of the emitter. Any overhanging coating material was carefully removed under microscope observation with a dental pick. Damaged emitters were not used and were discarded.

Methods

Selected samples were separated by capillary electrophoresis (CE), subjected to electrospray ionization (ESI) and analyzed in a mass spectrometer (MS) as follows. Electrophoresis was performed at a constant −20 to −40 kV voltage in a 65-cm capillary coated internally with poly-MAPTAC as described in the previous section. The run buffer was 10-30% methanol and 20-80 mM acetic acid (pH 3.2). The stacking solution was prepared by adding 5-10 μL of a stock of 5.02 N ammonia to 1.5 nL of run buffer (pH 4.7). For the pattern recognition experiment, serum was injected for about 5 seconds at about 9.5 psi followed by the stacking buffer for about 5 seconds at about 4.8 psi. Under these conditions, the EOF was approximately $5 \times 10^{-4}$ cm$^2$ V-sec.

To reduce evaporation, the bottom of a 2 mL Beckman P/ACE sample vial was filled with 250-450 μL of run buffer. The serum sample was transferred into a 200 μL PCR vial, suspended on a spring inside the 2 mL vial, and capped before loading into the sample tray of the P/ACE MDQ. The sample garage of the MDQ instrument was kept at 4° C.

Before each injection of serum, the capillary was rinsed and conditioned by a series of five pressure rinse steps performed for 1-3 minutes at 10-30 psi. The five solutions were in sequence: 75 mM ammonia in run buffer, 1.8 M formic acid, water, 60 mM acetic acid, and run buffer.

The electrospray voltage was supplied independently by the mass spectrometer. While developing this methodology, the electrospray voltage was adjusted manually to provide optimal spray stability and detected signals, and was typically 2-3 kV. For selected experiments with spiked serum for pattern recognition, the volumetric flowrate was approximately 280 nL/min, and the electrospray voltage was constant at 2.3 kV. Furthermore, the mass spectrometer was operated in positive ion mode and was mass calibrated daily. The daily mass calibration may be particularly important for informatics algorithms to perform optimally, as the algorithms are sensitive to drifts in the mass accuracy.

In the development of the separations methodology, an ABI Mariner (Applied Biosystems, Foster City, Calif.) time-of-flight mass spectrometer was used as the detector. For the pattern recognition experiments involving serum, an in-house constructed orthogonal TOF mass spectrometer with a two-stage ion reflector was used. In this instrument, ions were introduced into the extraction chamber after passing through an electrodynamic ion funnel/collisional quadrupole assembly, selection quadrupole, and an Einzel lens arrangement. The home-built mass spectrometer was controlled and data acquired using a software program developed in a LabView environment (National Instruments, Austin, Tex.). The m/z resolution was typically 3500-4000 for the +3 charge state of neurotensin, and the mass accuracy was typically 3 ppm.

When performing CE-MS in automated mode, a relay-open step was incorporated into the electrophoresis method file to trigger mass spectral data acquisition. Instrument-specific parameters for the MDQ and TOF-MS were controlled independently.

Results

Because detection limitations are an important factor in the discovery of biomarkers, sheathless CE-ESI-MS provides improved sensitivity that can be effectively used as biomarker discovery tools.

The initial selection of an ESI-MS combination in selected systems herein presented certain common and practical challenges. The use of ESI-MS as a detection method for CE imposes well-known restrictions on the choice of buffer and capillary chemistry. For example, to minimize blocking the inlet capillary of the MS with salt crystals and to minimize formation of salt adducts, only volatile components are used in the separation buffer. For maximum sensitivity, components should be excluded from the run buffer that compete with the analytes for charge in the electrospray, causing signal loss due to ion suppression. Furthermore, the composition of the buffer must be chosen so as to support stable electrospray at the given flow rate of the separation. Optimal choices for buffer components are water, volatile organics, (commonly acetonitrile or methanol) and volatile acids (commonly acetic or formic acid). When there is no sheath flow, the flow that supports the electrospray is supplied by the electro-osmotic flow (EOF) generated in the separations capillary. Since the MS was operated in positive-ion mode, the inner surface of the separation capillary was modified with the covalently-linked, hydrophilic, positively-charged coating poly (MAPTAC). Kelly, J. F., et al. have reported previously the utility of this coating chemistry for CE-MS of peptides in *Analytical Chemistry* 1997, 69, 51-60. The fixed positive charge on the coating generates the electro-osmotic flow, and it was expected that the combination of fixed positive charge and hydrophilicity of the coating would minimize adsorption of the primarily positively-charged components of serum.

As part of the sample preparation workflow, serum samples were de-salted by adsorption on reverse phase material. After washing the reversed-phase material, the serum components were then eluted in 60-80% acetonitrile/0.1-0.5% acetic acid. Thereafter, performance of the separations in an aqueous solution of acetic acid or formic acid and acetonitrile (0-40%) was first investigated.

Example 2

Figure 10:
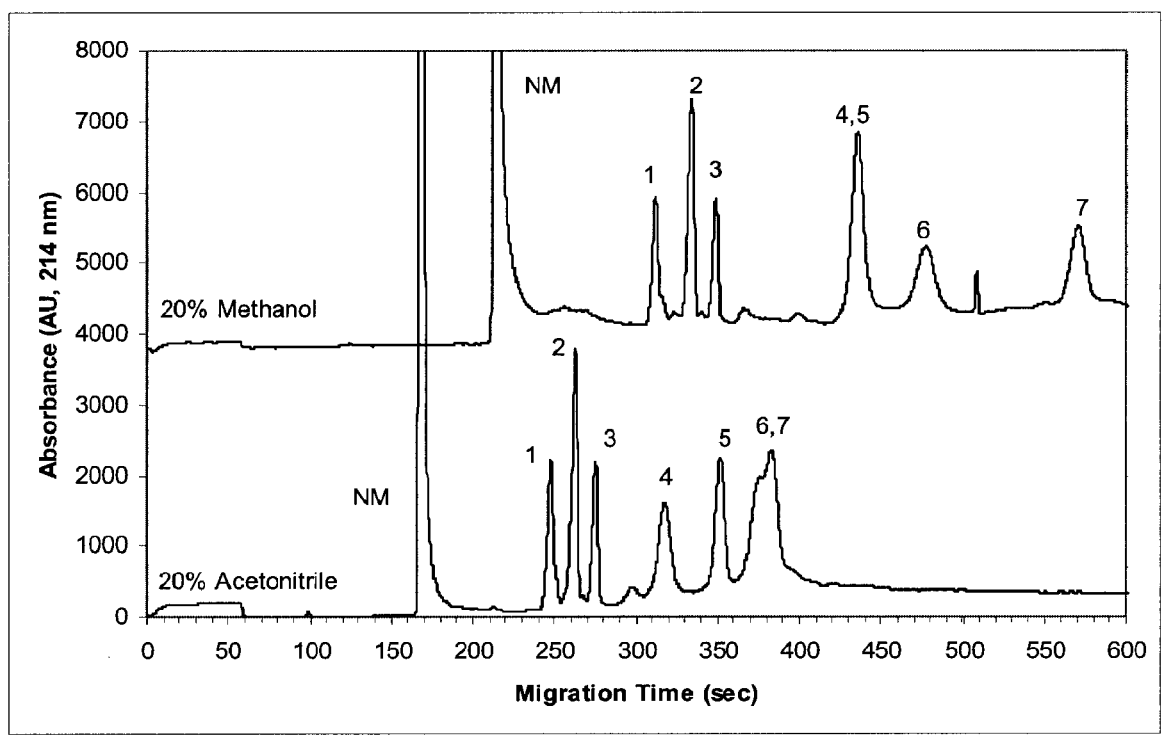
FIG. 10 shows the results of an experiment addressing the separation of a mixture of seven polypeptides in acetonitrilic (bottom trace) and methanolic (top trace) solutions conducted using a capillary electrophoresis (CE)-electrospray ionization (ESI)-mass spectrometry (MS) system.

FIG. 10 illustrates how improved separations can result in improved signal output. In particular, FIG. 10 shows the separation data of a mixture of seven polypeptides in acetonitrilic (bottom trace) and methanolic (top trace) solutions. In each case, the concentration of acetic acid was 50-70 mM. Electrophoresis was performed at 500 V/cm in a 60 cm, 50 um ID poly-MAPTAC treated capillary. Detection was by UV absorbance at 214 nm, 50 cm from the injection end. The composition was as follows: (NM) 0.001X eCAP™ Neutral Marker, (1) neurotensin, (2) angiotensin I, (3) bradykinin, (4) carbonic anhydrase, (5) ribonuclease A, (6) myoglobin, and (7) cytochrome c.

In FIG. 10, the seven polypeptides are separated approximately equally well in both acetonitrile and methanol-containing solutions; however, the later-migrating proteins are better resolved in the methanolic solution. A range of different concentrations of methanol (0-40%) and acetic acid (20-80 mM) was investigated for their ability to separate a standard set of peptides and proteins and for the stability of electrospray. It was found that using 20% methanol and 60 mM acetic acid gave the best combination of resolution, run-time, and electrospray performance.

To minimize concerns of sample-to-sample carry-over from adsorption of serum components and to improve the reproducibility of migration times from run-to-run, a capillary rinsing and conditioning procedure was developed and implemented. This procedure consists of rinsing the capillary with alkaline and acidic solutions and then conditioning the surface by flushing with water, dilute acid (60 mM acetic) and, finally, the separation buffer.

For the rinsing solutions, sodium hydroxide and hydrochloric acid were used first just as other authors have used for separations of serum components. Altria, K., *Capillary Electrophoresis Guidebook: Principles, Operation, and Applications*, Humana Press, Totowa, N.J. 1996; Paroni, R., et al., *Electrophoresis* 2004, 25, 463-468. However, it was found that even with the subsequent flushing steps, enough sodium and chloride ions were retained in the system to create detectable sodium and chloride adducts of serum components. To eliminate these undesired adducts, sodium hydroxide and hydrochloric acid were replaced with ammonium hydroxide (75 mM, pH 9.2) and formic acid (1.8 M, pH 1.6).

There are many choices for how to concentrate samples in-line in CE; for example, field-induced sample stacking (Altria, K., *Capillary Electrophoresis Guidebook: Principles, Operation, and Applications*, Humana Press, Totowa, N.J. 1996; Weinberger, R., *Practical Capillary Electrophoresis*, Academic Press, Inc., San Diego, Calif. 1993) transient isotachophoresis (Foret, F., et al., *Electrophoresis* 1993, 14, 417-428; Larsson, M., et al., *Electrophoresis* 2000, 21, 2859-2865; Smith, R. D., et al., *Anal Chem* 1990, 62, 882-899; Auriola, S., et al., *Electrophoresis* 1998, 19), in-line reverse-phase chromatography columns (Tempels, F. W. A., et al., *Anal Chem* 2004, 76; Stroink, T., et al., *Electrophoresis* 2003, 24, 897-903; Figeys, D., et al., *Nature Biotechnology* 1996, 14, 1579-1583), membrane preconcentration (Tomlinson, A. J., et al., *J Capillary Electrophor* 1995, 2, 225-233; Tomlinson, A. J., et al., *J Am Soc Mass Spectrom* 1997, 8, 15-24), etc.

The experiments performed herein provide the basis for selecting a transient isotachophoresis concentration method to improve sensitivity. The transient isotachophoresis (tITP) step was also selected for its simplicity to concentrate relatively large injection volumes of serum. As a sample, the processed serum is complex and reasonably concentrated, containing many separable components detectable by UV absorbance (214 nm). This is relevant because an in-line concentration step is applied to maximize the number of dilute species that are detectable in a background of more concentrated species.

Example 3

Figure 4:
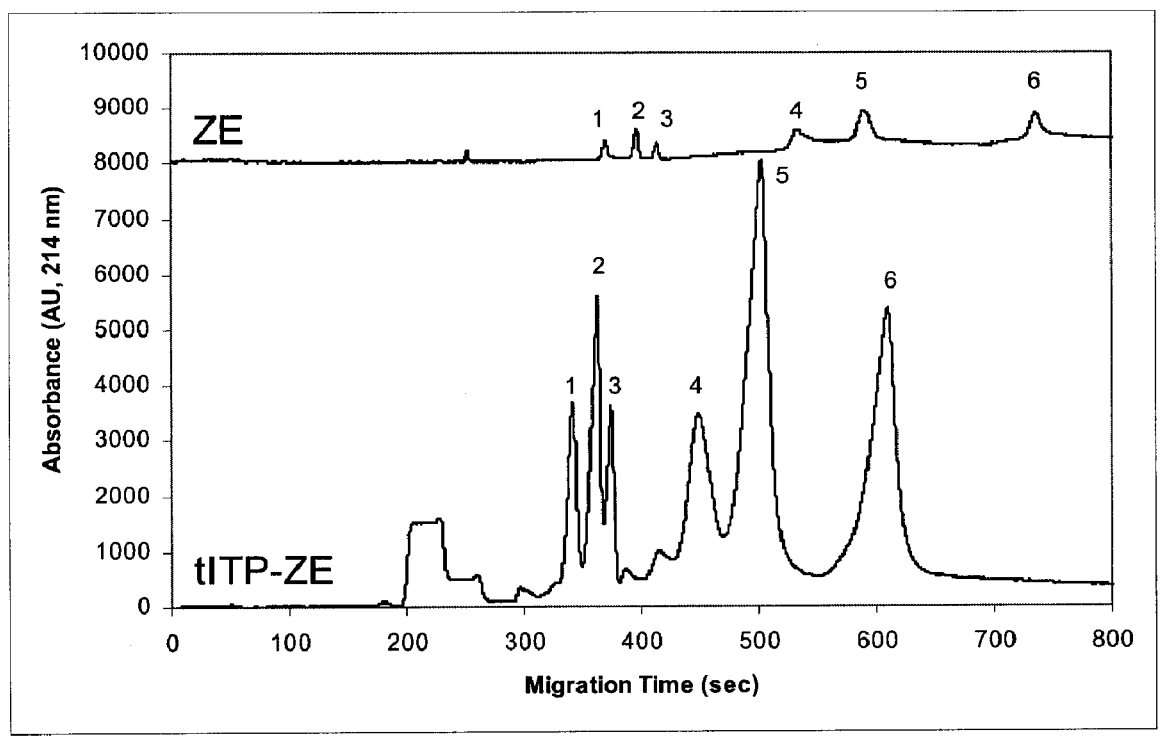
FIG. 4 illustrates results of an experiment addressing the tradeoff between signal gain and resolution for zone electrophoresis ("ZE") versus transient isotachophoresis-zone electrophoresis ("tiRP-ZE") separations conducted using a capillary electrophoresis-electrospray ionization-mass spectrometry system.

FIG. 4 demonstrates the tradeoff of signal gain and resolution for zone electrophoresis (ZE) versus tITP-ZE separations. Approximately 13-fold more sample was loaded for the tITP-ZE separation, resulting in an improvement of ten- to fourteen-fold in signal. Electrophoresis was performed in 10-30% methanol/50-70 mM acetic acid at 500 V/cm in a 60 cm, 50 um ID poly-MAPTAC treated capillary. Detection was accomplished by UV absorption at 214 nm at 50 cm from the injection end. For the ZE run, sample was injected for 6 seconds at 1 psi. For the tITP-ZE run, sample was injected for 8 seconds at 9.5 psi, followed by an 8 second, 9.5 psi injection of the stacking solution. The components of each at a flowrate of 10 ug/nL are as follows: (1) neurotensin, (2) angiotensin I, (3) bradykinin, (4) carbonic anhydrase, (5) myoglobin, (6) cytochrome c. For these analytes, the signal intensity increases approximately ten-fold upon injecting 13 times more sample and a plug of ammonia-containing separation buffer. However, it was noted that although the injected volume is stacked into a zone that gives rise to peaks that are fairly symmetrical, some resolution is lost.

A noted concern for this embodiment was whether for MS detection, the gain in total number of detectable and quantifiable species achieved by injecting more sample was offset by ion suppression resulting from the loss of electrophoretic resolution between species. An absolute answer to this question may be ascertained with a devised algorithm that counts the total number of species detected in a CE-MS run. In the absence of this algorithm during the development of this procedure, a series of CE-MS experiments were performed in which the amount of sample injected was varied and performed either by ZE alone or by tITP-ZE. It was found that a modest (as much as five-fold) increase in signal, which varied from component to component, could be obtained by injecting a relatively large amount of sample and performing tITP-ZE. Accordingly, another preferable embodiment of the invention provides a system that combines transient isotachophoresis (tITP), capillary zone electrophoresis (ZE), electrospray ionization (ESI) and mass spectrometry (MS).

The ammonia concentration (20-80 mM) and the ratio of sample-to-stacking plugs were also investigated to determine conditions for a reasonable resolution and signal gain. It was found that for a 60-cm capillary, the best signal gain with MS detection was obtained when the sample was injected for about 5 seconds at about 9.5 psi and the stacking solution (25 mM ammonium in 20% methanol/60 mM acetic acid, pH 4.7) was injected for about 5 seconds at about 4.8 psi.

Figure 5:
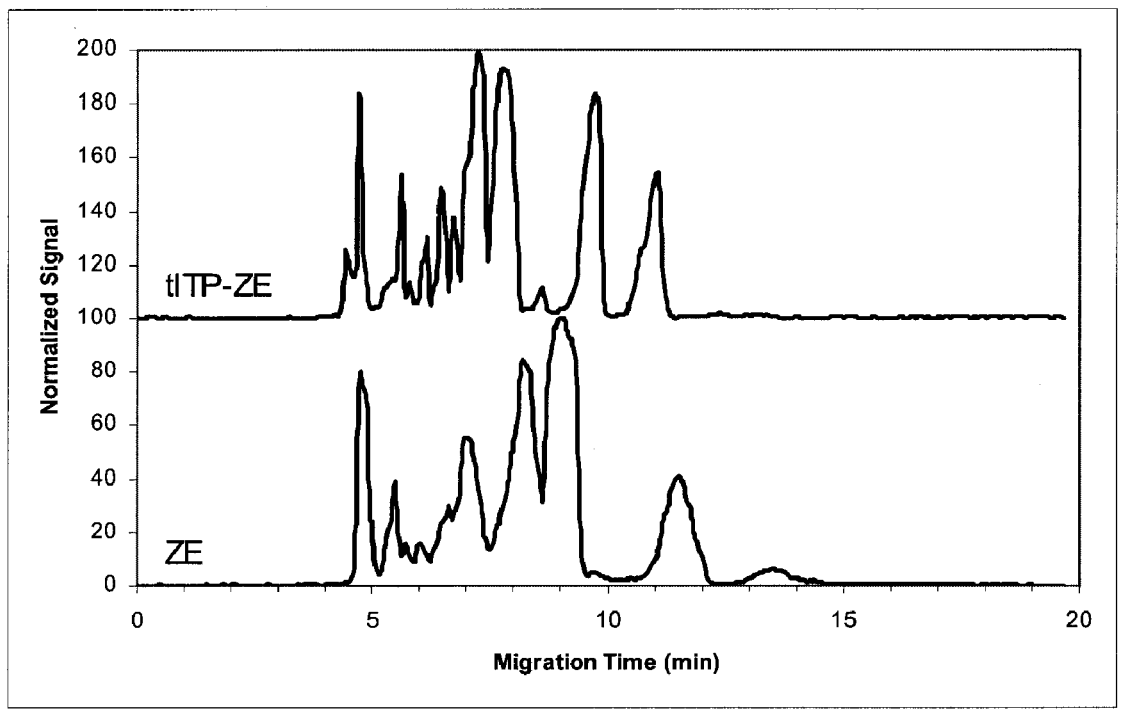
FIG. 5(a) illustrates results of an experiment comparing base peak intensity (BPI) traces for pooled human serum separated by zone electrophoresis (lower trace) and by transient isotachophoresis-zone electrophoresis (upper trace).
FIG. 5(b) illustrates overlapping results for the two separations shown in FIG. 5(a).
Figure 5:
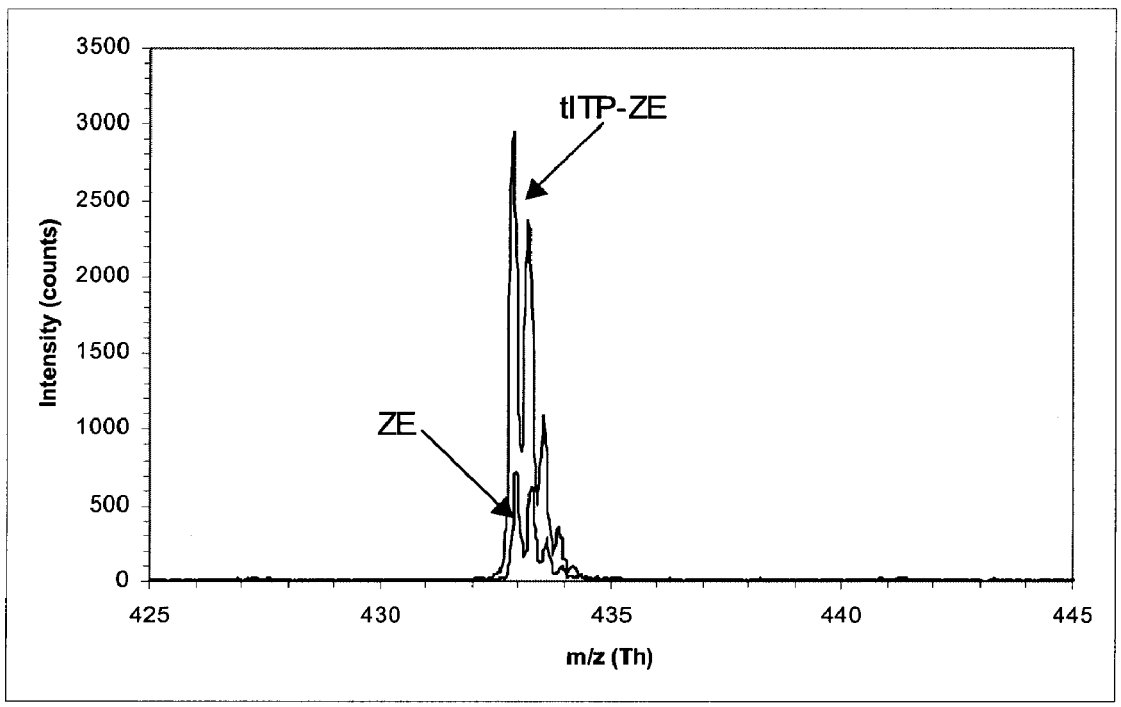

FIG. 5($a$) shows a comparison of the base peak intensity (BPI) trace for pooled human serum separated by ZE (lower trace) and that separated by tITP-ZE (upper trace). The signal displayed is relative to a value of 100 for the maximum intensity in the data set. For the data in FIG. 5, the amount of injected serum and run conditions (applied voltage, capillary, buffer etc) were the same, except that in the tITP-ZE separation, the injection of serum was followed by an injection of the ammonium stacking solution as described in the CE-ESI-MS system conditions noted above. By comparing the two BPI traces, narrower peaks are observed for the tITP-ZE separation.

FIG. 5($b$) shows a comparison of the spectra where angiotensin I (m/z 432.9) has its maximum intensity for the two separations shown in FIG. 5($a$). The spectrum for the ZE separation lies within that for the tITP-ZE separation. Angiotensin I was added to human serum before processing the serum. By extracting ion electropherograms for individual components, we find that individual components typically have a narrower peak width and a higher signal in the tITP-ZE data. For example, the maximum intensity for angiotensin I (m/z 432.9, +3 charge state) is approximately four times greater with tITP (~2950) than without (~720) ((FIG. 5$b$)).

It is believed that the mechanism of stacking is likely due to a combination of several effects. For example, the ammonium ion has a faster mobility than the serum components, and therefore the serum components should stack against the boundary with the ammonium ions for as long as ITP conditions persist local to the sample zone. Additionally, the pH of the ammonium solution is higher than that of the sample, and therefore peptides that migrate through the boundary into the ammonium zone may become less positively charged and slow, also causing the stacking to occur at the boundary with the ammonium zone.

The following three techniques were tested to apply the voltage to the fluid in the emitter: (1) the use of a distally coated emitter from New Objective (2) the use of a stainless steel union to join the emitter and capillary and (3) the use of a t-junction in which a platinum or palladium wire was inserted perpendicular to the capillary-emitter axis. The metal union was easy to assemble and use; however, several undesired contaminant peaks were observed when performing CE-MS, and this was hypothesized to arise from iron-acid interactions. Furthermore, the t-junction was found to be less robust than the distally coated emitters from New Objective.

Emitters where the tip was drawn to a smaller inner diameter at the end (SilicaTips) and emitters where only the external (outer) diameter is tapered (TaperTips) were utilized. Tips with inner diameters of 8-30 um were prone to clogging. It was found that an externally tapered tip with 50 um ID (equivalent to the ID of the separations capillary) worked best. The internal surface of the emitter was also cleaned and coated with poly(MAPTAC) to match the surface coating in the separations capillary. To extend the lifetime of the emitter to between one and five days of constant use, a careful procedure was developed to cut, trim and clean the emitter. Rinsing of the emitter with acetone to remove adherent material from the packaging and examining the emitter end for a clean, perpendicular cut with no damage to the coating were found to be critical. For the best or optimal signal observed, the emitter was positioned on-axis with the inlet capillary of the assembled mass spectrometer, and the tip was placed approximately 1-5 mm from the MS inlet.

In the exemplary embodiments of the invention described herein, samples were run through a selected CE system before reaching the interface between the capillary and the electrospray emitter. For sheathless electrospray interfaces as described elsewhere, the separations capillary can be coupled directly to the electrospray emitter by means of a junction or by fabricating the spray tip from the end of the separations capillary. The spray voltage can be supplied either at the junction or at the tip of the emitter. It was observed that when the spray voltage is applied to the tip end of a frontally coated electrospray emitter (SilicaTips, New Objective), frequent electrical arcing from the emitter to the metal curtain gas plate on the ABI Mariner occurred. The arcing destroyed the conductive coating and rendered the emitter useless. Therefore, the frontally-coated emitters were abandoned in favor of applying the voltage at the junction between the separation capillary and the emitter.

Example 4

Experiments were performed to assess to what extent serum samples could be distinguished and classified based on patterns of component intensities. A total of 76 CE-MS analyses were planned on 18 individual human serum samples and 8 pooled serum samples. Each sample was analyzed two to five times, in random order. Pooled serum samples were made by combining an aliquot of each individual sample to eliminate effects caused by biological variability between individuals. One of two specific sets of 13 polypeptide standards in predetermined amounts were added to each sample, creating two sample groups: A and B. The final concentration of each polypeptide in each sample group is given in Table 3.

TABLE 3

| Type | Component | Group A nM | Group B nM | Fold |
|---|---|---|---|---|
| Pre-processing standard | Insulin β-chain | 500 | 500 | 1 |
| | Ubiquitin | 200 | 200 | 1 |
| Post-processing standard | Lysozyme | 100 | 100 | 1 |
| | Neurotensin | 100 | 100 | 1 |
| Pattern recognition standard | Angiotensin I | 10 | 100 | 10 |
| | Angiotensin III | 100 | 800 | 8 |
| | Aprotinin | 50 | 150 | 3 |
| | Bradykinin | 100 | 200 | 2 |
| | Insulin | 500 | 25 | 20 |
| | LHRH fragment | 150 | 750 | 5 |
| | Mellitin | 1000 | 100 | 10 |
| | Renin substrate | 25 | 250 | 10 |
| | Substance P | 1000 | 250 | 4 |
| Total Spiked Concentration: | | 2935 | 2625 | |

Two components, neurotensin and lysozyme, were added after sample processing and before CE-MS analysis as standards that could be used to characterize the performance of the CE-ESI-MS methodology. These components, the post-processing standards, were added to a final concentration of 100 nM in each sample. All other peptides and proteins were added before any processing was performed on the serum sample. Two of these, ubiquitin and insulin β-chain, were added to each sample at 200 nM and 500 nM, respectively, in the starting serum volume. The other nine peptides and proteins were added at different levels in Group A samples than in Group B samples to emulate a different pattern of peptide concentrations between the two groups. The difference in concentration of each of the nine 'pattern recognition standards' between the two groups varied from two to twenty-fold. The concentrations in Group A and Group B were chosen so that similar total molar amounts of peptides were added to each group of samples.

The CE-MS runs were performed in an automated mode with analytical systems provided in accordance with other aspects of the invention. Each of ten samples were loaded into an autosampler at a time. All of the post-processing standards and pattern recognition standards were added to the samples before the start of the experiment. The samples were stored at −20 C until they were run and in between repeat analyses. At the start of every day during experimentation, the system was conditioned with three runs of a standardized serum sample, and then a standard set of ten peptides was run to monitor the separation performance and signal intensity. If fluid wicked back along the emitter tip, or if the signal could not be brought to within 10% of the typical signal for the set of ten peptides, the emitter was discarded and replaced with a new one.

Figure 6:
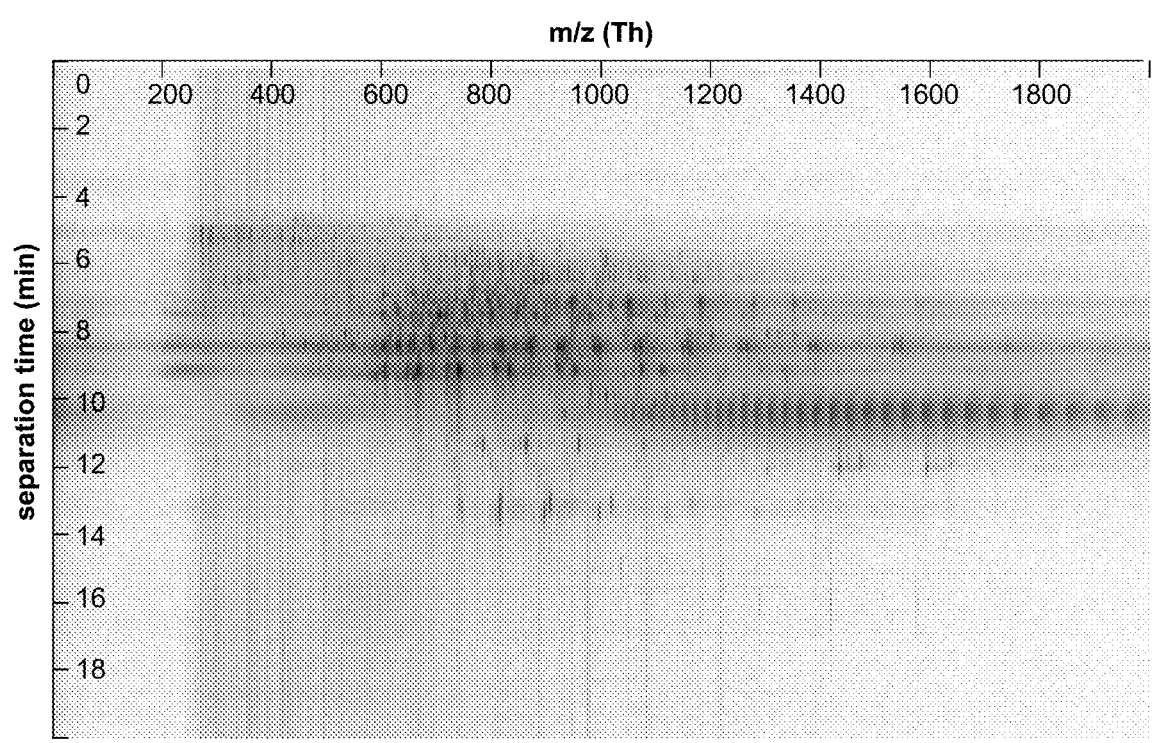
FIG. 6 represents the CE-MS data illustrated in a two-dimensional (2-D) format, similar to that obtained through 2-D polyacrylamide gel electrophoresis (PAGE). The x-axis represents the mass-to-charge ratio and the y-axis represents the separation time. Mass spectra are acquired as components come out of the capillary or chip. Black regions represent mass-to-charges and separation times where components are observed. White regions represent those were no components are observed.

FIG. 6 represents the CE-MS data for human serum in a 2-D format, similar to that of a 2-D PAGE gel. Black regions of the illustration generally correspond to relative high intensity. Each vertical segment represents a single charge state of a component. Proteins can be recognized by their charge envelopes, which appear as a set of lines spaced in the m/z axis. Data was collected for an individual serum sample during the pattern recognition experiment. The illustration provided depicts one of the runs of individual sera displayed in a "pseudo-2D-gel" format, with m/z increasing from right to left, and separation time increasing from top to bottom—relatively black regions indicating high intensity and relatively white regions indicating zero intensity. However, unlike in a typical image of a 2-D protein gel, each serum component in this separation may give one or more spots or lines, according to the number of charge states detected. When employing more enhanced graphics to view results with even greater resolution, resulting images other than those shown herein as examples could further display the isotopic resolution of the components.

In general, only one or two charge states are detected for smaller peptides such as neurotensin, whereas multiple charge states are observed for proteins, such as residual human serum albumin.

Figure 7:
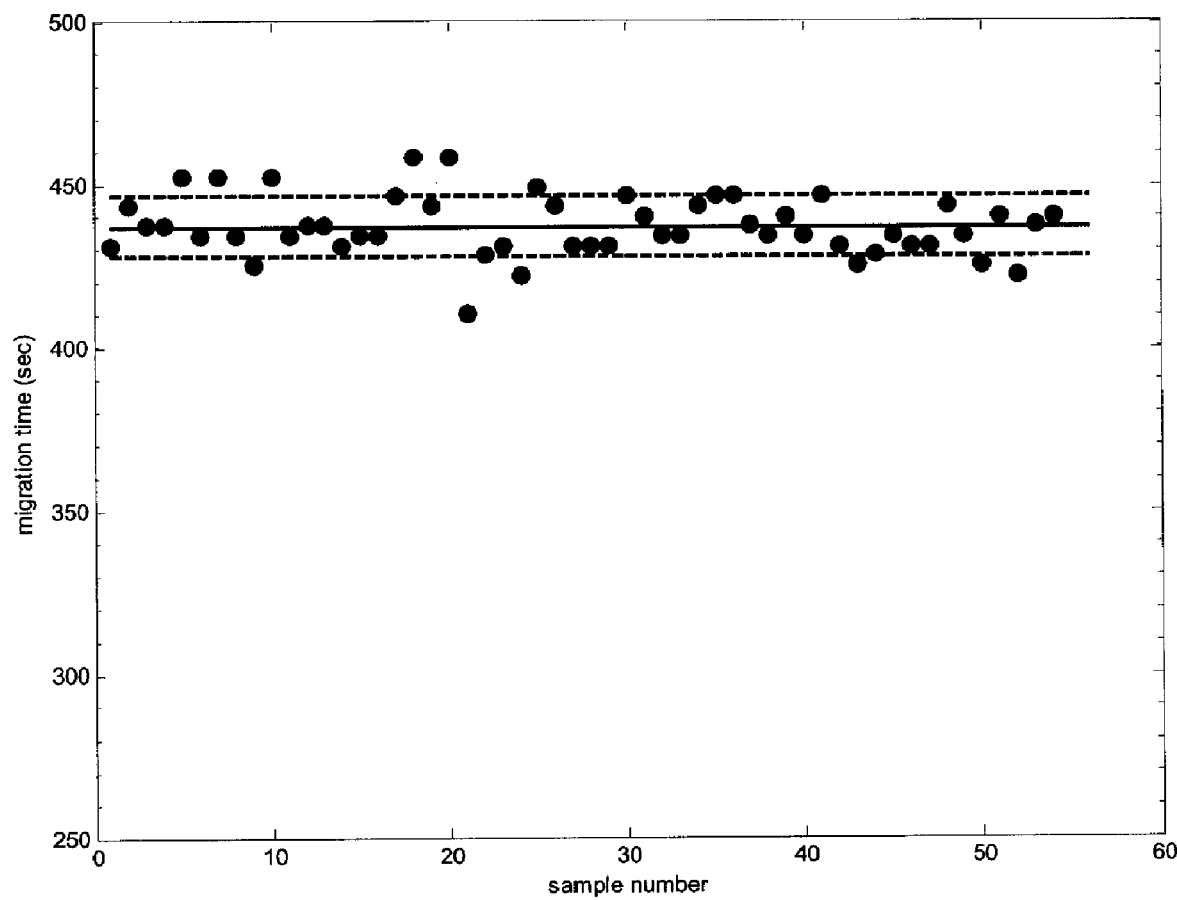
FIG. 7 illustrates the migration time of neurotensin, one of the post-processing standards, plotted as a function of run order.

In FIG. 7, the migration time of neurotensin, one of the post-processing standards, is plotted as a function of run order. The solid horizontal line denotes the mean value, and the dotted lines denote the bounds of one standard deviation. The average migration time is 436.5+/−9 seconds. Most of the data lies within one standard deviation of the mean. Furthermore, the migration times are distributed more or less randomly with run order, indicating that the tITP-ZE methodology is performing equivalently throughout the experiment.

It was investigated whether there was a correlation of the data with the day a sample was run. For the pre- and post-processing standards, which are present in the same concentration in each sample, we calculated a total intensity, akin to the area of a single-component peak in an electropherogram. Where more than one charge state was detected for a component, the two most prevalent charge states were summed over. Then the total intensity against run order was plotted and no obvious grouping of the intensities by day was found.

As described above, the pattern recognition standards were added to the serum samples such that the difference in their concentration between the two groups spanned from 2 to 20-fold.

Example 5

Figure 8:
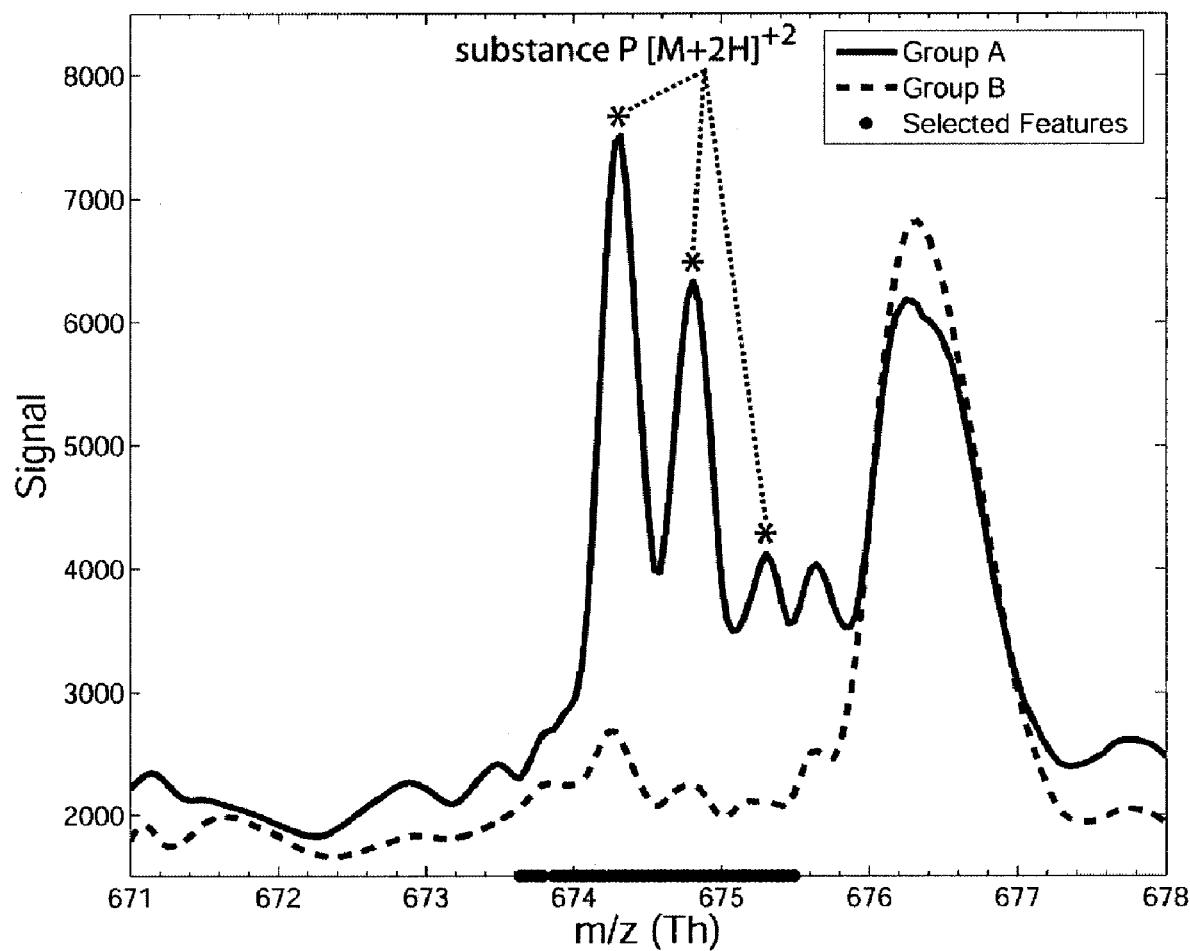
FIG. 8 illustrates the average mass spectra results for substance P (m/z 674.4, +2 charge state) where the difference in concentration between selected Groups A and B was 4-fold.

FIG. 8 provides example data for Substance P, which was added into samples in Group A at a 4-fold higher concentration than into samples in Group B, is shown. The graph provided shows the mathematically averaged mass spectra for Group A (solid line) and for Group B (dotted line). Black circles on the x-axis identify the values of m/z determined to be distinguishing features by our support vector machine (SVM)-based feature selection algorithms. These features are adjacent to each other (the black circles appear as a line) and correspond to the m/z for the first three isotope peaks of Substance P in its doubly charged state. The difference in average signal is easily discernable by eye. Immediately to the right of the isotope envelope for Substance P is an unidentified serum component (m/z 676.4), whose intensity was not significantly different between the two sample groups and was therefore identified correctly as a non-distinguishing feature.

To determine the fold-difference in concentration that was detected among the samples, the mean total intensities for each standard over all runs of Group A samples and the mean total intensities for each standard for all runs of Group B samples were used. Then, for each standard, the total intensities of that standard in Group A were compared to those in Group B by performing a student's t-test. The result of the t-test is a p-value which indicates the probability due to chance of the difference in means for Groups A and B. For example, if the p-value is 0.5, there is a 50% chance that the observed difference in mean values is due purely to chance and, hence, one would conclude that there is no statistically significant difference between the means. Conversely, a p-value of 0.0001 indicates there is a statistically significant difference between the means because there is only a 0.01% chance that this could have occurred by happenstance.

The following Table 4 shows the p-values for all standards analyzed, the observed (detected) fold difference, and the expected fold difference in concentration for all of the polypeptides added to the sera. The observed fold differences for the pre- and post-processing standards range from 1.05 to 1.30, close to the expected value of 1.0, as these standards are present at the same concentration in Group A and Group B. In particular, there was only a 5% difference between the mean total intensities for neurotensin, and the p-value for this difference was greater than 0.5. Two of the post-processing standards, neurotensin and lysozyme, have p-values an order of magnitude higher than those of the pre-processing standards, ubiquitin and insulin β-chain. Therefore, it is likely that ubiquitin and insulin β-chain are more sensitive to an unidentified effect correlated to the two groups of samples (e.g. the additional peptides spiked into each group). The significance of these results may be further considered with additional data.

TABLE 4

| Standard | t-test p-value | Observed Fold | Expected Fold |
|---|---|---|---|
| pre-processing | | | |
| Insulin β-chain | 0.04712 | 1.3 | 1 |
| Ubiquitin | 0.01436 | 1.3 | 1 |
| post-processing | | | |
| Lysozyme | 0.33615 | 1.2 | 1 |
| Neurotensin | 0.71149 | 1.0 | 1 |
| pattern recognition | | | |
| Angiotensin I | 0.00001 | 7.6 | 10 |
| Angiotensin III | 0.00000 | 6.3 | 8 |
| Aprotinin | 0.00003 | 1.9 | 3 |
| Bradykinin | 0.00000 | 1.6 | 2 |
| Insulin | 0.00000 | 13.4 | 20 |
| LHRH fragment | 0.00000 | 4.5 | 5 |
| Mellitin | 0.08071 | 3.8 | 10 |
| Renin substrate | 0.00000 | 7.8 | 10 |
| Substance P | 0.00000 | 3.4 | 4 |

As explained above, the p-values are less than 0.0001 for all pattern recognition standards except mellitin. Therefore, with the exception of mellitin, the differences in mean total intensities between the groups are statistically significant. There was a 1.6-fold difference in the mean total intensities for Group A and B for bradykinin, which was spiked in at twice the concentration in Group B than in Group A. Therefore, the system provided in accordance with this embodiment of the invention is capable of detecting at least a two-fold difference in the average concentration of a component in two groups.

Example 6

The results in the preceding sections suggests that if a particular component (a biomarker, for example) has at least a two-fold different concentration on average between the two groups, the difference can be detected and quantified with reasonable accuracy and certainty. A desired goal of the experimentation conducted was to determine whether it was possible, without a priori knowledge of the markers, to automatically identify the pattern recognition standards as those and only those features which differentiate Groups A and B, and furthermore, whether classification of samples as belonging to Group A and Group B was possible using the pattern recognition algorithm.

The pattern recognition algorithm selected was based on the use of support vector machines (SVM) on signal-processed data. (Boser, B. E., et al., In *Computational Learning Theory*, 1992, pp 144-152; Christianni, N., et al., An introduction to support vector machines, Cambridge University Press, 2000; Vlapnik, V., *Statistical Learning Theory*, John Wiley and Sons, 1998.)

The result of signal processing was a single intensity vs. m/z spectrum for each CE-MS run. The raw data was processed by first removing noise from the m/z spectra via wavelet transformation. (Donoho, D. L., *Applied and Computational Harmonic Analysis* 1995, 2, 101-126.) Then, the intensity for each m/z over all spectra collected during the run were summed, effectively 'collapsing' the data over separation time.

After signal processing, support vector machines were used in an iterative manner to identify and select those features (i.e. m/z values) that differentiate Group A from Group B. The signal-processed data was divided into two sets: a "training set" and a "test set." Within the training set, the data was sub-divided by group, since it is known which samples belong to Group A and which belong to Group B. The SVM algorithm was then run on the training set. The result is a weights vector which indicates the relative importance (weight) of each m/z in differentiating Group A from Group B. Next, the training set of data was 'updated' by taking the dot product of the weights vector and the raw data. SVM is run on the updated data, forming a new weights vector. The process of running SVM to form a new weights vector and updating the data was repeated so that the only features (m/z values) retained are those which best distinguish the groups. These features were the selected features that make up the distinguishing pattern.

The final step in this process was to classify a sample as belonging to either Group A or Group B. To do this, all the original, raw data is reduced so that for each CE-MS run, the only intensities that remain in the data set are those that correspond to the selected features. The SVM is run one last time with the data reduced in this manner to give the weights vector which may be used to classify samples (the classification rule). All the samples in the test set are classified by forming the dot product of the classification rule with the reduced data for each sample and examining the sign of the product. If the sign is positive, the sample belongs to Group A, and if negative, the sample belongs to Group B.

To estimate how well data could be classified, a three-fold cross validation study was performed. Cross-validation based on multiple folds (groupings) is a statistical technique that has been shown to be a reliable empirical method to estimate the error of an algorithm. Efron, B., *J. Amer. Statist. Assoc.* 1983, 78, 316-331; Stone, M., et al., *J. Roy. Statist. Soc.* 1974, 36, 111-147.

The data was randomly separated into three sets: 1, 2, and 3. Sets 1 and 2 were combined to form the training set (as discussed above). The remaining set, set 3, was the 'test set,' the set of data that would be classified. In this way, the data used to develop the algorithm is independent from that used to test the algorithm, and therefore the statistics on the accuracy of the algorithm are more indicative of how the algorithm performs on a much larger, more general data set. Stone, M., *J. Roy. Statist. Soc.* 1974, 36, 111-147. The process of feature selection and sample classification was repeated twice more so that each of the three sets of samples was used as the test set, completing the three-fold cross validation.

Table 5 below provides the results of the feature selection for the components added to serum for each of the three sets of data.

TABLE 5

| Type | Component | Set 1 | Set 2 | Set 3 |
|---|---|---|---|---|
| Pre-processing standard | Insulin β-chain | − | − | − |
| | Ubiquitin | − | − | − |
| Post-processing standard | Lysozyme | − | + | − |
| | Neurotensin | − | − | − |
| Pattern recognition standard | Angiotensin I | + | + | + |
| | Angiotensin III | + | + | + |
| | Aprotinin | − | + | + |
| | Bradykinin | + | + | + |
| | Insulin | + | + | + |
| | LHRH fragment | + | + | + |
| | Mellitin | + | + | + |
| | Renin substrate | + | + | + |
| | Substance P | + | + | + |

A plus sign appears in the table where a component was identified as a distinguishing feature, and a minus sign appears where a component was not identified as a distinguishing feature. It is therefore expected that the minus signs for all the table entries for pre- and post-processing standards, as those components were added to Group A and Group B samples in equivalent amounts. It would also be expected that plus signs in the rows for the pattern recognition standards, as the concentrations of these components differed between the groups. Out of the three sets of data and the nine pattern recognition standards, in only one instance (aprotinin in set 1) was a pattern recognition standard not identified as a distinguishing feature. In only one instance also (lysozyme in set 2), a post-processing standard was identified as a distinguishing feature.

Using the classification rule based on identified features, the samples in each of the three test sets were assigned to either Group A or Group B. The accuracy obtained was determined to be approximately 94%.

Example 7

Samples

Individual human serum samples were obtained from Golden West Biologics (Temecula, Calif.).

Samples were prepared by adding thirteen polypeptides as mock biomarkers at pre-determined levels to two groups of human sera. Because the targets of the biomarker discovery experiments herein were peptides and small proteins, a procedure was developed to deplete the serum of proteins larger than 50,000 MW. This step effectively removed the majority of the high abundance proteins such as serum albumin and immunoglobulins G which could have overwhelmed the lower abundance peptides of interest. Eight proteins alone constitute approximately 90% of the 60-80 milligrams of protein per milliliter of serum (Burtis, C. A., et al., *Tietz Textbook of Clinical Chemistry*, W.B. Saunders Company, Philadelphia, Pa. 1999; Putnam, R. W., *The plasma proteins*, Academic Press, New York 1975); and therefore the high-abundance proteins are of less interest. This procedure also effectively de-salts the sample to reduce the conductivity of the sample and to avoid the possible formation of salt adducts in the electrospray.

The procedure consisted of diluting 50 µL of human serum ten-fold and filtering the diluted serum through an Amicon YM50 (Millipore Corporation, Billerica, Mass.) molecular weight cut-off membrane at about 14,000 g for 10 to 40 minutes at room temperature. After centrifugation, 15 to 35 µL of 5-12% trifluoroacetic acid was added to the filtrate, and the filtrate was loaded onto a pre-equilibrated, C8 reverse-phase Optiguard guard column (Optimize Technologies, Oregon City, Oreg.) at 70-90 µL/min. The column was washed with 150-250 µL of 3-7% acetonitrile/0.1-0.5% acetic acid to remove salt, and the serum components are eluted with 15-25 µL of 60-80% acetonitrile/0.1-0.5% acetic acid. The column may be re-used after rinsing with 90-99% acetonitrile and equilibrating with 3-7% acetonitrile/0.1-0.5% acetic acid.

Materials

Various materials and reagents were selected and obtained from different sources such as the following: glacial acetic acid (99+%), formic acid (96%), 5.02 N ammonium hydroxide volumetric standard, ammonium persulfate (APS), 7-oct-1-enyltrimethoxysilane, 3-methacryloylaminopropyl trimethylammonium chloride (MAPTAC), and N, N, N', N',-tetramethylethylenediamine (TEMED), human angiotensin I, angiotensin III, bovine lung aprotinin, bradykinin, bovine heart cytochrome c, bovine pancreatic insulin β-chain (oxidized), bovine pancreatic insulin, chicken egg white lysozyme, luteinizing hormone releasing hormone fragment 1-6 amide, melittin, equine skeletal myoglobin, neurotensin, porcine N-acetyl renin substrate tetradecapeptide, substance p, and bovine erythrocyte ubiquitin were purchased from the Sigma-Aldrich Company (St. Louis, Mo.). GC-MS grade methanol, HPLC-grade acetonitrile, high purity acetone and HPLC-grade water were obtained from Honeywell Burdick and Jackson (Muskegon, Mich.). Trifluoroacetic acid and 10 M sodium hydroxide were obtained from JT Baker (Phillipsburg, N.J.). eCAP™ Neutral Marker was obtained from Beckman Coulter, Inc. (Fullerton, Calif.) and diluted 100-fold in acetonitrile.

Results

The efficacy of this procedure was determined using HPLC with W detection. More than 99% of the high abundance proteins were removed. To gain an additional measure of the recovery of lower molecular weight peptides, a set of standard peptides was added to the serum at a known concentration. Recovery of endogenous and spiked peptides varied by peptide; in general, endogenous peptides were recovered at more than 70% (range: 65%-100%) and spiked peptides were recovered at more than 85% (range: 70-100%) (data not shown).

Example 8

Figure 15:
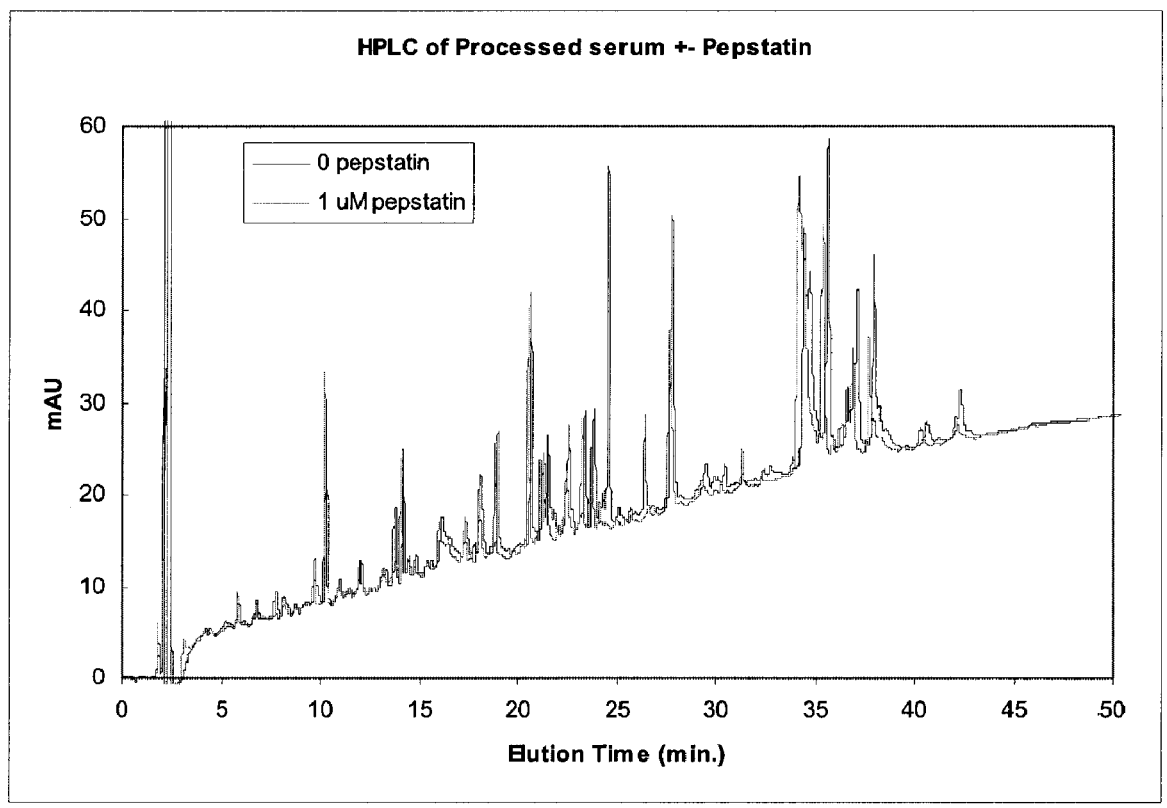
FIG. 15 illustrates a mass spectrum comparison of a serum sample processed with and without pepstatin A.

A 50 µL sample of human serum is processed with or without the addition of 5 µL pepstatin A (a 1 mM solution of pepstain A prepared in methanol diluted 1:10 in water). Samples with and without pepstatin are added to 50 µL of 10% formic and the sample is diluted to 500 µL with water and added standards if desired. Each sample was passed over a gradient C18 column using an acetonitrile gradient and monitored at 215 nM in an Agilent™ 110 as shown in FIG. 15. Examples of affected components are illustrated in FIG. 15 as indicated by the arrows.

Figure 16A:
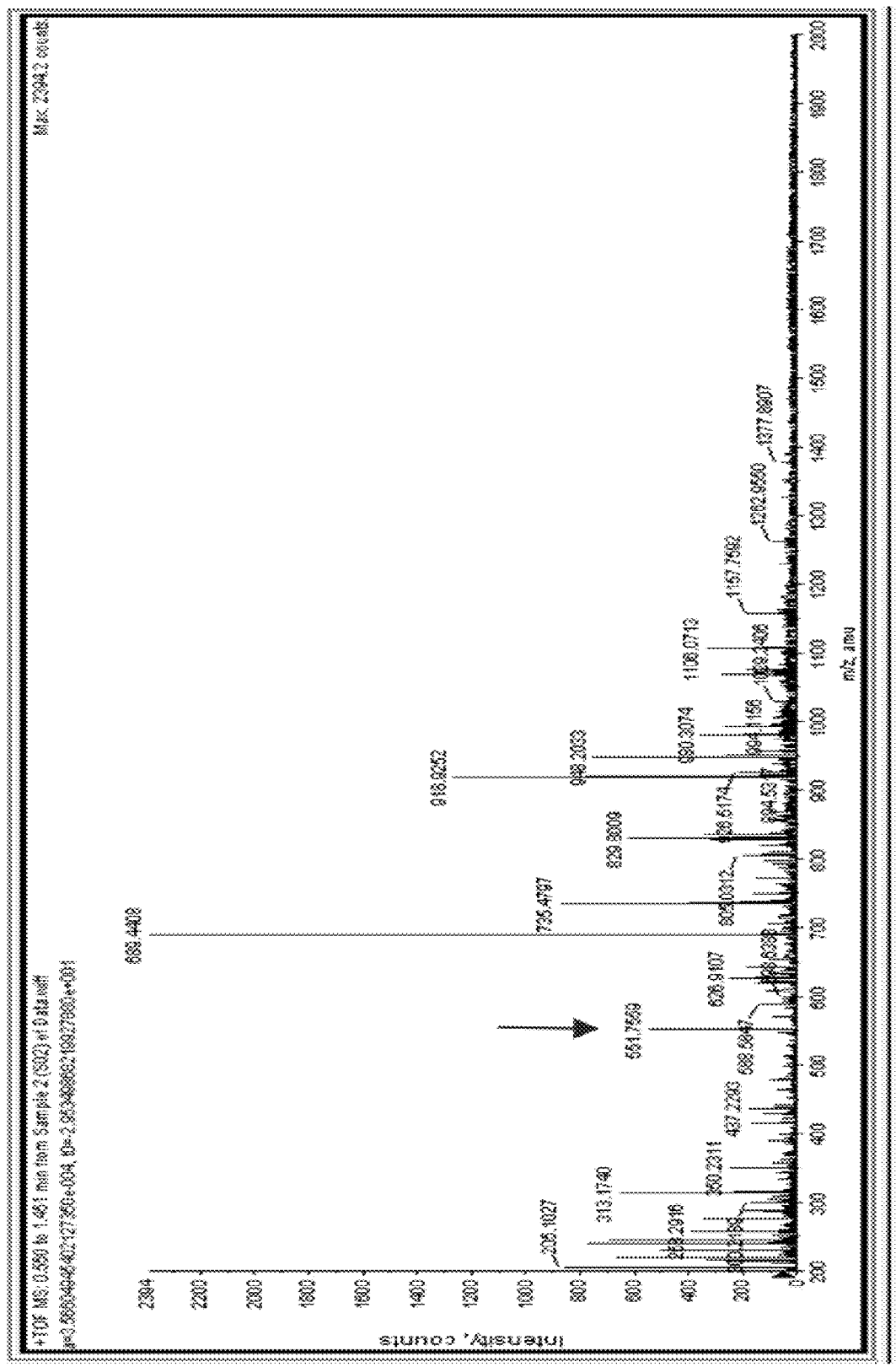
FIGS. 16A and 16B illustrate mass spectra of a sample without pepstatin A (FIG. 16A) and with pepstatin A (FIG. 16B).
Figure 16B:
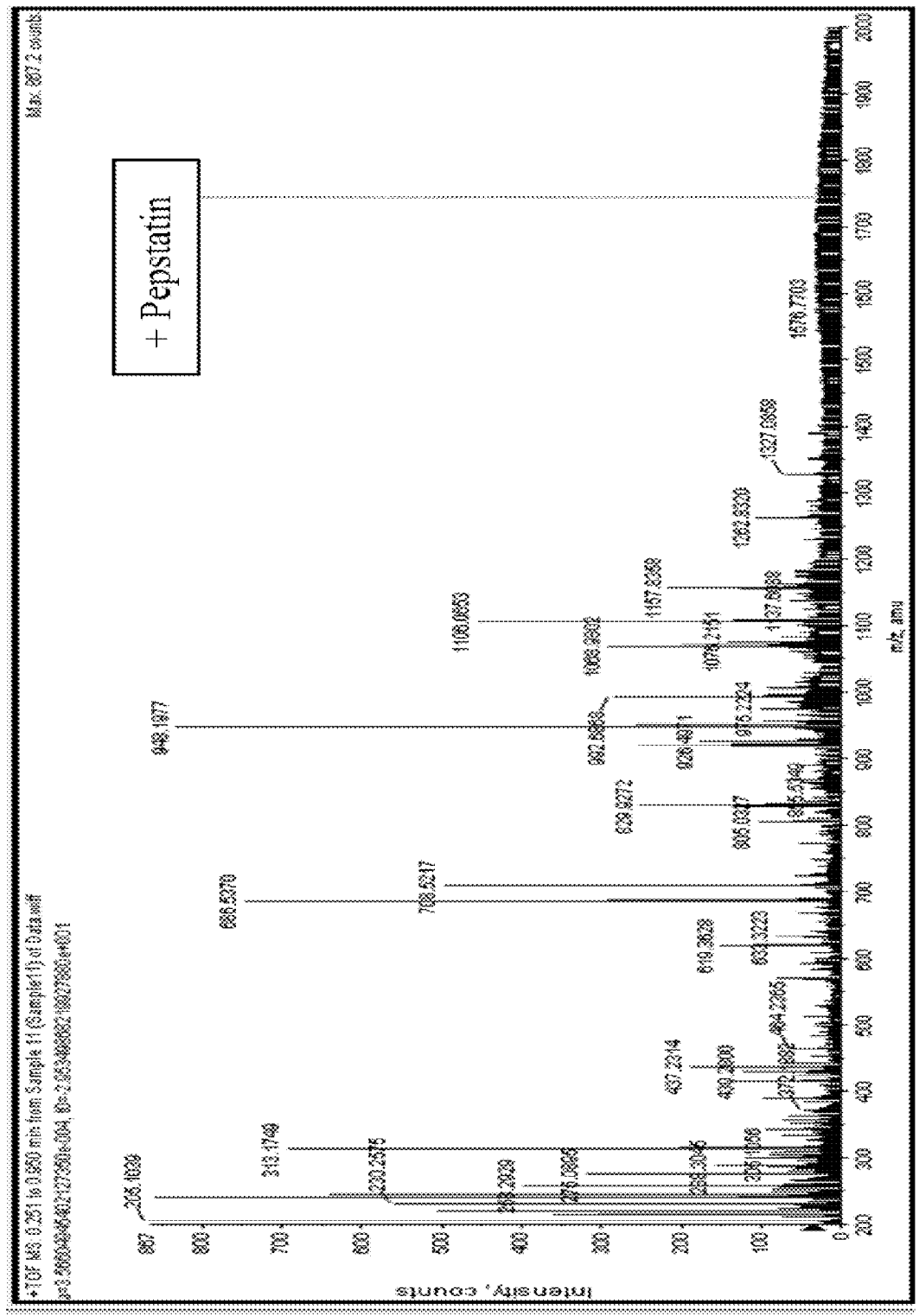

A serum sample was processed with or without 0.1 µM pepstatin A as described above and each sample was infused by electrospray using Nanomate™ instrument (Advion, Inc.) linked to a QStar™ mass spectrometer with the results shown in FIG. 16(a) (without pepstatin) and 16(b) (with pepstatin). A component affected by the addition of pepstatin is indicated with an arrow.

Example 9

Microfluidic-based capillary electrophoresis-mass spectrometry was used to identify prostate cancer markers. The objective was to find patterns which differentiate those individuals with prostate cancer from those without in subjects with a PSA value between 1-6 ng/ml.

Study Design

Samples were divided into discovery and validation sets. Data was collected from both sample sets concurrently. Data from the discovery samples was used to find a biomarker pattern, and data from the validation samples was used to evaluate how well the pattern can distinguish between the two groups of men (i.e. the validation data set was not used for training or testing in discovery cross-validation). Data was analyzed from each site's samples independently and then evaluated for overlap between the results. Table 6 provides a description of the samples and FIG. 17 provides a schematic overview of the samples.

Figure 17:
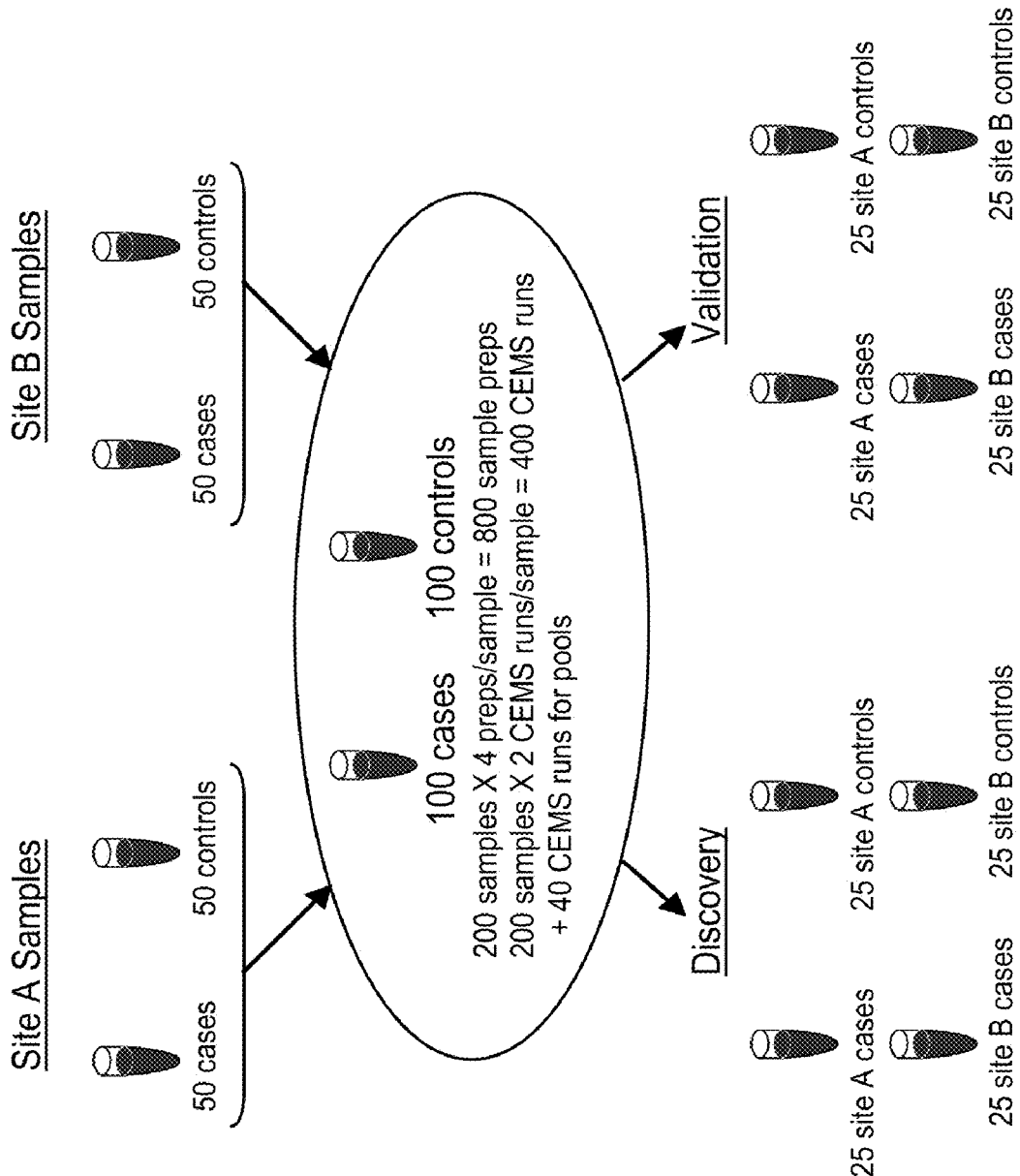
FIG. 17 is a schematic representation of the experimental design.

Half of the 200 samples shown in FIG. 17 were used for Discovery of patterns, as described above. These included 25 case and 25 control samples from site A and 25 case and 25 control samples from site B. Following pattern discovery, the second half of the 200 samples shown in FIG. 17 were used for validation of the patterns. Validation consisted of determining whether, for each sample, a pattern correctly identifies the sample as prostate cancer (case) or non-prostate cancer (control), using the decision function, D, described above.

TABLE 6

| Sample | Sites | |
| --- | --- | --- |
|  | Site A | Site B |
| Disease Cases | 50 | 50 |
| Control Cases | 50 | 50 |

Sample Analysis

Serum samples were prepared, separated, and introduced into a mass spectrometer for analysis. Preparation included the removal of high abundance proteins, addition of preservatives and calibrants, and desalting. Prepared samples were then separated using microfluidic based capillary electrophoresis (CE) in a ~12 minute separation. Using an electrospray ionization (ESI) interface, samples were ionized and sprayed directly into a time-of-flight mass spectrometer (MS). The resulting CE-MS data for each sample was a series of mass spectra, acquired during the electrophoretic separation. Samples were prepared and analyzed in a randomized order to minimize biases.

Sample Criteria

Samples were collected pre-biopsy and pre-treatment, and samples were collected either before or after DRE. If a DRE had been performed, samples were collected at least 24 hours post-DRE.

Matching of cases and controls was done based on site, PSA levels, age at sample collection, date of sample draw, and race, in that order of priority.

A volume of approx. 10 cc of venous blood was drawn in serum tubes ("red or marble" top glass tube, BD Vacutainer. After sitting for minimum of 30 minutes to a maximum of 12 hrs the sample was centrifuged and the serum was collected and frozen (−80° C.).

Approximately 200 µL of serum was required for analysis from each patient.

TABLE 7

| Inclusion and Exclusion Criteria | | |
| --- | --- | --- |
| | Cases | |
| Objective | Inclusion | Exclusion |
| 1 | PSA values in the 1-6 ng/ml range who have a confirmed diagnosis of prostate cancer. Reasons for biopsy of these individuals may include rising PSA, abnormal DRE, or high-risk status (e.g., family history of prostate cancer). | Prior to entering this study history of any other cancer, other than non-melanoma skin cancer. <40 years old Samples that have undergone more than 1 freeze/thaw cycle. |

Prostate cancer diagnosis was based on pathological analysis of at least one 6-core TRUS guided biopsy.

To be considered a control, patients had at least one 6-core TRUS guided biopsy that did not find evidence of prostate cancer.

Control Samples

Spiked serum A was a control run at the beginning of each day. This consisted of serum that had been processed following the standard sample prep protocol and spiked with components at specific concentrations post processing. Composition can be found in Table 8.

TABLE 8

Spiked Serum A components

| Standard | Concentration (nM) | |
|---|---|---|
| | Effective concentration in unprocessed serum | Actual concentration in resuspended serum |
| Pre-Processing Ala-met enkephalin | 100 | 1000 |
| Post-Processing | | |
| LHRH fragment | 300 | 3000 |
| Bradykinin | 300 | 3000 |
| Angiotensin III | 300 | 3000 |
| Ubiquitin | 300 | 3000 |
| Aprotinin | 300 | 3000 |
| Renin | 300 | 3000 |
| Neurotensin | 50 | 500 |

Sample Preparation and Data Collection

Each sample was prepared 4 times and run 2 times on the CE-MS.

The 200 samples were prepared four times each. The 4 replicates of each prepared sample were pooled and re-divided into 4 aliquots. Two of those aliquots were used in CE-MS.

Figure 18:
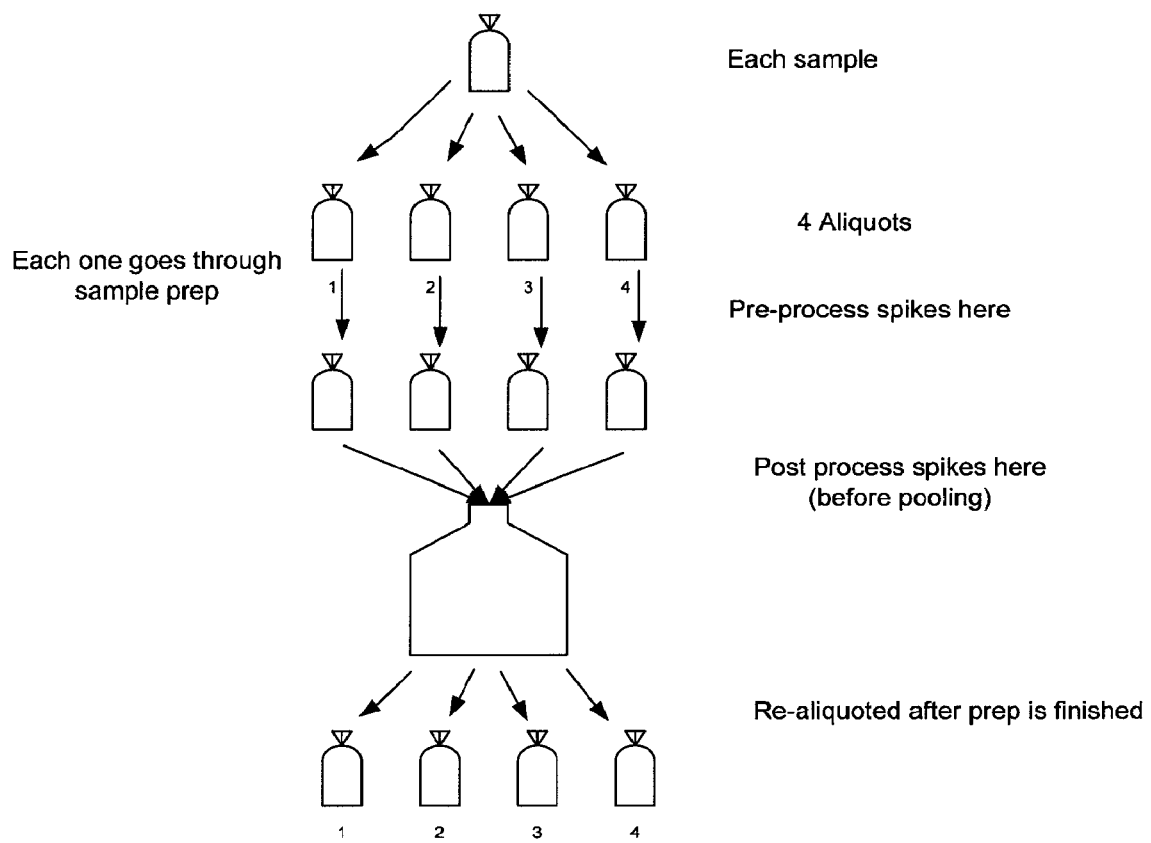
FIG. 18 is a schematic representation of an embodiment of the sample preparation process.

The standard sample preparation is outlined in FIG. 18. The composition of Sample Standard was 0.30 µM angiotensin III and 10.0 µM Aprotinin and Sample Diluent was 390 µL HPLC water, 50 µL 10% formic, 5 µL Pepstatin 1:10 in $H_2O$, 5 µL Sample Standard.

Samples were thawed sample for the run at room temperature and transferred to ice at once when thawed. Runs were set up in duplicate on each of two µElute plate (n=4 each sample). All samples were run individually. 450 µL of sample diluent was added to 50 µL of serum sample and mix. Diluted samples were transferred immediately to YM50 Microcon (within ten minutes) and centrifuged at 13,000×g for 30 minutes in the centrifuge with 45° angle black anodized rotor. 25 µL 10% trifluoroacetic acid was added just before application to reverse phase. Samples were processed on µElute plate and collected in PCR plate. Samples were dried in the vacuum centrifuge. Aliquots were re-suspended with 5 µL of re-suspension buffer of IPA and formic containing post-processing standard, bradykinin and renin at 3000 nM actual concentration in resuspended serum. Samples were vortexed for two minutes and centrifuged for 10 sec. After sample preparation the 4 separate preparations were pooled and re-aliquoted.

The mass spectrometer was set up with the inlet capillary voltage to 280, PMT bias to −770, and MCP bias to −6000 in the volts window. The scan range was set to 122496, Number of Scans to 8000, Acq. Bin Width to 1 and threshold to 35. The spiked serum sample was run in the CE-MS to verify the intensities, resolution and migration times for the standards.

The mass spectrometer was rinsed with sample and then loaded with a chip of 1 µM set 6 in 20% IPA, 0.05% formic acid for chip infusion. A single use vial is run of set 6 1 µM in 20% IPA 0.05% forming acid for chip infusion. After the pre-run is complete, the signal and resolution of the 1 µM neurotensin$^{3+}$ peak at 558.3 m/z is monitored. The inlet lens voltage is adjusted in 0.05 V increments to obtain the optimum counts and resolution for neurotensin$^{3+}$ (signal intensity: ≧150,000 counts; resolution: 6000-8000). When the intensity and resolution fall within these limits, another Spiked Serum A was run.

Sample runs: Samples are removed from −20° C. freezer and stored on ice during CE-MS runs for no longer than 4 hours. One sample is used to complete 1 CE-MS run and obtain the data. During sample runs, sprays were visually inspected for stability.

Data Analysis

CE-MS data were analyzed several ways after data quality assurance. Peaks were identified using several methods, including mass-spectrometry-specific signal processing methods. First, univariate statistics were used to find single peak and/or component intensities that correlate with the presence/absence of prostate cancer. Standard non-parametric methods were used due to small sample size and the inability to assume normality of data. Such methods include the Mann-Whitney test. Second, after ranking by P-value, results were visualized, and those peaks/components that have high group-mean differences were determined. Third, a suite of feature selection and pattern classification methods were used to find multi-variate patterns that distinguish between the presence and absence of prostate cancer. These methods include support vector machines, discriminant analysis, and other machine learning methods. Cross-validation techniques were utilized to train and test patterns. The sensitivities, specificities and positive/negative predictive values of patterns that can highly discriminate between classes were determined. Proteomic data were analyzed with and without PSA scores and other clinical measurements available.

The markers identified are shown in Tables 9 and 10A-10D below.

TABLE 9

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 1* | 1 | 2.9511E+02 | monoisotopic | 294 | 214 | down |
| 2 | 9 | 1.5433E+03 | average | 13880 | 452 | up |
| | 10 | 1.3890E+03 | average | 13880 | 452 | |
| | 11 | 1.2629E+03 | average | 13880 | 452 | |
| | 12 | 1.1577E+03 | average | 13880 | 452 | |
| | 13 | 1.0687E+03 | average | 13880 | 452 | |
| | 14 | 9.9246E+02 | average | 13880 | 452 | |
| | 15 | 9.2636E+02 | average | 13880 | 452 | |
| | 16 | 8.6852E+02 | average | 13880 | 452 | |
| | 17 | 8.1749E+02 | average | 13880 | 452 | |
| | 18 | 7.7213E+02 | average | 13880 | 452 | |

TABLE 9-continued

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| | 19 | 7.3155E+02 | average | 13880 | 452 | |
| | 20 | 6.9502E+02 | average | 13880 | 452 | |
| | 21 | 6.6197E+02 | average | 13880 | 452 | |

*molecular weight for the indicated monoisotopic entities is as shown or +1 dalton

TABLE 10A

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 3 | 2 | 5.2576E+02 | monoisotopic | 1050 | 230 | down |
| 4 | 1 | 5.2035E+02 | monoisotopic | 519 | 192 | down |
| | 2 | 2.6067E+02 | monoisotopic | 519 | 192 | |
| 5 | 8 | 1.1336E+03 | average | 9061 | 708 | up |
| | 9 | 1.0077E+03 | average | 9061 | 708 | |
| | 10 | 9.0707E+02 | average | 9061 | 708 | |
| 6 | 4 | 1.0513E+03 | monoisotopic | 4201 | 341 | up |
| | 5 | 8.4127E+02 | monoisotopic | 4201 | 341 | |
| 7* | 1 | 4.9723E+02 | monoisotopic | 496 | 279 | down |
| 8 | 3 | 1.1113E+03 | monoisotopic | 3331 | 452 | up |
| | 4 | 8.3369E+02 | monoisotopic | 3331 | 452 | |
| | 5 | 6.6715E+02 | monoisotopic | 3331 | 452 | |
| 9 | 3 | 7.2164E+02 | monoisotopic | 2162 | 495 | up |
| | 4 | 5.4148E+02 | monoisotopic | 2162 | 495 | |
| 10 | 6 | 1.0291E+03 | average | 6169 | 452 | up |
| | 7 | 8.8222E+02 | average | 6169 | 452 | |
| | 8 | 7.7207E+02 | average | 6169 | 452 | |
| 11 | 4 | 8.2773E+02 | monoisotopic | 3307 | 331 | up |
| 12 | 7 | 1.3279E+03 | average | 9288 | 643 | up |
| | 8 | 1.1620E+03 | average | 9288 | 643 | |
| | 9 | 1.0330E+03 | average | 9288 | 643 | |
| | 10 | 9.2982E+02 | average | 9288 | 643 | |
| 13 | 7 | 1.1050E+03 | average | 7728 | 400 | up |
| | 8 | 9.6701E+02 | average | 7728 | 400 | |
| | 9 | 8.5967E+02 | average | 7728 | 400 | |
| 14 | 7 | 1.3279E+03 | average | 9289 | 633 | up |
| | 8 | 1.1621E+03 | average | 9289 | 633 | |
| | 9 | 1.0331E+03 | average | 9289 | 633 | |
| | 10 | 9.2986E+02 | average | 9289 | 633 | |
| 15 | 4 | 8.0696E+02 | monoisotopic | 3224 | 564 | up |
| | 5 | 6.4576E+02 | monoisotopic | 3224 | 564 | |
| 16 | 1 | 7.6536E+02 | monoisotopic | 764 | 235 | down |
| | 2 | 3.8318E+02 | monoisotopic | 764 | 235 | |
| 17* | 1 | 6.1935E+02 | monoisotopic | 618 | 265 | up |
| 18 | 6 | 9.5430E+02 | average | 5720 | 483 | up |
| | 7 | 8.1812E+02 | average | 5720 | 483 | |
| | 8 | 7.1598E+02 | average | 5720 | 483 | |
| | 9 | 6.3653E+02 | average | 5720 | 483 | |

*molecular weight for the indicated monoisotopic entities is as shown or +1 dalton

TABLE 10B

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 19 | 2 | 6.9929E+02 | monoisotopic | 1397 | 246 | up |
| 20 | 12 | 9.5422E+02 | average | 11439 | 482 | up |
| | 13 | 8.8089E+02 | average | 11439 | 482 | |
| | 14 | 8.1804E+02 | average | 11439 | 482 | |
| | 15 | 7.6357E+02 | average | 11439 | 482 | |
| | 16 | 7.1591E+02 | average | 11439 | 482 | |
| | 17 | 6.7386E+02 | average | 11439 | 482 | |
| | 18 | 6.3648E+02 | average | 11439 | 482 | |

TABLE 10B-continued

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 21 | 13 | 1.0812E+03 | average | 14043 | 451 | up |
|  | 14 | 1.0040E+03 | average | 14043 | 451 |  |
|  | 15 | 9.3718E+02 | average | 14043 | 451 |  |
|  | 16 | 8.7867E+02 | average | 14043 | 451 |  |
|  | 17 | 8.2704E+02 | average | 14043 | 451 |  |
|  | 18 | 7.8115E+02 | average | 14043 | 451 |  |
|  | 19 | 7.4009E+02 | average | 14043 | 451 |  |
| 22 | 3 | 5.4295E+02 | monoisotopic | 1626 | 470 | up |
|  | 4 | 4.0747E+02 | monoisotopic | 1626 | 470 |  |
| 23* | 1 | 3.3413E+02 | monoisotopic | 333 | 296 | up |
| 24 | 13 | 1.0569E+03 | average | 13727 | 455 | up |
|  | 14 | 9.8152E+02 | average | 13727 | 455 |  |
|  | 15 | 9.1615E+02 | average | 13727 | 455 |  |
|  | 16 | 8.5896E+02 | average | 13727 | 455 |  |
|  | 17 | 8.0849E+02 | average | 13727 | 455 |  |
|  | 18 | 7.6363E+02 | average | 13727 | 455 |  |
|  | 19 | 7.2349E+02 | average | 13727 | 455 |  |
| 25 | 14 | 9.9214E+02 | average | 13876 | 494 | up |
|  | 15 | 9.2607E+02 | average | 13876 | 494 |  |
|  | 16 | 8.6825E+02 | average | 13876 | 494 |  |
|  | 17 | 8.1723E+02 | average | 13876 | 494 |  |
|  | 18 | 7.7189E+02 | average | 13876 | 494 |  |
| 26* | 1 | 2.2911E+02 | monoisotopic | 228 | 193 | down |
| 27* | 1 | 3.2712E+02 | monoisotopic | 326 | 194 | up |
| 28 | 2 | 4.8368E+02 | monoisotopic | 965 | 199 | up |
| 29* | 1 | 2.5715E+02 | monoisotopic | 256 | 199 | down |
| 30 | 1 | 6.2533E+02 | monoisotopic | 624 | 306 | up |
|  | 2 | 3.1316E+02 | monoisotopic | 624 | 306 |  |
|  | 3 | 2.0911E+02 | monoisotopic | 624 | 306 |  |
| 31 | 2 | 4.4813E+02 | monoisotopic | 894 | 235 | down |

*molecular weight for the indicated monoisotopic entities is as shown or +1 dalton

TABLE 10C

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 32 | 1 | 8.5739E+02 | monoisotopic | 856 | 235 | down |
|  | 2 | 4.2920E+02 | monoisotopic | 856 | 235 |  |
| 33 | 7 | 1.7797E+03 | average | 12451 | 373 | up |
|  | 8 | 1.5574E+03 | average | 12451 | 373 |  |
|  | 9 | 1.3845E+03 | average | 12451 | 373 |  |
| 34 | 3 | 6.1932E+02 | monoisotopic | 1855 | 328 | up |
| 35 | 10 | 1.1739E+03 | average | 11729 | 601 | up |
|  | 11 | 1.0673E+03 | average | 11729 | 601 |  |
|  | 12 | 9.7840E+02 | average | 11729 | 601 |  |
|  | 13 | 9.0322E+02 | average | 11729 | 601 |  |
|  | 14 | 8.3878E+02 | average | 11729 | 601 |  |
| 36 | 13 | 1.0700E+03 | average | 13897 | 451 | up |
|  | 14 | 9.9366E+02 | average | 13897 | 451 |  |
|  | 15 | 9.2748E+02 | average | 13897 | 451 |  |
|  | 16 | 8.6957E+02 | average | 13897 | 451 |  |
|  | 17 | 8.1848E+02 | average | 13897 | 451 |  |
|  | 18 | 7.7307E+02 | average | 13897 | 451 |  |
|  | 19 | 7.3243E+02 | average | 13897 | 451 |  |
|  | 20 | 6.9586E+02 | average | 13897 | 451 |  |
| 37 | 11 | 1.2593E+03 | average | 13841 | 443 | up |
|  | 12 | 1.1544E+03 | average | 13841 | 443 |  |
|  | 13 | 1.0657E+03 | average | 13841 | 443 |  |
|  | 14 | 9.8967E+02 | average | 13841 | 443 |  |
|  | 15 | 9.2376E+02 | average | 13841 | 443 |  |
|  | 16 | 8.6609E+02 | average | 13841 | 443 |  |
|  | 17 | 8.1520E+02 | average | 13841 | 443 |  |
|  | 18 | 7.6997E+02 | average | 13841 | 443 |  |
|  | 19 | 7.2949E+02 | average | 13841 | 443 |  |

*molecular weight for the indicated monoisotopic entities is as shown or +1 dalton

TABLE 10D

| Biomarker | Charge | Observed m/z (thomson) | monoisotopic* or average for m/z | Molecular Weight (Daltons) | Separation Time (sec) (+/−64 sec for 95% CI) | up or down regulated in cancer cells |
|---|---|---|---|---|---|---|
| 38 | 11 | 1.2717E+03 | average | 13978 | 452 | up |
|  | 12 | 1.1659E+03 | average | 13978 | 452 |  |
|  | 13 | 1.0762E+03 | average | 13978 | 452 |  |
|  | 14 | 9.9944E+02 | average | 13978 | 452 |  |
|  | 15 | 9.3288E+02 | average | 13978 | 452 |  |
|  | 16 | 8.7464E+02 | average | 13978 | 452 |  |
|  | 17 | 8.2325E+02 | average | 13978 | 452 |  |
|  | 18 | 7.7757E+02 | average | 13978 | 452 |  |
| 39 | 6 | 1.1060E+03 | average | 6630 | 585 | up |
|  | 7 | 9.4818E+02 | average | 6630 | 585 |  |
|  | 8 | 8.2978E+02 | average | 6630 | 585 |  |
|  | 9 | 7.3769E+02 | average | 6630 | 585 |  |
|  | 10 | 6.6402E+02 | average | 6630 | 585 |  |
|  | 11 | 6.0375E+02 | average | 6630 | 585 |  |
| 40* | 1 | 6.8650E+02 | monoisotopic | 686 | 195 | up |
| 41* | 1 | 3.1314E+02 | monoisotopic | 312 | 305 | up |
| 42 | 2 | 7.3335E+02 | monoisotopic | 1465 | 266 | down |
|  | 3 | 4.8924E+02 | monoisotopic | 1465 | 266 |  |
|  | 4 | 3.6718E+02 | monoisotopic | 1465 | 266 |  |
| 43 | 2 | 4.9167E+02 | monoisotopic | 981 | 198 | up |
| 44 | 1 | 9.4442E+02 | monoisotopic | 943 | 198 | up |
|  | 2 | 4.7271E+02 | monoisotopic | 943 | 198 |  |
| 45* | 1 | 2.7310E+02 | monoisotopic | 272 | 192 | down |
| 46* | 1 | 229.1146625 | monoisotopic | 228 | 337 | down |
| 47* | 1 | 342.145859 | monoisotopic | 341 | 440 | up |

*molecular weight for the indicated monoisotopic entities is as shown or +1 dalton The above examples are in no way intended to limit the scope of the invention. Further, it can be appreciated to one of ordinary skill in the art that many changes and modifications can be made thereto without departing from the spirit or scope of the appended claims, and such changes and modifications are contemplated within the scope of the instant invention.

Example 10

In one embodiment, deciding whether a test sample comes from a patient that has prostate cancer is computed as follows:

Identify the intensity levels for every marker in Table 6 for every reference sample and for the test sample. The reference samples are those samples defined in the study design. Sum together the intensities for all charge states for a given biomarker. This yields a set of summed intensities, two intensities for every sample. Let the intensities for the test sample be identified by T=(biomarker 1 intensity for test sample, biomarker 2 intensity for test sample). Let the intensities for each of the reference samples be identified by R(i)=(biomarker 1 intensity for sample i, biomarker 2 intensity for sample i).

A comparison between the test sample, T, and reference sample, R(i), is done by taking a dot product between the two:

$(T*R(i))$=(biomarker 1 intensity for test sample)*(biomarker 1 intensity for sample $i$)+(biomarker 2 intensity for test sample)*(biomarker 2 intensity for sample $i$)

A decision function, D, is made from these comparisons by computing a function that appropriately weights them:

$D=(\sum\backslash alpha\_i*(T*R(i)))+b$

The alpha_i and b parameters are numbers that are appropriate for deciding whether the patient has prostate cancer based on the reference samples.

The decision is made that the patient has prostate cancer if the function D is greater than 0 and that the patient does not have prostate cancer if the function D is less than or equal to 0.

What is claimed is:

1. A method of identifying candidate biomarkers in the plasma microparticle sub-proteome, comprising: (a) isolating proteins from blood plasma microparticles obtained from at least one blood sample from a case and at least one blood sample from a control; (b) identifying the proteins; (c) applying a statistical test to measure the abundance of each protein identified; and, (d) determining the presence of positive and negative biomarkers by comparing the abundance of each protein identified in at least one case blood sample with the abundance of the same protein in at least one control blood sample.

2. The method of claim 1, wherein (b) identifying is performed by sequencing the resulting proteins or peptides.

3. The method of claim 2, wherein (b) identifying is performed by sequencing the resulting peptides.

4. The method of claim 3, wherein the sequencing is performed by mass spectrometry.

5. The method of claim 4, wherein the sequencing is performed by a HPLC-MS/MS.

6. The method of claim 1, wherein (c) applying a statistical test is performed by using a method selected from: ion current, spectral count, and coverage.

7. The method of claim 6 wherein the statistical method used is comparing spectral counts between cases and controls.

8. The method of claim 1, wherein isolating proteins (a), further comprises:
(e) isolating a plasma microparticle-enriched fraction from a blood sample; (f) purifying plasma microparticles from the enriched fraction; and, (g) isolating proteins from the purified microparticles.

9. The method of claim 8, further comprising: (l) optionally cleaving the resulting proteins to obtain peptides.

10. The method of claim 9, wherein (l) cleaving is performed by digesting the delipidated proteins with an appropriate enzyme.

11. The method of claim 10, wherein the enzyme is trypsin.

12. The method of claim 8, wherein isolating a plasma microparticle-enriched fraction (e), comprises: (h) separating platelet-poor plasma (PPP) from a blood sample; and, (i) fractionating by size to obtain a plasma microparticle-enriched fraction.

13. The method of claim 12, wherein (h) separating the plasma microparticle-enriched fraction is performed by centrifugation.

14. The method of claim 12, wherein (i) purifying by fractionating by size is performed by running the fractionated plasma microparticles through a size exclusion column.

15. The method of claim 12, wherein purifying plasma microparticles (f), comprises: (j) fractionating the plasma microparticle-enriched fraction to obtain plasma microparticles.

16. The method of claim 15, wherein (j) fractionating the PPP is performed by centrifugation.

17. The method of claim 16, wherein the centrifugation is sufficient to form a pellet comprising: plasma microparticles.

18. The method of claim 15, wherein isolating proteins (g), comprises: (k) delipidating the resulting plasma microparticles to obtain proteins.

19. The method of claim 18, wherein (k) delipidating is performed by submitting the plasma microparticles to gel electrophoresis.

20. The method of claim 19, wherein the gel electrophoresis is 1D SDS PAGE.

* * * * *